US011848082B2

(12) United States Patent
Aravamudan et al.

(10) Patent No.: US 11,848,082 B2
(45) Date of Patent: *Dec. 19, 2023

(54) SYSTEMS AND METHODS FOR COMPUTING WITH PRIVATE HEALTHCARE DATA

(71) Applicant: nference, inc., Cambridge, MA (US)

(72) Inventors: Murali Aravamudan, Andover, MA (US); Karthik Murugadoss, Cambridge, MA (US); Sankar Ardhanari, Chapel Hill, NC (US); Ajit Rajasekharan, West Windsor, NJ (US); Akash Anand, Bhagalpur (IN); Rakesh Barve, Bangalore (IN); Venkataramanan Soundararajan, Andover, MA (US); Samir Awasthi, Jamaica Plain, MA (US); Tyler Wagner, Boston, MA (US); Shamim Naqvi, Morristown, NJ (US)

(73) Assignee: Nference, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/935,852

(22) Filed: Sep. 27, 2022

(65) Prior Publication Data

US 2023/0044294 A1    Feb. 9, 2023

Related U.S. Application Data

(63) Continuation of application No. 16/908,520, filed on Jun. 22, 2020, now Pat. No. 11,545,242.

(Continued)

(51) Int. Cl.
*G06F 21/60* (2013.01)
*H04L 29/06* (2006.01)
(Continued)

(52) U.S. Cl.
CPC ............. *G16H 10/60* (2018.01); *G06F 21/53* (2013.01); *G06F 21/602* (2013.01); *G06F 21/64* (2013.01)

(58) Field of Classification Search
CPC ....... G16H 10/60; G06F 21/53; G06F 21/602; G06F 21/64; G06F 21/6245
See application file for complete search history.

(56) References Cited

U.S. PATENT DOCUMENTS 7,542,969 B1   6/2009  Rappaport et al.
9,514,405 B2  12/2016  Chen et al.
(Continued)

FOREIGN PATENT DOCUMENTS

CN    105938495 A    9/2016
JP    2019-536178 A  12/2019
(Continued)

OTHER PUBLICATIONS

AMD Secure Encrypted Virtualization (SEV), https://developer.amd.com/sev/, accessed Sep. 23, 2020 (5 pages).

(Continued)

*Primary Examiner* — Izunna Okeke
(74) *Attorney, Agent, or Firm* — CALDWELL INTELLECTUAL PROPERTY LAW

(57) ABSTRACT

Techniques are provided for computing with private healthcare data. The techniques include a method comprising constructing an isolated memory partition that forms a secure enclave and pre-provisioning software within the secure enclave. The pre-provisioned software is configured to receive at least one of input data or the instructions for the one or more application computing processes in an encrypted form; decrypt the at least one of input data or instructions using one or more cryptographic keys; execute the one or more application computing processes based on the decrypted at least one of input data or instructions to generate output data; generate a proof of execution that (Continued)

indicates that the one or more application computing processes operated on the received input data; encrypt the output data using the one or more cryptographic keys; and provide external access to the encrypted output data and the proof of execution.

32 Claims, 30 Drawing Sheets

Related U.S. Application Data

(60) Provisional application No. 63/012,738, filed on Apr. 20, 2020, provisional application No. 62/984,989, filed on Mar. 4, 2020, provisional application No. 62/985,003, filed on Mar. 4, 2020, provisional application No. 62/962,146, filed on Jan. 16, 2020, provisional application No. 62/865,030, filed on Jun. 21, 2019.

(51) Int. Cl.
  *G16H 10/60* (2018.01)
  *G06F 21/64* (2013.01)
  *G06F 21/53* (2013.01)

(56) References Cited

U.S. PATENT DOCUMENTS

| | | |
|---|---|---|
| 9,953,095 B1 | 4/2018 | Scott et al. |
| 10,360,507 B2 | 7/2019 | Aravamudan et al. |
| 11,062,218 B2 | 7/2021 | Aravamudan et al. |
| 11,487,902 B2 | 11/2022 | Ardhanari et al. |
| 11,545,242 B2 | 1/2023 | Aravamudan |
| 2004/0013302 A1 | 1/2004 | Ma et al. |
| 2007/0039046 A1 | 2/2007 | Van Dijk et al. |
| 2008/0118150 A1 | 5/2008 | Balakrishnan et al. |
| 2008/0243825 A1 | 10/2008 | Staddon et al. |
| 2009/0116736 A1 | 5/2009 | Neogi et al. |
| 2011/0255788 A1 | 10/2011 | Duggan et al. |
| 2011/0307460 A1 | 12/2011 | Vadlamani et al. |
| 2013/0132331 A1 | 5/2013 | Kowalczyk et al. |
| 2015/0161413 A1* | 6/2015 | Calem .......... G16H 10/60 705/51 |
| 2015/0254555 A1 | 9/2015 | Williams, Jr. et al. |
| 2016/0105402 A1 | 4/2016 | Soon-Shiong et al. |
| 2016/0247307 A1 | 8/2016 | Stoop et al. |
| 2017/0032243 A1 | 2/2017 | Corrado et al. |
| 2017/0061326 A1 | 3/2017 | Talathi et al. |
| 2017/0091391 A1 | 3/2017 | LePendu |
| 2018/0060282 A1 | 3/2018 | Kaljurand |
| 2019/0319982 A1* | 10/2019 | Durand .......... H04L 63/04 |
| 2019/0354883 A1 | 11/2019 | Aravamudan et al. |
| 2020/0402625 A1 | 12/2020 | Aravamudan et al. |
| 2021/0019287 A1 | 1/2021 | Prasad et al. |
| 2021/0224264 A1 | 7/2021 | Barve et al. |
| 2021/0248268 A1 | 8/2021 | Ardhanari et al. |
| 2022/0050921 A1 | 2/2022 | LaFever et al. |
| 2022/0138599 A1 | 5/2022 | Aravamudan et al. |
| 2023/0051067 A1 | 2/2023 | Ardhanari |

FOREIGN PATENT DOCUMENTS

| | | |
|---|---|---|
| WO | WO-2015149114 | 10/2015 |
| WO | WO-2018057945 | 3/2018 |
| WO | WO-2020257783 | 12/2020 |
| WO | WO-2021011776 | 1/2021 |
| WO | WO-2021146694 A1 | 7/2021 |
| WO | WO-2021178689 | 9/2021 |

OTHER PUBLICATIONS

Arora, S. et al., "A Simple But Tough-To-Beat Baseline for Sentence Embeddings", ICLR, 2017 (16 pages).
AWS Key Management Service (KMS), https://aws.amazon.com/kms, accessed Jan. 20, 2021 (3 pages).
AWS Key Management Service (KMS), https://aws.amazon.com/kms, accessed Sep. 23, 2020 (6 pages).
Bartunov, S. et al., "Breaking Sticks And Ambiguities With Adaptive Skip-Gram", retrieved online from URL:< https://arxiv.org/pdf/1502.07257.pdf>,[cs.CL], Nov. 15, 2015 (15 pages).
Bojanowski, P. et al., "Enriching Word Vectors with Subword Information", retrieved online from URL:<https://arxiv.org/pdf/1607.04606.pdf>, [cs.CL], Jun. 19, 2017 (12 pages).
Confidental Computing Consortium, "What is the Confidential Computing Consortium?", https://confidentialcomputing.io, accessed Sep. 24, 2020 (2 pages).
De Guzman, C.G. et al., "Hematopoietic Stem Cell Expansion and Distinct Myeloid Developmental Abnormalities in a Murine Model of the AML1-ETO Translocation", Molecular and Cellular Biology, 22(15):5506-5517, Aug. 2002 (12 pages).
Desagulier, G., "A lesson from associative learning: asymmetry and productivity in multiple-slot constructions", Corpus Linguistic and Linguistic Theory, 12(2):173-219, 2016, submitted Aug. 13, 2015, <http://www.degruyter.com/view/j/cllt.2016.12.issue-2/cllt-2015-0012/cllt-2015-0012.xml?format=INT>. <10.1515/cllt-2015-0012>. <halshs-01184230>, (32 pages).
Devlin, J. et al., "BERT: Pre-training of Deep Bidirectional Transformers for Language Understanding", arXiv:1810.04805v2 [cs.CL], May 24, 2019 (16 pages).
Divatia, A., "The Fact and Fiction of Homomorphic Encryption", Dark Reading, www.darkreading.com/attacks-breaches/the-fact-and-fiction-of-homomorphic-encryption/a/d-id/1333691, Jan. 22, 2019 (3 pages).
Dwork, C., "Differential Privacy: A Survey of Results", Lecture Notes in Computer Science, vol. 4978, pp. 1-19, 2008 (19 pages).
Ferraiuolo, A. et al., "Komodo: Using verification to disentangle secure-enclave hardware from software", SOSP '17, Shanghai, China, pp. 287-305, Oct. 28, 2017 (19 pages).
Garten, Y. et al., "Pharmspresso: a text mining tool for extraction of pharmacogenomic concepts and relationships from full text", BMC Bioinformatics, 10(Suppl. 2):S6, Feb. 5, 2009 (9 pages).
Genkin, D. et al., "Privacy in Decentralized Cryptocurrencies", Communications of the ACM, 61(6):78-88, Jun. 2018 (11 pages).
Hageman, G.S. et al., "A common haplotype in the complement regulatory gene factor H (HF1 / CFH) predisposes individuals to age-related macular degeneration", PNAS, 102(20):7227-7232, May 17, 2005 (6 pages).
Ikeda, T. et al., "Anticorresponding mutations of the KRAS and PTEN genes in human endometrial cancer", Oncology Reports, 7: 567-570, published online May 1, 2000 (4 pages).
Intel, "What is Intel® SGX?", http://www.intel.com/content/www/us/en/architecture-and-technology/software-guard-extensions.html, accessed Sep. 23, 2020 (8 pages).
International Preliminary Report on Patentability issued in International Application No. PCT/US2021/020906, dated Sep. 15, 2022 (9 pages).
International Search Report and Written Opinion issued by the European Patent Office as International Searching Authority in International Application PCT/US2017/053039, dated Dec. 20, 2017 (15 pages).
International Search Report and Written Opinion issued by the U.S. Patent and Trademark Office as International Searching Authority issued in International Application No. PCT/US21/20906, dated May 19, 2021 (10 pages).
International Search Report and Written Opinion issued by U.S. Patent and Trademark Office as International Searching Authority in International Application No. PCT/US20/42336, dated Sep. 30, 2020 (10 pages).
International Search Report and Written Opinion issued by U.S. Patent and Trademark Office as International Searching Authority, for International Application No. PCT/US20/38987, dated Nov. 9, 2020 (26 pages).
Joulin, A. et al., "Bag of Tricks for Efficient Text Classification", retrieved online from URL:<https://arXiv.org/pdf/1607.01759v3.pdf>, [cs.CL], Aug. 9, 2016 (5 pages).

(56) References Cited

OTHER PUBLICATIONS

Kiros, R. et al., "Skip-Thought Vectors", retrieved online from URL:<https://arXiv.org/abs/1506.06726v.1>, [cs.CL], Jun. 22, 2015 (11 pages).

Kolte, P. "Why Is Homomorphic Encryption Not Ready For Primetime?", Baffle, https://baffle.io/blog/why-is-homomorphic-encryption-not-ready-for-primetime/, Mar. 17, 2017 (4 pages).

Korger, C., "Clustering of Distributed Word Representations and its Applicability for Enterprise Search", Doctoral Thesis, Dresden University of Technology, Faculty of Computer Science, Institute of Software and Multimedia Technology, Matriculation Nr. 3703541, submitted Jul. 28, 2016 (116 pages).

Kutuzov, A. et al., "Cross-lingual Trends Detection for Named Entities in News Texts with Dynamic Neural Embedding Models", Proceedings of the NewsIR'16 Workshop at ECIR, Padua, Italy, Mar. 20, 2016 (6 pages).

Le, Q. et al., "Distributed Representations of Sentences and Documents", Proceedings of the 31st International Conference of Machine Learning, Beijing, China, vol. 32, 2014 (9 pages).

Li, H. et al., "Cheaper and Better: Selecting Good Workers for Crowdsourcing," retrieved online from URL: https://arXiv.org/abs/1502.00725v.1, pp. 1-16, Feb. 3, 2015 (16 pages).

Ling, W. et al., "Two/Too Simple Adaptations of Word2Vec for Syntax Problems", retrieved online from URL:<https://cs.cmu.edu/~lingwang/papers/naacl2015.pdf>, 2015 (6 pages).

Maxwell, K.N. et al., "Adenoviral-mediated expression of Pcsk9 in mice results in a low-density lipoprotein receptor knockout phenotype", PNAS, 101(18):7100-7105, May 4, 2004 (6 pages).

Mikolov, T. et al., "Distributed Representations for Words and Phrases and their Compositionality", retrieved online from URL:https://arXiv.org/abs/1310.4546.v1 [cs.CL], Oct. 16, 2013 (9 pages).

Mikolov, T. et al., "Efficient Estimation of Word Representations in Vector Space", retrieved online from URL: https://arXiv.org/abs/1301.3781v3 [cs.CL] Sep. 7, 2013 (12 pages).

Murray, K., "A Semantic Scan Statistic for Novel Disease Outbreak Detection", Master's Thesis, Carnegie Mellon University, Aug. 16, 2013 (68 pages).

Neelakantan, A., et al., "Efficient Non-parametric Estimation of Multiple Embeddings per Word in Vector Space," Department of Computer Science, University of Massachusetts, (2015) (11 pages).

Pennington, J. et al., "GloVe: Global Vectors for Word Representation", retrieved online from URL:<https://nlp.stanford.edu/projects/glove.pdf>, 2014 (12 pages).

Rajagopalan, H., et al., "Tumorigenesis: RAF/RAS oncogenes and mismatch-repair status", Nature, 418:934, Aug. 29, 2002 (1 page).

Rajasekharan, "Unsupervised NER using BERT", [accessed Jun. 10, 2021], Toward Data Science, <URL: https://towardsdatascience.com/unsupervised-ner-using-bert-2d7af5f90b8a>, Feb. 28, 2020 (27 pages).

Shamir, A. "How to Share a Secret", Communications of the ACM, 22(11):612-613, Nov. 1979 (2 pages).

Shweta, Fnu et al., "Augmented Curation of Unstructured Clinical Notes from a Massive EHR System Reveals Specific Phenotypic Signature of Impending COVID-19 Diagnosis", https://www.medrxiv.org/content/10.1101/2020.04.19.20067660v3.full, accessed Sep. 24, 2020 (24 pages).

Van Mulligen, E.M. et al., "The EU-ADR corpus: Annotated drugs, diseases, targets, and their relationships", Journal of Biomedical Informatics, 45:879-884, published online Apr. 25, 2012 (6 pages).

Wieting, J. et al., "Revisiting Recurrent Networks for Paraphrastic Sentence Embeddings", retrieved online from URL:<https://arXiv.org/pdf/1705.00364v1.pdf>, [cs.CL], Apr. 30, 2017 (12 pages).

Yao, Z. et al., "Dynamic Word Embeddings for Evolving Semantic Discovery", WSDM 2018, Marina Del Rey, CA, USA, Feb. 5-9, 2018 (9 pages).

Zuccon, G., et al., "Integrating and Evaluating Neural Word Embeddings in Information Retrieval", ADCS, Parramatta, NSW, Australia, Dec. 8-9, 2015 (8 pages).

\* cited by examiner

| Output Dataset | Policy |
|---|---|
| Does not contain any PII attributes | Unconstrained dataset |
| Contains PII attributes (greater than K records) | Unconstrained dataset in Secure Enclave (SE) |
| Contains PII attributes (less than K records) | Enclose output dataset in SE |
| | Encrypt output dataset using FHE |
| | Disallow output request |
| Contains PII data and output request is non-privacy preserving | Enclose output dataset in SE |
| | Disallow the request |

Fig. 3

| | Algorithm Provider 1 | Data Provider | Key Fragments | Link to Load Image |
|---|---|---|---|---|
| Group 1 | A1:a1 | D1: d1 | A1(k11), D1(k12) | L1 |
| Group 2 | A2:a2 | D2: d2 | A2(k21), D2(k22) | L2 |
| ... | ... | ... | ... | ... |

SYSTEMS AND METHODS FOR COMPUTING WITH PRIVATE HEALTHCARE DATA

RELATED APPLICATIONS

This application claims priority under 35 U.S.C. § 119(e) to U.S. Provisional Application No. 63/128,542, entitled "Systems and Methods for Computing with Private Healthcare Data," filed Dec. 21, 2020, U.S. Provisional Application No. 63/109,769, entitled "Systems and Methods for Computing with Private Healthcare Data," filed Nov. 4, 2020; and this application is a continuation-in-part of U.S. Nonprovisional application Ser. No. 16/908,520, entitled "Systems and Methods for Computing with Private Healthcare Data," filed Jun. 22, 2020 which claims priority to U.S. Provisional Application No. 62/865,030, entitled "Systems and Methods for Selective Information Masking in Text," filed Jun. 21, 2019, U.S. Provisional Application No. 62/962,146, entitled "Systems and Methods for Retrieving Information Responsive to a Query," filed Jan. 16, 2020, U.S. Provisional Application No. 62/984,989, entitled "Systems and Methods for Selective Information Masking in Text," filed Mar. 4, 2020, U.S. Provisional Application No. 62/985,003, entitled "Pipelined Federated Architecture for Computing with Private Healthcare Data," filed Mar. 4, 2020, and U.S. Provisional Application No. 63/012,738, entitled "Systems and Methods for Augmented Curation and Temporal Discrimination of Health Records," filed Apr. 20, 2020, each of which is incorporated by reference herein in its entirety.

TECHNICAL FIELD

The present invention relates generally to processing data that may contain information deemed private by consumers or regulations.

BACKGROUND

Hospitals, healthcare providers and care givers collect large amounts of data from patients. It is a necessary part of the processes by which healthcare is provided to members of the public. Typically, a patient provides data to the care giver as a part of receiving treatment for his/her ailments. This data is stored by the care giver and may be used later, inter alia, for research purposes. In another typical scenario data may be collected from consumers via one or more devices, e.g., pulse oximeter, glucose monitor, smart watch, fitness bracelet, etc. In such use cases, the collected data is often used to analyze a patient's health in a continuous manner or over a period of time. Consequently, huge amounts of patient information may be accumulated by service providers.

Many aspects of patient data collected by care givers and service providers may be subject to privacy regulations. The usefulness and benefit of processing data collected from patients is clear and acknowledged by the public. However, there is a growing concern of maintaining the privacy of user data, particularly when the data can be used to identify the patient. Such concerns are the basis of HIPAA (Health Insurance Portability and Accountability Act) regulations initially passed in 1996 by the US Congress. Many other countries have also promulgated similar regulations and legislations. Generally, HIPAA and other regulations limit the release of personal information that may result in identification of members of the public or details of their physical attributes or biometric data.

There is thus a need to enable biomedical (and other types of) data to be analyzed by computational processes under the constraint of maintaining the privacy of the individual patient or consumer. Such a system and methods will consequently be of great commercial, social and scientific benefit to society.

BRIEF DESCRIPTION OF THE DRAWINGS

FIG. 3 is a simplified diagram of illustrative policies applicable to datasets according to some embodiments.

FIG. 7 is a simplified diagram of a decentralized trust model according to some embodiments.

FIGS. 22A and 22B are screenshots of a graphical interface of an information retrieval system according to some embodiments

Figure 1A:
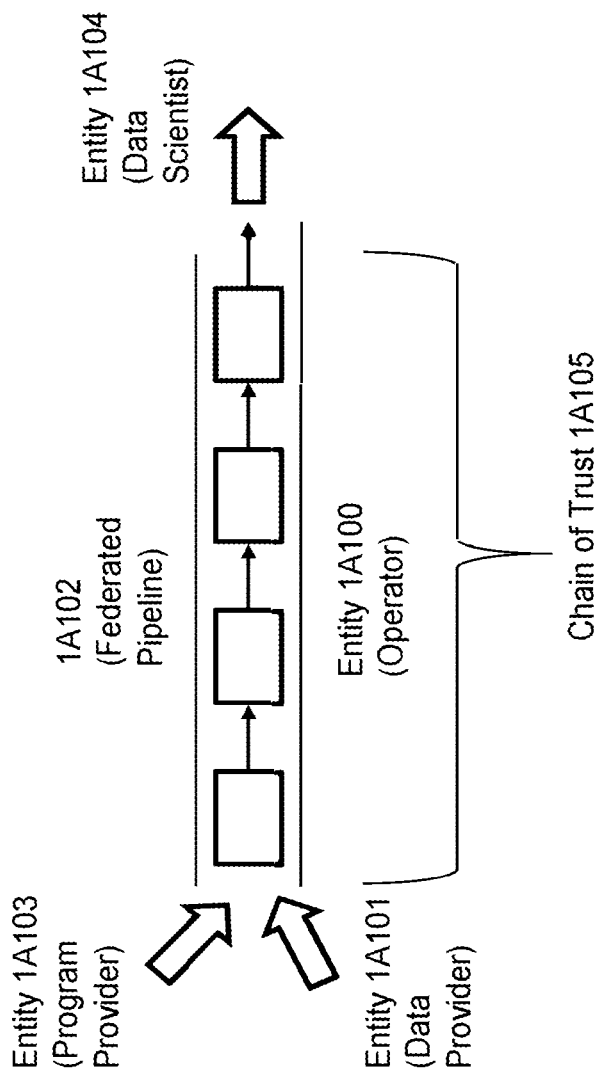
FIG. 1A is a diagram showing a federated approach to processing datasets containing private data.

Various objectives, features, and advantages of the disclosed subject matter can be more fully appreciated with reference to the following detailed description of the disclosed subject matter when considered in connection with the following drawings, in which like reference numerals identify like elements.

DETAILED DESCRIPTION

A truly astonishing amount of information has been collected from patients and consumers pertaining to their health status, habits, environment, surroundings, and homes. Increasingly, this information is being processed by computer programs utilizing machine learning and artificial intelligence models. Such computer programs have shown remarkable progress in analyzing and predicting consumer health status, incidence and treatment of diseases, user behavior, etc. Furthermore, since the collected data may contain patient biometric and other personal identification attributes, there is a growing concern that such computer programs may allow the identities of patients and consumers to be learned. Accordingly, enterprises interested in analyzing healthcare data containing private attributes are concerned with maintaining privacy of individuals and observing the relevant regulations pertaining to private and personal data, such as HIPAA (Health Insurance Portability and Accountability Act 1996) regulations.

In addition to HIPAA, many other regulations have been enacted in various jurisdictions, such as GDPR (General Data Protection Regulations) in the European Union, PSD2 (Revised Payment Services Directive), CCPA (California Consumer Privacy Act 2018), etc.

In the following descriptions, the terms "user information," "personal information," "personal health information ("PHI")," "healthcare information data or records," "identifying information," and PII (Personally Identifiable Information) may be used interchangeably. Likewise, the terms "electronic health records ("EHR")" and "data records" may be used interchangeably.

One approach to handling private data is to encrypt all the records of a dataset. Encrypted text is sometimes referred to as ciphertext; decrypted text is also referred to as plaintext. Encryption may be described, by way of analogy, as putting the records of the dataset in a locked box. Access to the records of the locked box is then controlled by the key to the locked box. The idea is that only authorized entities are allowed access to the (decryption) key.

Some regulations (e.g., HIPAA) require that healthcare data be stored in encrypted form. This is also sometimes referred to as "encryption at rest."

Malicious entities may, however, gain access to the decryption key or infer/guess the decryption key using computational mechanisms. The latter possibility becomes probable when the encryption/decryption technologies are not sufficiently strong (e.g., the length of the key—the number of bits comprising the key—is not sufficiently long to withstand computational attacks), or if the key is lost or not stored securely.

Encryption and other such security technologies may depend on the expectation that a computational attacker is likely to expend a certain amount of resources—computer time, memory and computing power—to gain access to the underlying data. The length of encryption keys is one of the variables used to increase the amount of computational resources needed to break the encryption.

Even strong encryption technology may not resolve security challenges associated with processing private data. For example, an enterprise that is processing an encrypted dataset may load the dataset into a computer, decrypt the dataset, process the records of the dataset and re-encrypt the dataset. In this example, one or more records of the dataset are decrypted (into plaintext) during processing. A malicious entity may gain access to the computer while the plaintext records are being processed, leading to a leak of personal information. That is, decrypting the data for the purpose of processing introduces a "run-time" vulnerability.

Accordingly, it would be desirable to develop improved techniques for processing private data.

Fully homomorphic encryption (FHE) describes an approach for computing with encrypted data without decrypting it. That is, given encrypted data elements $x_1^e, x_2^e, \ldots$ compute the function $f(x_1^e, x_2^e, \ldots)$ yielding an encrypted result $(y_1^e, y_2^e, \ldots)$. Since the input, output and processing phases of such computations deal with encrypted data elements only, the probability of leaks is minimized. If the (mathematical) basis of the encryption technology is sufficiently strong, the inference/guessing of keys may become an infeasible computation, even if very powerful computers, e.g., quantum computers, are used.

However, conventional techniques for computing with FHE datasets may be inefficient to the point of being impractical. Calculations reported in 2009 put computations running over FHE datasets as hundred trillion times slower than unencrypted data computations. (See Ameesh Divatia, https://www.darkreading.conattacks-breaches/the-fact-and-fiction-of-homomorphic-encryption/a/d-id/1333691 and Priyadarshan Kolte, https://baffle.io/blog/why-is-homomorphic-encryption-not-ready-for-primetime/.)

Furthermore, existing application code may need to be re-written to use FHE libraries that provide the basic FHE functions.

A secure enclave describes a computing environment where sensitive data can be decrypted and processed in memory without exposing it to the other processes running in the computer. Data is decrypted and processed in a computing environment that is "isolated" from other processes and networks. Protection of such an environment could be further enhanced by protecting the decryption keys in a manner explained later.

The technology of secure enclaves may be more efficient than FHE techniques.

In some instances, a computer containing a secure enclave may also be referred to as a secure computer. A secure computer may contain one or more secure enclaves, e.g., one secure enclave for each application running in the computer.

In general, it is a goal of secure enclave technology to ensure isolation of the enclave from other processes and from other enclaves.

A secure enclave is an isolated environment composed of hardware (CPU, memory, registers, cache, etc.) and/or software (programmed circuitry). The secure enclave is accessible by application programs via especially configured hardware and software elements, sometimes referred to as a call gate or a firewall. Access to the secure enclave may be controlled via cryptographic keys some of which may reside in hardware elements, configured at the time of manufacturing. A malicious entity could attempt to extract keys during the booting process of the secure enclave. Reverse engineering or other such attacks to extract keys may be thwarted by disallowing repeated key requests and/or lengthening the time between such requests. In some cases, a set of keys may be associated with a particular set of hardware elements.

Additional protection may be achieved by requiring that data (and computer programs) that are injected into a secure enclave be encrypted; further that data outputted from a secure enclave to be encrypted also. Encrypted data once injected into a secure enclave could then be decrypted within the secure enclave, processed, and the results could be encrypted in preparation for output. Thus, an isolated secure enclave solves the runtime vulnerability problem discussed above.

Additional measures of protecting the data within a secure enclave can be introduced by requiring that the process of decrypting the data inside the secure enclave be made more secure by protecting the decryption keys from being known outside the secure enclave. That is, entities external to the secure enclave infrastructure are prohibited from accessing the decryption key In this manner, encrypted data may be injected into a secure enclave when an injecting agent satisfies the constraints of the firewall of the secure enclave. The secure enclave includes a decryption key that may be used to decrypt the injected data and process it. The secure enclave may encrypt results of the processing activity using an encryption key available inside the secure enclave before outputting the results.

Another technique to address the issue of protecting private data is to de-identify or anonymize the data. This technique relies on replacing private data by random data, e.g., replacing social security numbers by random digits. Such techniques may be used in structured datasets. For example, a structured dataset comprising of names, social security number and heart rate of patients may be anonymized by de-identifying the values of the attributes "name" and "social security number."

De-identification technologies in structured datasets lead to loss of processing power as follows.

Structured datasets often need to be combined with other structured datasets to gain maximum processing advantage. Consider, by way of example, two structured datasets (name, SS #, heartrate) and (name, SS #, weight). By combining the two datasets, one may gain a more complete data record of a patient. That is, one may exploit the relationships inherent in the two datasets by associating the patients represented in the two datasets. The process of de-identifying the two datasets leads to anonymizing the patients which loses the inherent relationships.

To continue with the above example, in order to preserve the inherent relationship, the entity performing the de-identification may assign the same random data to the represented patients in the two datasets. That is, the anonymizing entity knows that a patient, say John, is represented by certain data in the two datasets. This implies that the knowledge of the entity doing the anonymizing becomes a vulnerability.

Thus, de-identifying structured data may lead to introducing vulnerabilities that may be exploited by malicious computational entities.

Another disadvantage of traditional de-identifying technologies is that it does not apply to unstructured datasets such as medical notes, annotations, medical history, pathology data, etc. A large amount of healthcare data consists of unstructured datasets. In a later part of this disclosure, techniques that use machine learning and artificial intelligence techniques to de-identify unstructured datasets are disclosed.

One consequence of de-identifying unstructured datasets is that the resulting dataset may contain some residual private data. In one embodiment, de-identification of an unstructured dataset is subjected to a statistical analysis that derives a measure of the effectiveness of the de-identification. That is, measures of the probability to which a dataset has been de-identified may be obtained.

In embodiments, an entity A de-identifies a dataset to a probability measure p, and provides it to an entity B. The latter also receives from an entity C one or more computer programs. Entity B processes the data received from entity A using the computer programs received from entity C and provides the result of the processing to another entity D. (In embodiments, A, B, C and D may be distinct entities in principle; in practice, one or more of entities A, B, C and D may be cooperate through mutual agreements.)

Embodiments of the present invention enable Entity B to assure entity A (and C, and D) that its processing maintains the probability p associated with the data.

Further, in a process not involving entity B, entity A may approve the use of computer programs of entity C on its dataset.

Embodiments of the present invention enable entity B to assure entity C (and A, and D) that the dataset in question was only processed by computer programs provided by entity C and that the dataset was not processed by any other computer program. Furthermore, entity B may be able to assure the other entities that the computer programs provided by entity C and used to process the underlying dataset were not altered, changed or modified in any manner, i.e., the binary image of the computer programs used during processing was identical to the binary image of the provided computer programs. That is, this enablement maintains the provenance of the received computer programs.

Furthermore, the inscrutability property corresponds to a property that satisfies the following conditions.
1. Entity B can assure entities A, C and D that it did not have access to the dataset provided by entity A, to the computer programs provided by entity C, and to the outputs provided to entity D.
2. Entity B can assure entities C and D that entity A only had access to dataset A and did not have access to either the computer programs provided by C or to the outputs provided to entity D.
3. Entity B can assure entities A and D that entity C only had access to its computer programs and did not have access either to the dataset provided by A or the outputs provided to D.
4. Entity B can assure entities C and D that entity A only had access to the dataset A that it provided and did not have access either to the outputs provided to D or to the computer programs provided by C.

Additionally, the various assurances above are provided in the form of verifiable and unforgeable data instruments, i.e., certificates, based on the technology of cryptography.

Embodiments of the present invention, shown in FIG. 1A, enable a first entity 1A100 to construct a "computational chain of trust" 1A105 originating at a point where it receives a dataset (with a pre-determined de-identified probability) from a second entity 1A101, extending through one or more data processing stages 1A102 using computer programs received from a third entity 1A103, and terminating at a point where the results of the processing are received by the fourth entity 1A104. Furthermore, the chain of trust 1A105 satisfies the inscrutability property. Thus, the chain of trust embodies the notions of preserving the input probability measure, the provenance of the received computer programs and the inscrutability property.

Without loss of generality and for ease of description, in the illustrative embodiment of FIG. 1A, the first entity A is labeled "operator," the second entity is labeled "data provider," the third entity is labeled "program provider," and the fourth entity is labeled "data scientist." The equipment performing the processing is labeled "federated pipeline." The term "federated" indicates that the pipeline may receive inputs from multiple entities and may provide outputs to multiple entities.

The present disclosure, inter alia, describes "federated pipelines" (implemented using software technologies and/or hardware/firmware components) that maintain the input de-identification probability of datasets, the provenance of input computer programs, and the inscrutability of the various data and computer programs involved in the computation.

In some cases, a data scientist (e.g., entity 1A104 cf. FIG. 1A), having obtained an output dataset or result from a federated pipeline, may wish to process the output dataset and share the result with a third party. Note that since the data scientist receives the output from a federated pipeline, as explained above, the output is associated with a (series of) attestations, i.e., a chain of trust. If the data scientist now wishes to process the received output and share it with a third party, the latter may ask that the chain of trust be extended to the newly processed result(s).

That is, the third party may wish to obtain a proof that the output received from the federated pipeline was indeed used as input to a new computer program and the output provided to the third-party is outputted by the said program. That is, the data scientist may be asked by the third-party to extend the chain of trust associated with the federated pipeline. If the data scientist is not associated with the federated pipeline, a method of extending the chain of trust is needed that is independent of the method(s) used in the federated pipeline system.

Figure 5:
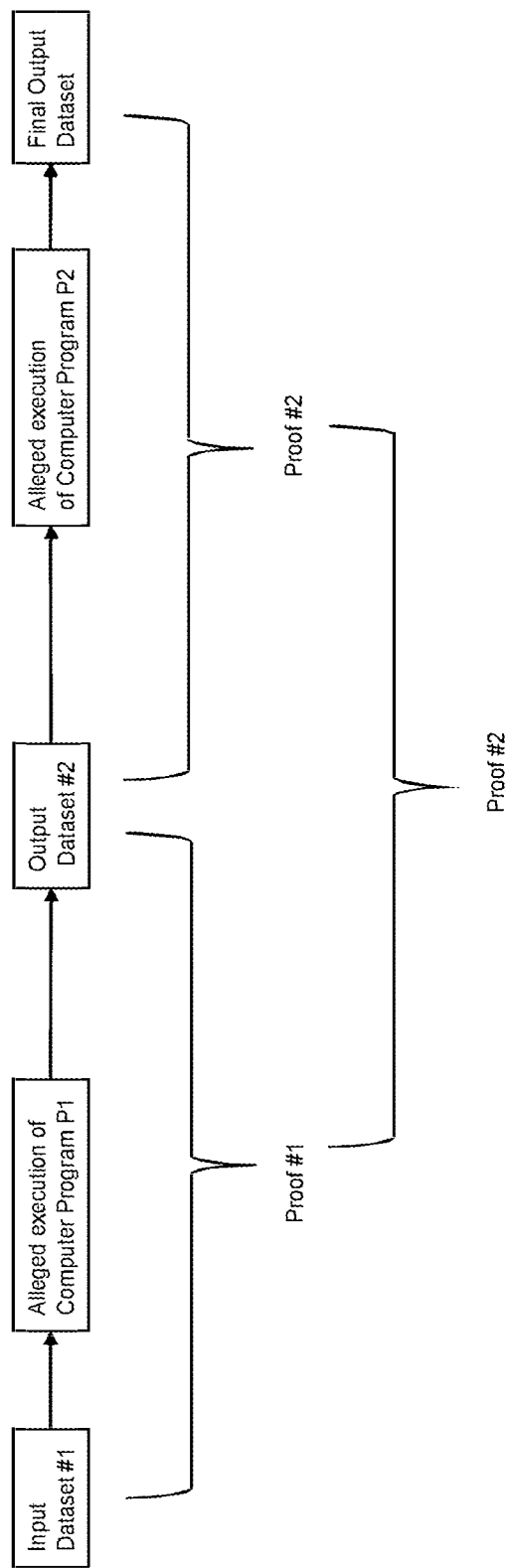
FIG. 5 is a simplified diagram of the use of technology to extend the chain of trust, i.e., the attestation or proofs associated with the federated pipeline of computations.

FIG. 5 illustrates this challenge. The data scientist, when sharing a result, wishes the recipient of the result to trust that a certain computer program (P1) that possibly may have been provided by the data scientist, was executed and that it accepted and verified the source of an input dataset (#1) provided by a federated pipeline with an attestation. Program P1, for example, may check a serial number provided as a part of dataset #1 against a known external data repository. The alleged execution of program P1 results in dataset #2.

Furthermore, the data scientist may wish that the recipient trust that dataset #2 was processed by a computer program P2 (that may have been provided by the data scientist) and the alleged execution of program P2 resulted in the Final Output Dataset (FIG. 5).

D. Genkin, et. al. "Privacy in Decentralized Cryptocurrencies," C. of the ACM, 2018, incorporated herein by reference in its entirety, illustrates exemplary techniques for verifying the execution of programs P1 and P2. A software module called the prover provides a computing environment in which the program P1 and P2 may be executed. Upon such executions, the prover produces two outputs: (1) the output of the programs P1 and P2, and (2) a data object called the proof of the execution of programs P1 and/or P2.

Figure 6:
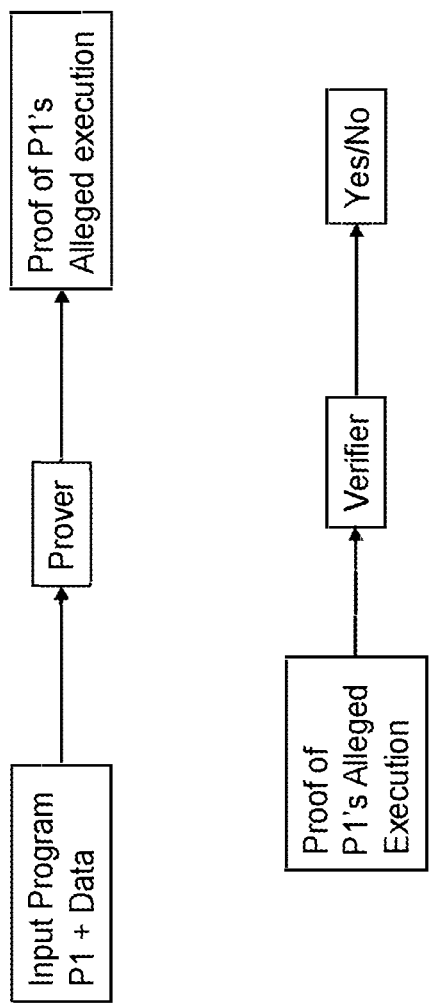
FIG. 6 is a simplified diagram of the verification of the extended chain of trust.

Additionally, the prover also provides a software module called the verifier (cf. FIG. 6) which may be provided to any third-party. The verifier takes a proof as input and outputs a binary "yes/no" answer. An answer "yes" signifies that the program under question was executed and produced the input proof object. A response "No" signifies that the proof of the alleged execution could not be verified.

Thus, D. Genkin, et. al. shows system and methods whereby alleged execution of computer programs may be verified by submitting the proofs of the alleged executions to a verifier system. The proof objects are cryptographic objects and do not leak information about the underlying data or the programs (other than the meta statement that the alleged execution is verifiable).

In embodiments, a computer program, P, may be agreed upon as incorporating a policy between two enterprises, $E_1$ and $E_2$. The former enterprise $E_1$ may now cause the program P to be executed and to produce a proof $\pi$ of its alleged execution using the above described prover technology. Enterprise $E_2$ may now verify $\pi$ (using the verifying technology described above) and trust that the program P was executed, thereby trusting that the agreed upon policy has been implemented.

Figure 1B:
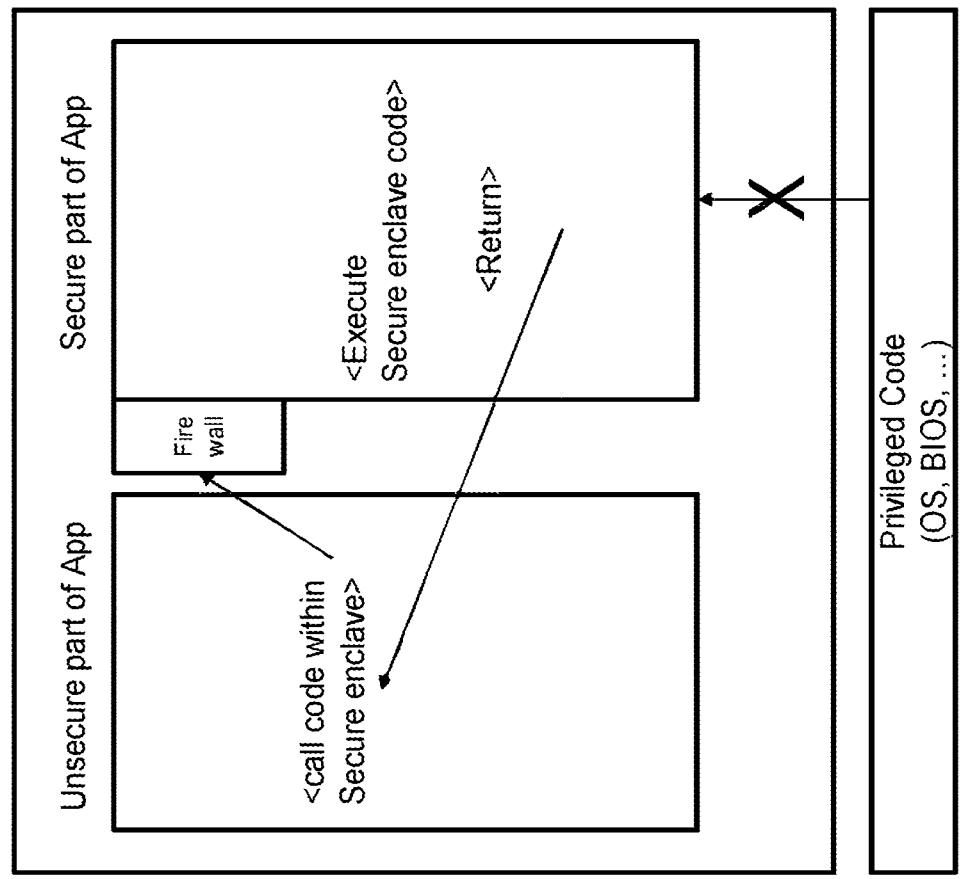
FIG. 1B is a simplified diagram of an architecture of a secure computing environment according to some embodiments.

FIG. 1B shows a logical architecture of a secure enclave from an application point of view. An application 100 contains its own code, data and secure enclave. Application 100 is logically split into two parts: (1) an unsecure part that runs as a typical application in a traditional computer, and (2) a secure part that runs in the secure enclave. The code in the unsecure part of the application can request that a secure enclave be created, a certain boot image be loaded into the secure enclave and executed. Control at the end of execution in the secure enclave is then returned back to the point of invocation. The privileged system 200 (comprising OS, BIOS, SMM, VM, etc.) is prevented from accessing the secure enclave.

In some embodiments, the following method may be performed to populate a secure enclave with code and data.
Method [Create and Populate Secure Enclave]
  (1) compile secure part of application;
  (2) issue command to create secure enclave (e.g., using underlying hardware/OS instruction set);
  (3) Load any pre-provisioned code from pre-specified libraries;
  (4) load the compiled code from step 1 into secure enclave;
  (5) generate appropriate credentials; and
  (6) save the image of the secure enclave and the credentials.

In some embodiments, the following method may be performed to execute the code in a secure enclave.
Method [Execute Code in Secure Enclave]
  (1) compile unsecure part of an application (e.g., application 100) along with the secure image;
  (2) execute the application;
  (3) the application creates the secure enclave and loads the image in the secure enclave; and
  (4) verify the various credentials.

The hardware and software components of a secure enclave provide data privacy by protecting the integrity and confidentiality of the code and data in the enclave. The entry and exit points are pre-defined at the time of compiling the application code. A secure enclave may send/receive encrypted data form its application and it can save encrypted data to disk. An enclave can access its application's memory, but the reverse is not true, i.e., the application cannot access an enclave's memory.

An enclave is a self-sufficient executable software that can be run on designated computers. For example, the enclave may include the resources (e.g., code libraries) that it uses during operation, rather than invoking external or shared resources. In some cases, hardware (e.g., a graphic processing unit or certain amount of memory) and operating system (e.g., Linux version 2.7 or Alpine Linux version 3.2) requirements may be specified for an enclave.

Figure 2:
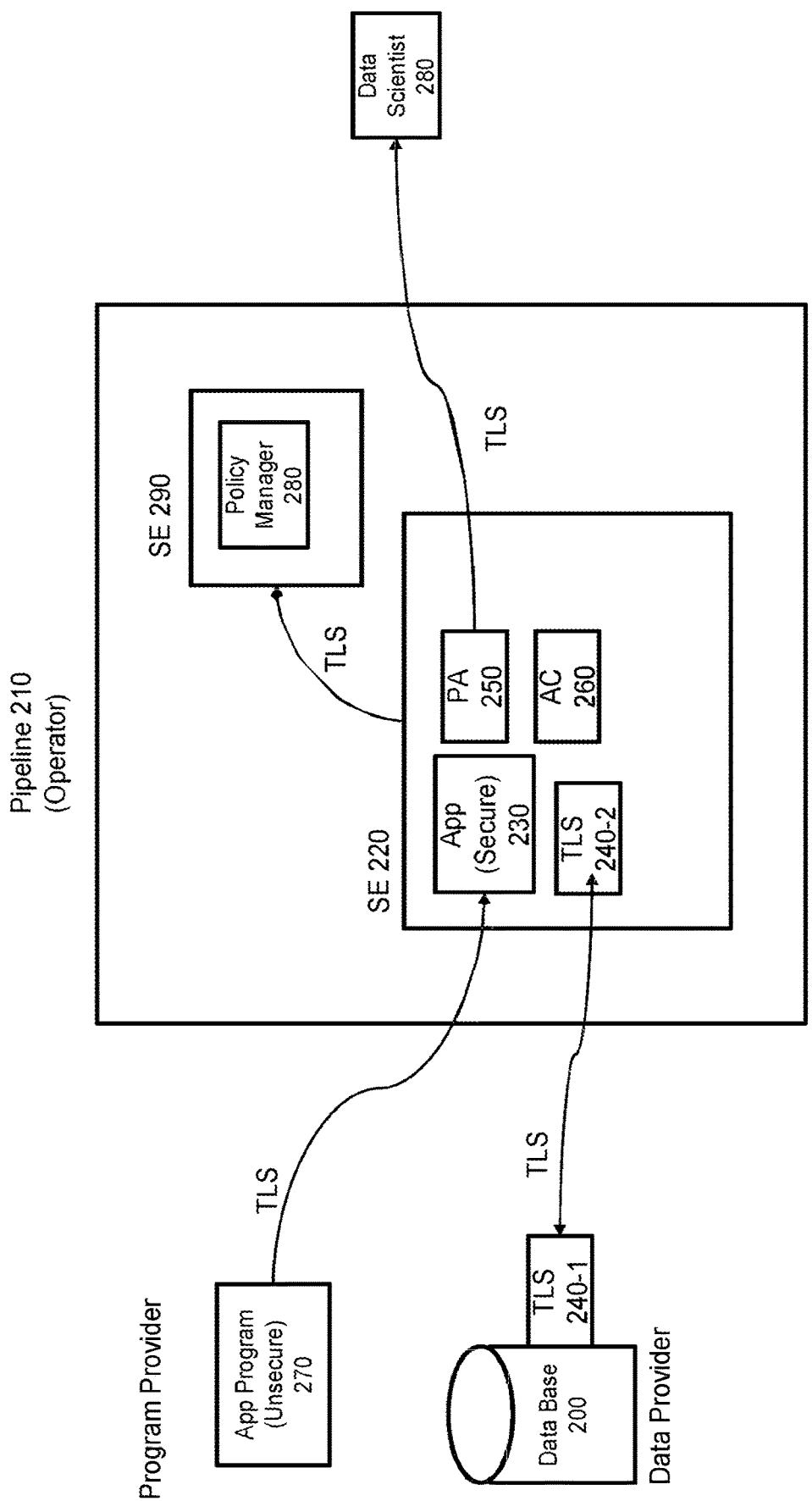
FIG. 2 is a simplified diagram of a general architecture of a secure enclave according to some embodiments.

FIG. 2 shows a use case scenario for processing healthcare data according to some embodiments. A data provider provides database 200 containing data records some of whose attributes may be private data, such as a user's name, address, patient ID number, zip code, and other user-specific data. Database 200 is connected to one or more computers collectively referred to as a pipeline 210, possibly residing in a cloud server environment.

FIG. 2 also shows a computer program 270 (provided by a program provider) that resides outside the enclave 220. This, as described earlier, is an unsecure program as it is not contained in a secure enclave. Using method "Create and Populate Secure Enclave," program 270 creates a secure enclave in pipeline 210 and populates it with its secure application part, App 230. Since App 230 is inside a secure enclave it is, by definition, secure.

As described in method "Create and Populate Secure Enclave," pre-provisioned software may also be loaded into a secure enclave. SE 220 contains, inter alia, pre-provisioned software 240-2 that acts as one endpoint for a TLS (Transport Level Security) connection. The second endpoint 240-1 for the TLS connection resides with the database 200. (Any secure network connection technology, e.g., https, VPN, etc., may be used in lieu of TLS.)

The TLS connection may be used by App 230 to retrieve data from database 200. App 230 may also include a proxy mechanism for executing receipt of data records.

Additionally, SE 220 contains pre-provisioned software modules PA 250 (Policy Agent) and AC 260 (Access Controller) whose functions are discussed below.

Program App 230 in SE 220 may thus retrieve data from database 200 using the TLS endpoints 240-1 and 240-2. TLS technology ensures that the data being transported is secure. Database 200 may contain encrypted data records. Thus, App 230 receives encrypted data records. In operation, App 230 decrypts the received data records and processes them according to its programmed logic. (The method by which decryption occurs is described later.)

Using method "Execute Code in Secure Enclave" described above, App 230 may be invoked which may then retrieve and decrypt data from database 200. The result of the processing is may be directed to an entity labelled data scientist 280 under control of the policy agent PA 250. Generally, PA 250 operates in conjunction with policy manager 280. The functioning and inter-operation of PA 250 and policy manager 280 will be described in more detail later.

In some embodiments, the policy manager 280 may exist in its own secure enclave 290.

FIG. 2 shows the pipeline containing 2 secure enclaves, 220 and 290. In embodiments, a pipeline may contain one or more secure enclaves. Furthermore, the one or more secure enclaves may be inter-connected (e.g., to distribute the computational work tasks). For example, the one or more secure enclaves may be inter-connected to achieve what is known as a map-reduce arrangement to achieve concurrent execution of computational tasks. A pipeline may be implemented using one or more computers, e.g., the secure enclaves may exist on multiple computers, e.g., in a cloud server environment. FIG. 2 shows a single database 200 connected to the enclave. In embodiments, one or more databases may be so connected to the one or more enclave(s).

In summary, a computational task may be achieved by encoding it as an application program with a secure and an unsecure part. When invoked, the unsecure part of the application creates one or more secure enclaves, injects its secure part into a secure enclave and invokes its execution. The secure part of the application may have access to data from (pre-provisioned) databases connected to the enclaves or from other enclaves. The secure part of the application then decrypts received data. Processing then proceeds as per the app's logic possibly utilizing the arrangement of the interconnected enclaves. The results are presented to the data scientist via the policy agent.

In comparison to the FHE dataset approach, in which the data is never decrypted and processing proceeds on encrypted data, in the arrangement shown in FIG. 2, the data inside an enclave is in encrypted form and is decrypted before processing. It may be re-encrypted before the results are shared with external entities. The arrangement of FIG. 2 may therefore be more efficient and achieve an improved speed of processing relative to FHE.

The pipeline technology described above allows computations to be carried out on datasets that may contain private and personal data. An aspect of pipeline technology is that data (and programs) inside a secure enclave are inscrutable, i.e., subject to policy control exercised by the policy manager (or its cohort, the policy agent). Furthermore, the outputs produced as a consequence of the execution of the program, may be directed according to policies also.

As an illustration, consider a computation carried out in a pipeline that calculates the body mass index (BMI) of individual patients stored in a dataset containing, inter alia, their weights, heights, date of births and addresses. The computation then proceeds to calculate the average BMI across various US counties.

Since these calculations involve private and personal patient data, the computations may be subject to privacy regulations. Various types of outputs may be desired, such as the following illustrative examples: (1) a dataset of 5 US counties that have the highest average BMI; (2) a dataset of 5 patients with street addresses with "overweight" BMI; (3) a dataset of patients containing their zip codes and BMI from Norfolk county, MA; (4) a dataset of patients with "overweight" BMI between the ages of 25-45 years from Dedham, Mass.; or (5) a dataset of patients containing their weight, height and age from Allied Street, Dedham Mass. In each case, the input to the computation is a dataset that may contain private and personal data and the output is a dataset that may also contain private and personal data.

The first output dataset above lists data aggregated to the level of county populations and does not contain PII data attributes. The result is independent of any single individual's data record; the result pertains to a population. A policy may therefore provide that such a dataset may be outputted, i.e., as plaintext.

On the other hand, the second outputted dataset above (1) contains personal identifiable information, i.e., street address, and (2) the number of items in the dataset, i.e., the cardinality of the output set, is small. A malicious agent may be able to isolate particular individuals from such a dataset. In this case, a policy may be formed to disallow such requests.

That is, a parameter, K, called the privacy parameter, may be provided that imposes a bound on the cardinality of the outputted datasets. Thus, an outputted dataset may be disallowed if its PII attributes identify less than K individuals.

Additionally, or alternatively, the output dataset may be provided in encrypted form inside a secure enclave to the intended recipient, e.g., the data scientist along with a computer program responsive to queries submitted by the data scientist. The latter may then use an (unsecure) application program to query the (secure) program inside the enclave and receive the latter's responses. Thus, the data scientist may not see the patient data but can receive the responses to his queries. Furthermore, the responses of the secure program may be constrained to reveal only selected and pre-determined "views" the output dataset, where the "views" may correspond to the generally accepted notions of views in database system. Alternatively, the output dataset may also be provided to the data scientist without enclosing it in a secure enclave by first encrypting the dataset using FHE.

In the third output request above, the data is being aggregated across zip codes of a county and therefore may not engender privacy concerns, provided that the number of such patients is large enough. In such examples, a policy may be formed that imposes a constraint on the size of the output dataset, e.g., output dataset must contain data pertaining to at least 20 patients. Similar policies may also be used for the fourth and fifth output requests.

In some embodiments, a policy may be formed that provides for adding random data records to an outputted dataset if the cardinality of the dataset is less than the imposed constrained limit. That is, a constraint is imposed such that enough records are included in the output dataset to achieve an output of a minimum size, e.g., 20 individuals.

Further challenges may arise when output requests (e.g., the third, fourth and fifth output requests above) are issued as a series of requests and the outputs are collected by a single entity (e.g., a data scientist) or multiple entities that collude to share the outputs. Since the output requests compute datasets that successively apply to smaller population sizes, there is a possibility that such "narrowing" computations may be used to gain information about specific individuals.

It has been shown in the literature (cf. Cynthia Dwork, *Differential Privacy: A Survey of Results*, International Conference on Theory and Applications of Models of Computation, 2008) that sequences of ever-increasing narrowing (or more accurate responses) ultimately leaks individual information.

FIG. 3 shows the various policies discussed above. These policies are intended for illustrative purposes, actual policies that are implemented may be different.

In some embodiments, a policy agent may be configured so as to be included as a pre-provisioned software in one or more secure enclaves of a pipeline. The policy agent receives its policies from a Policy Manager (described below) and imposes its policies, some examples of which have been provided in the discussion above, on every outputted dataset. Out of band agreements between various (business) parties may be used to allow parties to specify and view the pre-provisioned policies contained in a policy agent.

Policy agent software also records, i.e., logs, all accesses and other actions taken by the programs executing within an enclave.

A Policy Manager may be configured to manage one or more policy agents. The Policy Manager may also perform other functions which will be described below. For simplicity, the present disclosure illustrates a single Policy Manager for a pipeline managing all policy agents in the pipeline in a master-slave arrangement.

The present disclosure also shows a Policy Manager running in the domain of the Operator of the pipeline for illustrative purposes, and various alternatives are possible. In some embodiments, the Policy Manager may be implemented in any domain controlled by either the operator, data provider, program provider or data scientist. If the Policy Manager is implemented using decentralized technology, the control of the Policy Manager can be decentralized across one or more of the above business entities. The term "decentralized" as used in this disclosure implies that the policies that control a policy manager may be provided by multiple parties and not by any single party.

For example, FIG. 7 shows one illustrative embodiment of a decentralized control of a policy manager. FIG. 7 shows a table contained in the policy manager whose rows describe groups. A group is a collection of collaborating entities and the elements related to their collaboration. The group of collaborating entities exercise control of the policy manager via their individual policies. The first row shows a group named Group 1 which has entity named A1 as a member providing an algorithm a1, another member named D1 providing data d1. The data and algorithm provided by the two members has been processed and a load image has been readied to be loaded into a pipeline. The readied load image is stored in secure storage and may be accessed by using link L1.

In some embodiments, a policy agent may record its state with the Policy Manager. Additionally, the Policy Manager may be architected to allow regulators and/or third-party entities to examine the recorded state of the individual Policy Agents. Thus, regulators and third-party entities may examine the constraints under which datasets have been outputted. In embodiments, a possible implementation method for the Policy Manager is as a block-chain system whose ledgers may then contain immutable data records.

In scenarios discussed above, a policy may dictate that a data scientist may receive an outputted dataset enclosed in a secure enclave. This means that the data in the dataset is non-transparent to the data scientist. The latter is free to run additional output requests on the outputted dataset in the enclave by injecting new requests into the enclave. In those cases, when the outputted dataset does not have any PII data or does not violate the privacy parameter constraint, the dataset may become unconstrained and may be made available to the data scientist.

In some embodiments, a data scientist or other requestor may view the contents of a dataset contained within an enclave. The contents of an enclave may be made available to a requestor by connecting the enclave to a web browser and causing the contents of the enclave to be displayed as a web page. This prevents the requestor from saving or copying the state of browser. However, in some cases, the requestor may take a visual image of the browser page.

In some embodiments, a data scientist may submit data requests, which are then curated using a curation service. If the curation service deems the data requests to be privacy-preserving, then the data requests may be processed using the dataset in the enclave and the outputted dataset may be provided to the data scientist as an unconstrained dataset. In this manner, the curation service checks and ensures that the submitted data requests are benign, i.e., that the data requests do not produce outputs that violate privacy regulations.

As discussed above, a further challenge associated with processing private data using enclaves is whether policies can be provided about the computations carried out within the enclave, since the processes internal to an enclave are inscrutable. Consider, for example, a use case of secure enclave technologies, following the general description above with respect to FIG. 2. A first enterprise possessing encrypted data may store the data in an enclave. The data in the enclave may be processed and readied for use by a second enterprise providing the pipeline, the computer program processing the data being provided by a third enterprise. A data scientist may now inject a data request into the enclave and expect an outputted dataset as a result. As explained above, in one instance, the outputted data set may be provided to the data scientist as data enclosed in an enclave. In another instance the outputted dataset may be provided as an encrypted store of data. In the latter case, the data scientist may be provided a decryption key so as to provide him/her access to the data. All these actions are subject to the policies determined a priori by either the first, second or third enterprise.

Furthermore, the policy in question may require that the access to process the data and receive the outputted dataset by the data scientist must be authorized. That is, the access by the data scientist must be authenticated. Data scientists on their part may require that they be assured that their data requests operate on data provided by a specified data provider since the integrity of data is crucial to the data processing paradigm. In particular, if the data scientist intends to share the outputted results with a third party, the data scientist may need to assure the former of the integrity of the input data and the fact that the results were obtained by executing a particular data request. Regulators may require that the entire process of storing and processing the data must be transparent and to be made available for investigations and ex post facto approval.

Figure 4A:
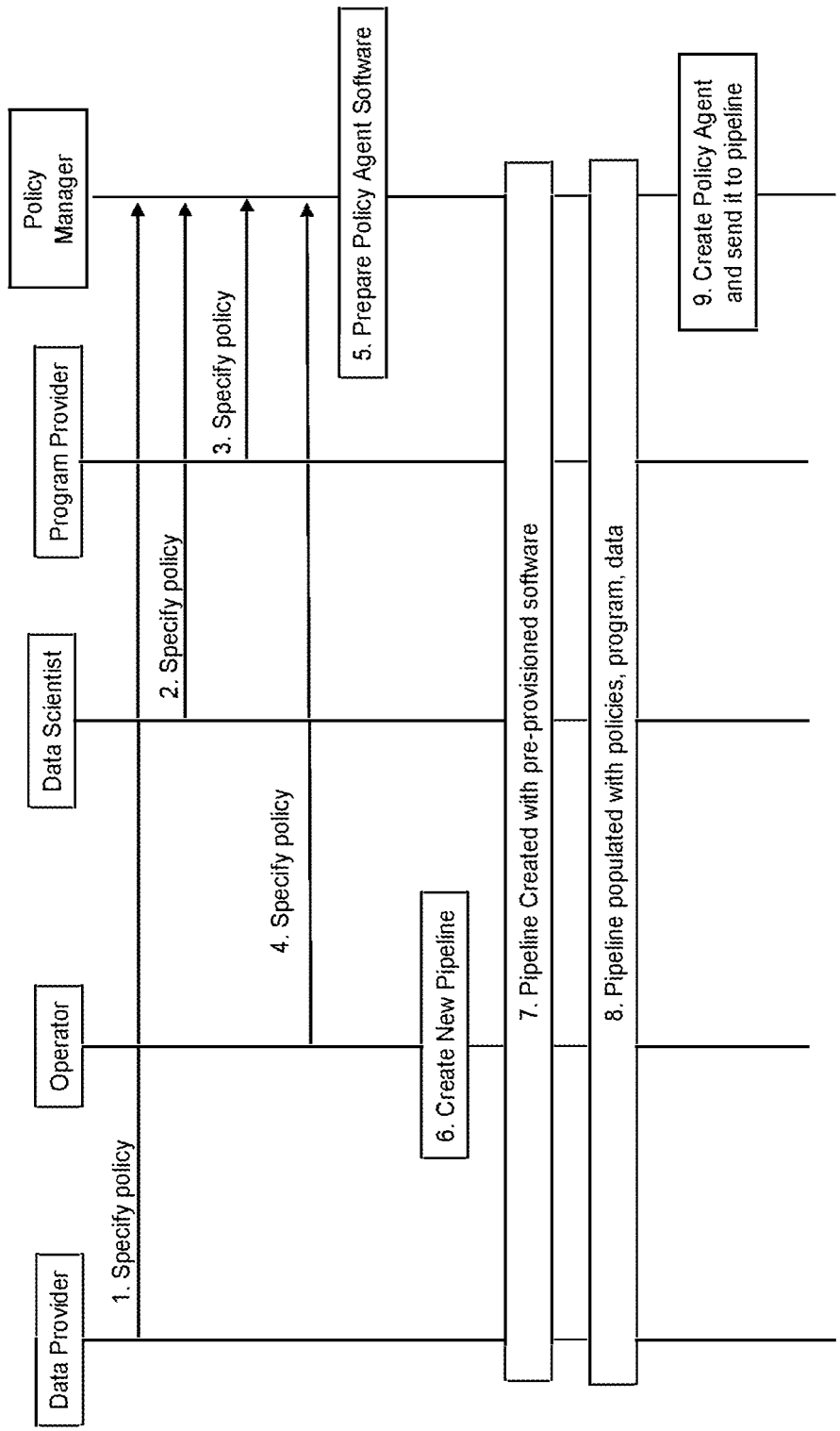
FIG. 4A is a simplified diagram of an illustrative orchestration to ensure that policies are properly programmed in secure enclaves.

To address the various concerns stated above, an orchestration method may be performed as shown in a workflow diagram in FIG. 4A. The following entities are involved in the workflow: (1) data provider, i.e., the entity that owns data; (2) operator, i.e., the entity that provides pipeline technology; (3) a program provider that provides the computer program to process data; (4) data scientist, i.e., an entity that wishes to obtain outputted results; and (5) policy manager, which may include a software module controlling the policy agent.

Referring to FIG. 4A, in step 1, 2, 3 and 4 the data provider, the data scientist, the program provider and the operator respectively specify their policies. In step 5 the Policy Manager prepares to initiate the Policy Agent. In step 6, the operator creates a new pipeline and, in step 7, informs the participants in the orchestration about the creation of the pipeline. The participants may now populate the pipeline with data, programs, and policies. Note that the pipeline is initiated also with pre-provisioned software libraries.

Figure 4B:
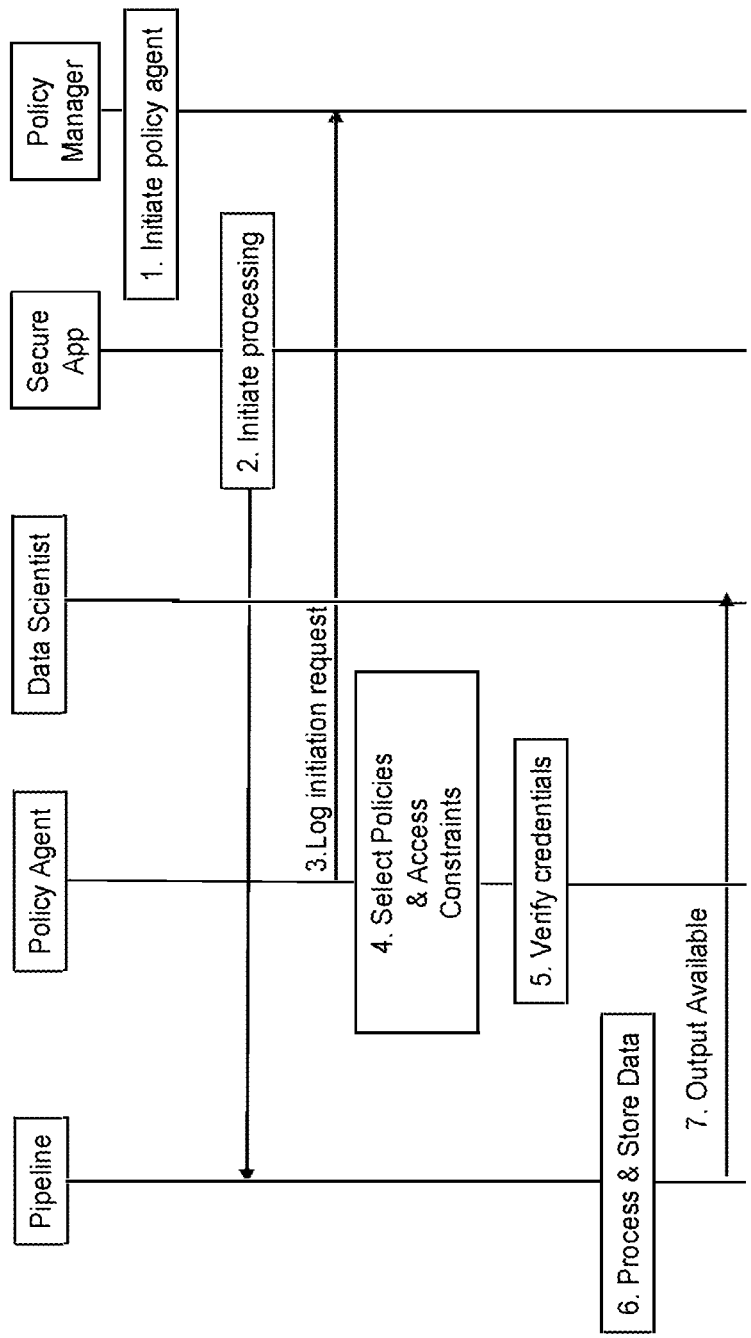
FIG. 4B is a simplified diagram of an illustrative orchestration to ensure that data is computed subject to policy constraints.

Referring to FIG. 4B shows the orchestration between a data provider, a pipeline, a secure application program provided by a program provider, a policy manager, a data scientist and a policy agent.

Step 1. The policy manager initiates the policy agent that it had prepared in step 5 of FIG. 4A.

Step 2. Secure application initiates a processing request.

Step 3. Logs the initiation request.

Step 4. Policy agent selects appropriate policies and access credentials related to the processing request.

Step 5. Policy agent (with help of policy manager) verifies credentials. If the credentials are not satisfied, the request is terminated.

Step 6. Pipeline executes the processing request and stores the data.

Step 7. Pipeline notifies data scientist that the requested output is available.

Key Management

Public key cryptography relies on a pair of complementary keys typically called the private and public keys. The latter may be distributed to any interested party. The former, i.e., the private key, is always kept secret. Using the public key distributed by, say Alice, another party, say Bob, may encrypt a message and send it to Alice safe in the knowledge that only Alice can decrypt the message by using her private key. No other key can be used to decrypt the message encrypted by Bob. As mentioned before, ownership of a private key is a major concern and several techniques are discussed in literature relevant to this topic.

Secure enclave technology may be used to address the private key ownership issue by ensuring that the private key (corresponding to a public key) always resides in a secure enclave. This may be accomplished, for instance, by creating a first secure enclave and pre-provisioning it with public/private key cryptography software that creates pairs of private and public keys. Such software is available through opensource repositories. A computer program residing in a second secure enclave may then request the first enclave to provide it (using a secure channel) a copy of the private key that it needs. Thus, the private key never exists outside the secure enclave infrastructure, always residing in secure enclaves and being transmitted between the same using secure channels.

In some embodiments, a policy manager may be pre-provisioned with public/private key software and the Policy Manager be enclosed in a secure enclave as shown in FIG. 2 (cf. 280).

A secure enclave may then request its policy agent for a private key. The policy agent, as discussed above, operates in conjunction with the policy manager and may request the same from its policy manager. A computer program executing in a secure enclave may need a private key to decrypt the encrypted data it may receive from a data provider. It may request its policy agent who may then provide it the needed private key for decryption purposes.

As explained earlier, encryption technologies referred to as hash functions or hashing algorithms exist that can take a string of cleartext, often called a message, and encrypt it as a sequence of hexadecimal digits, i.e., sequence of digits [0-9, A-F]. Examples of publicly available hash functions are MD5, SHA-256, SHA-512. The latter two functions use keys of length 256 and 512, respectively. As discussed above, the length of the keys is a factor in ensuring the strength of an encryption technology to withstand malicious attacks.

One property of hash functions that map cleartext into hexadecimal digits is that they do not map different cleartexts to the same digits. Thus, a piece of cleartext may have a unique signature, i.e., the output of the hash function operating on the cleartext as input.

If a secure enclave containing programs and data can be viewed as comprising cleartext then it follows that every secure enclave has a unique signature. Thus, by applying a suitable hash function to the contents of a secure enclave, a signature of that enclave is obtained. The signature is unique in that no other and different secure enclave will have that signature.

If a secure enclave is populated with a known computer program and a known dataset then that secure enclave's signature may be used to assert that the secure enclave is executing (or executed) the program on the known dataset by comparing the signature of a secure enclave with previously stored signatures.

Thus, a data provider, if provided with a signature of the enclave, may be assured that its dataset is uncorrupted or unchanged and is operated upon by a pre-determined program.

Similarly, a program provider may be assured that its programs are uncorrupted and unchanged. A data scientist may be assured that its output is the result of processing by the pre-determined program on pre-determined data.

Since a policy manager may be programmed to disallow the operator to access the contents of a secure enclave by denying access to the relevant decryption keys, the operator of the pipeline cannot view or edit the contents of the secure enclave.

In the present disclosure, secure enclaves may be pre-provisioned with software to compute hash functions that may be invoked by the policy manager to create signatures. The policy manager may then be programmed to provide these signatures as certificates upon request to various entities, e.g., to the data provider or the program provider.

Figure 10:
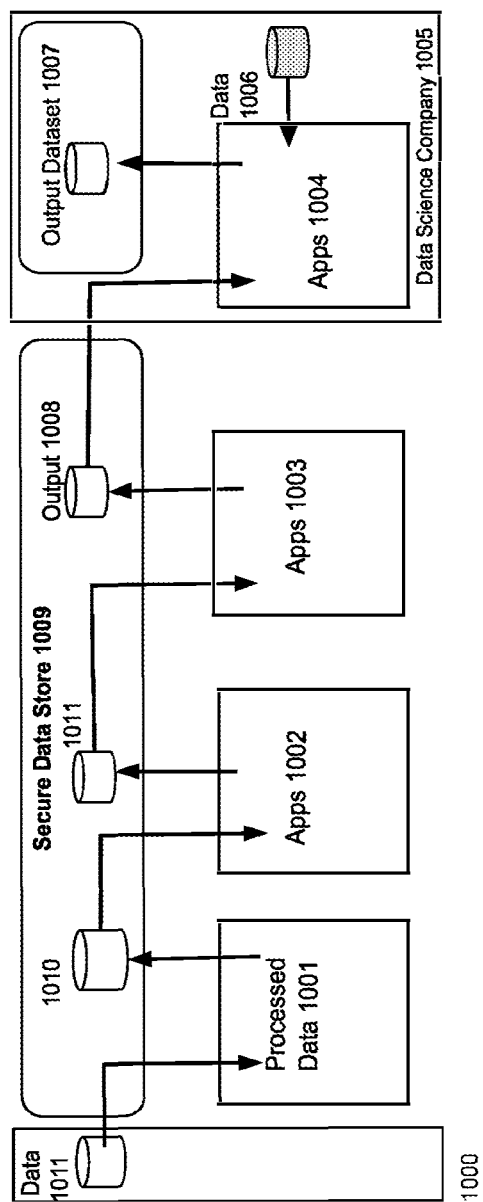
FIG. 10 is a simplified diagram of an architecture of a federated group of enterprises collaboratively receiving, storing and processing private data according to some embodiments.

Referring now to FIG. 10, an initial dataset 1001 may be stored in a secure enclave 1001 where it may be processed and outputted as dataset 1010. Dataset 1010 exists in a secure data layer 1009. One or more apps may be injected by data scientists into enclave 1002 and the dataset 1010 may be provided to such apps. Upon processing, the outputted dataset may be stored as output 1008. The latter may be further injected into enclave 1004 where an enterprise 1005 may use (proprietary) apps to process and output the result as dataset 1007. Note that output dataset 1007 is encrypted.

Thus, enterprise 1005 has a choice to run apps injected into enclave 1003 or to receive the dataset 1008 into a different enclave 1004 and run their proprietary apps therein.

That is, a series of enclaves 1001, 1002, 1003 and 1004 (FIG. 10) may be assembled wherein each enclave receives encrypted data from a secure data store 1009 and produces a secure (encrypted) dataset in turn for the next in line enclave. Thus, the original data owner 1000 may provide its data 1011 for processing to a third party, i.e., enterprise 1005 and be assured that no private or personal data may leak.

Enterprise 1005 has the flexibility to run its own data requests on the datasets and provide the results of the processing to its customers, along with certificates that the appropriate data requesting programs were executed and the provenance of the input data was ascertained. Enterprise 1005 may assume ownership of the dataset 1007 but then it assumes legal responsibility for its privacy.

Figure 9:
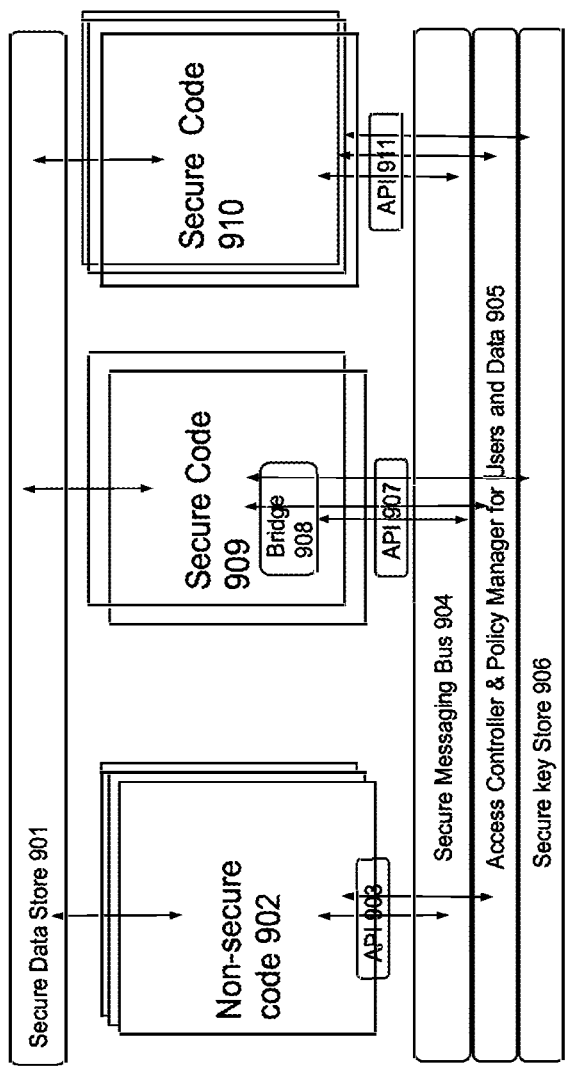
FIG. 9 is a simplified diagram of an architecture of a federated group of enterprises collaboratively receiving, storing and processing private data according to some embodiments.

FIG. 10 shows a sequence of enclaves, each enclave being connected to another enclave via an intermediate secure data layer. However, in embodiments, as shown in FIG. 9, several enclaves 909 and also 910 may be executing in a concurrent manner. Furthermore, not all code may reside in enclaves, enclaves may be mixed with computing environments that contain non-secure code as needed, cf. 902 (FIG. 9).

Along with the secure data layer available to all enclaves, additional layers may be provided for secure messaging 904, access control and policy agent communication 905 and exchange of cryptographic keys 906. These additional communication layers are provided so that enclaves may exchange various kinds of data securely and without leaks with each other.

Figure 8:
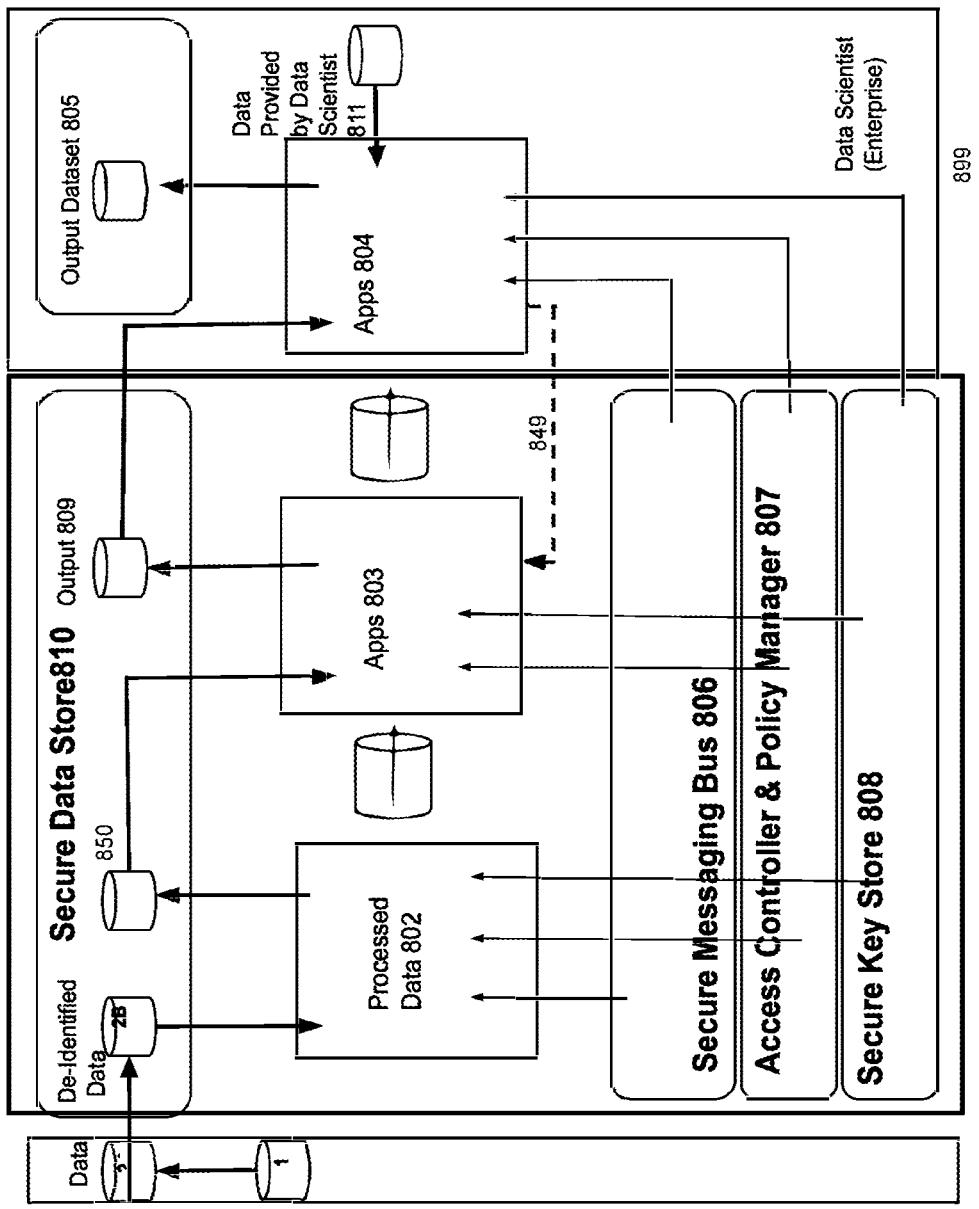
FIG. 8 is a simplified diagram of an architecture of a federated group of enterprises collaboratively receiving, storing and processing private data according to some embodiments.

Referring to the illustrative embodiment shown in FIG. 8, a first enterprise 800 owns dataset 1 which it may de-identify and anonymize to get dataset 2A. As discussed before, the de-dentification procedures may not be completely effective and the dataset 2A may still contain some private and personal data. The first enterprise provides a copy of dataset 2A, shown as 2B, in a secure data layer 810 so that it may be made available for processing by a second enterprise, 890.

Enterprise 890 receives the dataset 2B and causes it to be stored in enclave 802 where it may be processed and readied for further processing, whereupon it is stored in the secure data layer 810 as dataset 850.

Enclave 802 is pipelined to enclave 803 which implies that the dataset 850 is outputted from enclave 802 and provided as input to enclave 803. The apps in enclave 803 may now process the data and produce as output dataset 809.

In turn, enclave 803 is pipelined to enclave 804 which exists in a network administered by enterprise 899. That is, enclave 803 is administered by enterprise 890 and enclave 804 is administered by enterprise 899. The latter enterprise may inject additional data 811 into enclave 804, and also inject apps to process the dataset 811 in conjunction with input dataset 809, to produce dataset 805. The result of the computation may be made accessible to a data scientist at enterprise 899 as per the dictates of the policy agent/manager.

FIG. 8 also shows an illustrative embodiment 849 in which enterprise 899 may contribute data from enclave 804 (possibly obtained as a result of processing) to be injected into enclave 803. This allows obtained results to be re-introduced for further processing, i.e., allowing feedback loops for further processing of results.

In the foregoing discussion, various embodiments have shown system and methods for collaborative storing, processing and analyzing of data by multiple parties. For example, FIG. 8 shows three enterprises 800, 890 and 899 that collaborate. Enterprise 800 provides data, enterprise 890 provides the infrastructure that stores the data in an enclave and enterprise 899 processes the data by injecting specific data requests into the enclave. In one embodiment, a central trust model is used in which one of the enterprises, e.g., the enterprise that provides the infrastructure, is trusted to ensure that data provided by a first enterprise is made available to a second enterprise under a collaborative agreement. That is, the trusted enterprise ensures that data access and data processing obey the various ownership and processing concerns. Data providers would like to be ensured that their data is only processed by approved enterprises. Data processing people would prefer that their data requests be kept private and the details of their processing requests not be shared with competitors. Maintenance of such concerns can be reposed in the trusted enterprise. Such an embodiment may be referred to as a centralized trust model, i.e., trust is placed in one enterprise or entity.

In another embodiment, a decentralized trust model may be provided in which multiple enterprises are trusted. Such a trust model may be particularly apt in an open marketplace where data providers contribute data and analyzers contribute data requests, i.e., computer programs, that process the contributed data. No single enterprise or entity is to be trusted in the decentralized model. Rather an openly available structure is provided that any third party may access to verify that the constraints governing the data and algorithm providers are being maintained.

FIG. 7 shows one illustrative embodiment of a decentralized trust model. FIG. 7 shows a table whose rows describe groups. A group is a collection of collaborating entities and the elements related to their collaboration. The first row shows a group named Group 1 which has entity named A1 as a member providing a program a1, another member named D1 providing data d1. The data and algorithm provided by the two members has been processed and a load image has been readied to be loaded into an enclave. The readied load image is stored in secure storage and may be accessed by using link L1.

As explained above, in order to load the image into an enclave, a specific encryption key is needed to encrypt the data (whose corresponding decryption key will be used by the enclave to decrypt the data).

It is to be understood that the foregoing embodiments are illustrative, and that many additional and alternative embodiments are possible. In some embodiments, at least a portion of the federated pipeline described above may be run on hardware and firmware that provides protected memory, such as Intel Security Guard Extensions (SGX), the implementation details of which are described at https://www.intel.com/content/www/us/en/architecture-and-technology/software-guard-extensions.html. In some embodiments, at least a portion of the federated pipeline may be run using virtualization software that creates isolated virtual machines, such as AMD Secure Encrypted Virtualization (SEV), the implementation details of which are described at https://developer.amd.com/sev/. In some embodiments, the federated pipeline may manage cryptographic keys using a key management service, such as the Amazon AWS Key Management Service (KMS), which described in further detail at a https://aws.amazon.com/kms/. However, these examples of hardware, firmware, virtualization software, and key management services may not independently create isolated software processes that are based on cryptographic protocols which can be used to create federated pipelines that have different ownerships, policies and attestations. Accordingly, in some embodiments, middleware (e.g., a layer of software) may be provided that can use underlying hardware/firmware, operating system, key management and cryptographic algorithms to achieve secure and private isolated processes, such as secure enclaves.

In some embodiments, secure enclaves can be linked together to form pipelines. Consistent with such embodiments, computations can be broken into sub-tasks that are then processed in pipelines, either concurrently or sequentially or both based on the arrangement of the pipelines.

In some embodiments, an attestation service can be associated with a pipeline. The attestation service establishes a chain of trust that originates from the start of the pipeline to the end of the pipeline, which provides external entities assurances even though the internal contents of a pipeline may not be observable to external entities. In some embodiments, the chain of trust can be further extended without extending the associated pipeline itself.

One way of dealing with healthcare data is to anonymize or mask the private data attributes, e.g., mask social security numbers before it is processed or analyzed. In some embodiments of the present disclosures, methods may be employed for masking and de-identifying personal information from healthcare records. Using these methods, a dataset containing healthcare records may have various portions of its data attributes masked or de-identified. The resulting dataset thus may not contain any personal or private information that can identify one or more specific individuals.

However, given the nature of healthcare records, it may not be possible to completely anonymize or de-identify a healthcare dataset. For example, a dataset may contain contemporaneous (hand-written) notes taken by a healthcare provider that are then digitally transcribed. Many healthcare datasets are obtained by digitizing analog data, e.g., pathology data. Thus, a dataset, particularly if it contains a large number of records, may contain private and personal information that is not anonymized or de-identified.

Information masking in text, for certain application domains, demands a very high level of performance, particularly recall (a ratio between the number of sensitive entities tagged by a model and the total number of sensitive entities). For instance, masking patient identity information—such as name, location, phone, address, etc.—in electronic health records (EHR) to publish them for research purposes, requires very high levels of recall in order for EHR records to be released for research. The adoption of EHR has skyrocketed in US hospitals and medical research centers from 9% (2008) to 96% (2017). Clinical trials data sets represent just a tiny fraction of the real world evidence data of which EHRs are a part—approximately 1 million patients have been treated per Big Pharma since 2003 in approximately 3,490 interventional clinical trials per Big Pharma since 2003. Through this lens, synthesizing health care provider proprietary EHR data sets (unstructured and structured data) across all the major US and world healthcare organizations will emerge as the modern kernel of research and development (R&D) data sciences, replacing the current reliance on clinical trial data sets and purely structured EHR/claims databases. If done properly, curated EHR data can become a key asset for biopharma companies as it can significantly enhance/augment the clinical data used for R&D purposes and even provide an alternative way for biopharma companies to demonstrate to regulatory agencies (such as FDA) that their drugs are effective in the real world such that they can get additional approvals and line extensions without having to run additional clinical trials.

However, there are several challenges related to the generation of such robust "clinico-genomic" datasets. For a start, data ownership and data de-identification are two of these challenges. Identifiable patient information from EHR data is owned by the patients, but the de-identified patient-level data can be synthesized and commercialized. The institutions (hospitals etc.) are the current "owners" or "custodians" of de-identified EHR data, so they have the maximum control/leverage over that data—provided the de-identification process is done in a robust manner. The latter is a complex task when dealing with "deep EHR data" since personal information is ubiquitous (in clinical notes, pathology reports, etc.), and further since that personal information is available in highly diverse ways.

Processes for de-identification require that words, phrases, or numbers that are flagged as Patient Health Information ("PHI") are replaced by non-identifiable placeholders that do not place patient privacy or confidentiality at risk. An example of these requirements are those outlined in the Safe Harbor Method defined by the United States HIPAA Privacy Rule, section 164.514, incorporated in its entirety herein by reference in its entirety, which specifies eighteen categories of PHI identifiers that must be masked. The Safe Harbor Method also includes associated guidelines, also incorporated in its entirety herein by reference in its entirety, to inform operators on how best to implement the requirements contained in the Privacy Rule for the de-identification of health information. Although discussions of some embodiments below are directed to patient data typically masked in accordance with the Safe Harbor Method, the systems and methods described herein may equally apply to data records beyond these embodiments.

Current deep learning models for NLP (Natural Language Processing) do not, on their own accord, meet these high standards of performance required for this application. One of the reasons they do not meet these standards is the fact that these models require large amounts of labeled data for supervised learning. Publicly available labeled data for certain entity types can be leveraged off in some cases, but sufficient domain specific labeled data is often required in practice for these models to reach the high levels of recall that is necessary. While precision is not the primary objective from a masking perspective, for the masked data to be of any material use for research, precision has to be high. Requirements for effectiveness are high for both precision and recall, with recall typically being higher (e.g., the minimum acceptable precision may be 99.999% or more).

Large scale masking of entities revealing sensitive information is not limited to EHR applications. For example, the release of documents containing sensitive information by any government agency has the same problem to grapple with even though it is often solved in practice by human curation at small scales.

Dictionary based methods prior to deep learning models fall even shorter, requiring human curation/verification, making large scale masking applications nearly impractical due to scale The present disclosure may address one or more of these limitations as described below.

Figure 11:
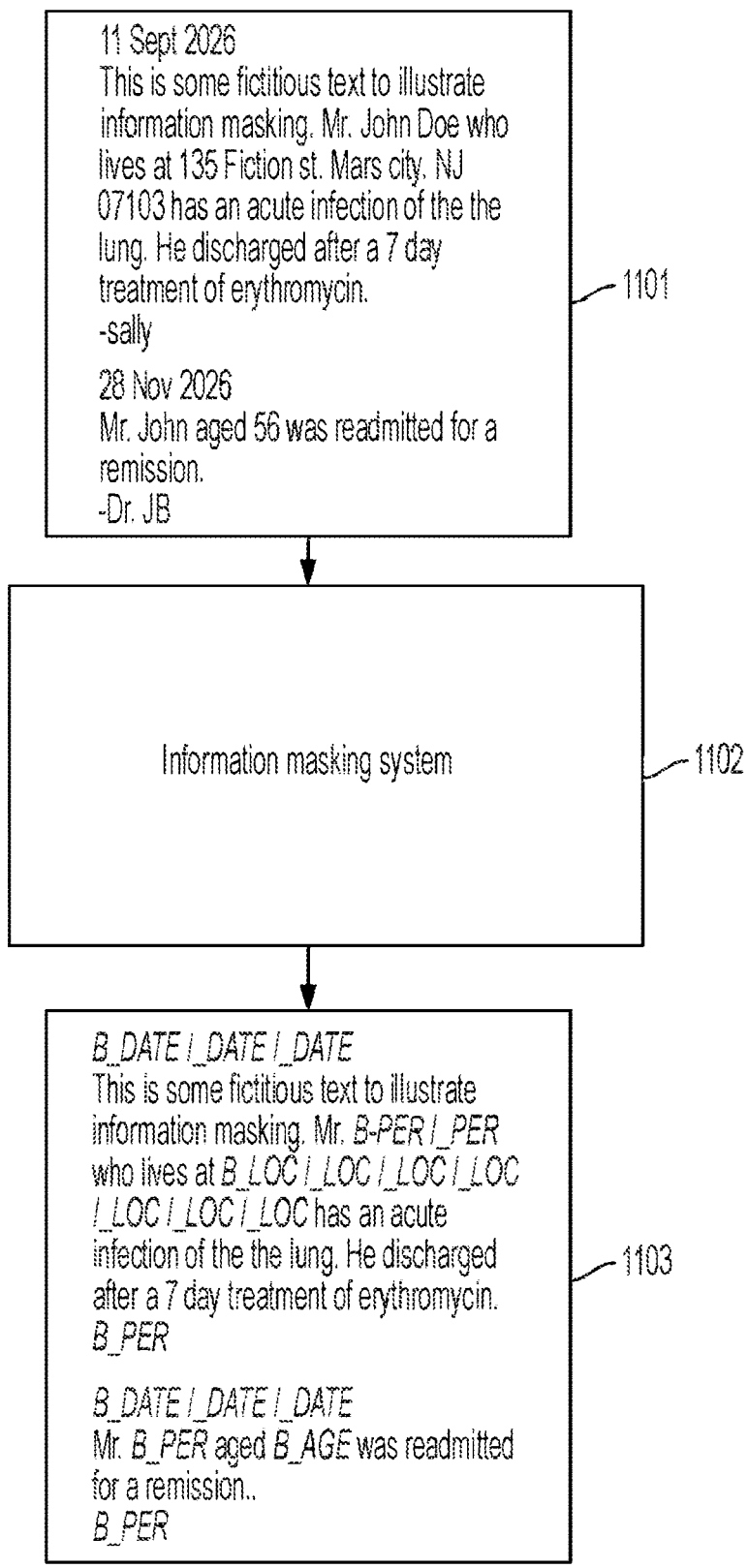
FIG. 11 is a simplified diagram of a system for information masking according to some embodiments.

FIG. 11 is a simplified diagram of a system for information masking according to some embodiments. Once the system has been trained to selectively mask information, a text input 1101 that is fed to the system 1102 will result in an output 1103 where subset of entities of interest, that are either single words or multi word phrases will be selectively masked (replaced with a generic placeholder token). In the example shown in FIG. 11, four entity types are masked—person, location, date, and age. Text input 1101 may represent portions of a corpus of EHR pulled from a third party record database, such as EPIC or Cerner, among other repositories of text-based information.

Figure 12:
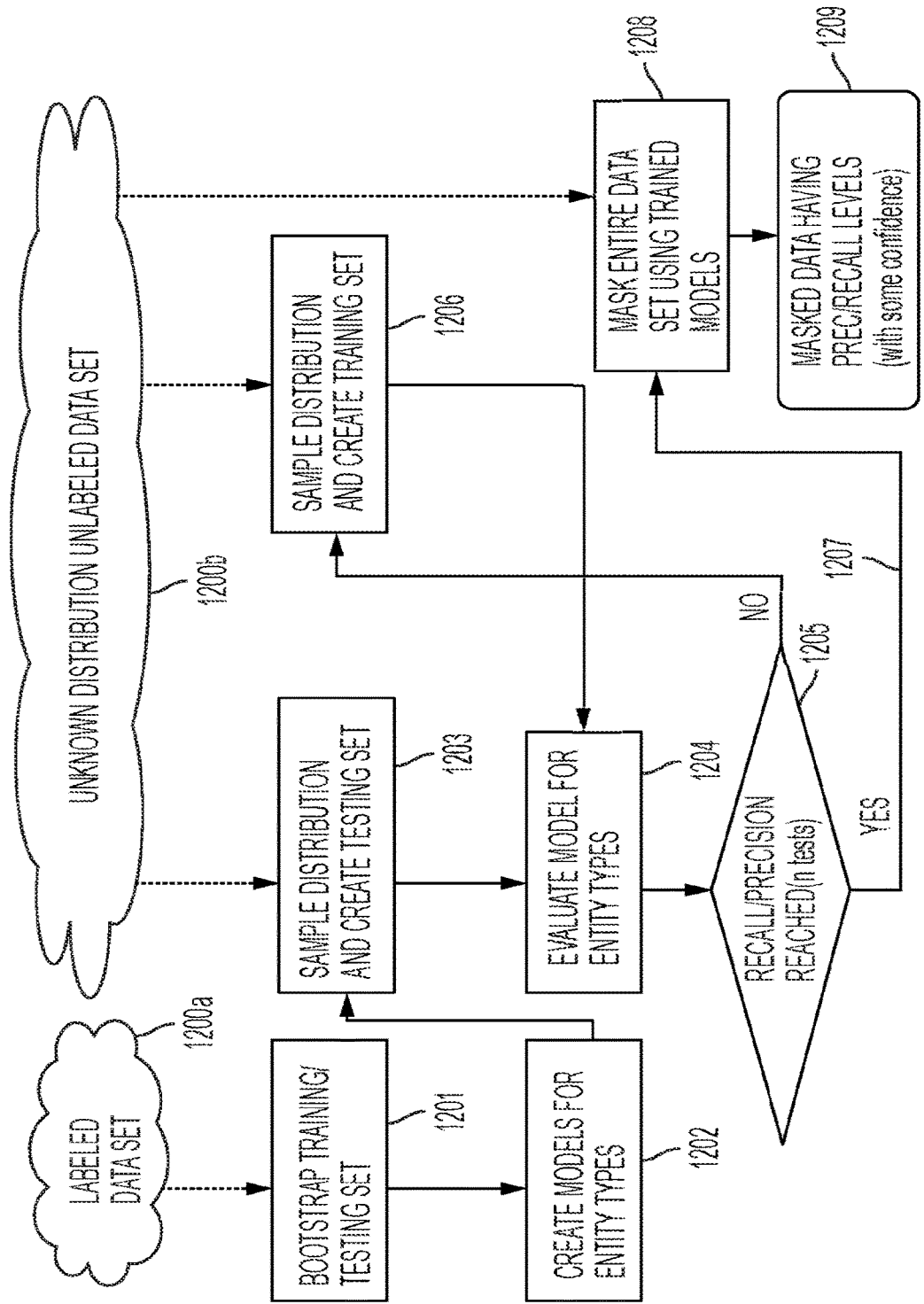
FIG. 12 is a simplified diagram of a control flow for information masking according to some embodiments.

FIG. 12 is a simplified diagram of a control flow for information masking according to some embodiments. The control flow describes a method to mask information in a large data set with unknown probability distribution (over the entities of interest) and is impractical to fully sample given its size. The method described in the present disclosure automatically subsumes unknown distribution over small data sets.

FIG. 12 illustrates two data sets 1200a and 1200b. Data set 1200a is a labeled data set for one or more the entity types to be masked. Data sets 1200a and 1200b may be a structured data set, organized using a tabular format having rows and/or columns associated with specific entity types. Additionally, data sets 1200a and 1200b may include unstructured data within specific cells of the structured data format, wherein the unstructured data can be free-form text or sentences. Entity types can include personal or organization names, locations, age, dates and times, phone numbers, pager numbers, clinical identification numbers, email and IP addresses, web URLs, vehicle numbers, physical addresses, zipcodes, social security numbers, and dates of birth, among other identifying characteristics. Any dictionary for an entity type could be added to 1200a for the specified entity type.

Subword based models like Bidirectional Encoder Representations from Transformers (BERT) that represent a word using subwords can leverage off subwords composing words in dictionary for tagging entities sharing those subwords. The unknown distribution data set 1200b is the data where certain entity types need to be selectively masked. It is not necessary for every entity type that needs to be masked to have an apriori labeled data set 1200a. A sample of data set 1200b could be used to create a labeled data set 1200a to bootstrap. In some instances, the sample of data set 1200b may be manually created by a system administrator or subject matter expert while other samples may be created using machine learning or rule-based algorithms that use pattern-matching rules, regular expressions, dictionary and public database lookups to identify PHI elements. For example, a rule-based algorithm may be based solely on the sequence of information in a standard format such as dates presented in the format of "Day/Month/Year" (e.g., XX/XX/XX or XX/XX/XXXX) or telephone numbers presented in ten-digit format (e.g., (XXX) XXX-XXXX). Based on these standard formats, the rule-based algorithm can identify the pattern and replace potentially identifying information with a generic placeholder to mask the information.

Entities of interest need not be limited to entities that need to be masked. It can be larger set of entities to ensure the model not only has a high recall for entities that need to be masked but also has a high precision for entities that are required for research (e.g. drugs, diseases etc.). Only a subset of entities of interest will be masked. The rest of the entities, while detected, will be used only for model performance evaluation.

The labeled data set for each entity type is used to fine tune a model 1202 for that entity type. While the preferred embodiment describes at least one separate model for each entity tagging, it does not preclude a model tagging multiple entities.

In a preferred embodiment of the disclosure each tagging model is an attention based model, e.g., the BERT model described in Devlin, et al., "BERT: Pre-training of deep bidirectional transformers for language understanding," arXiv preprint arXiv:1810.04805, which is incorporated by reference herein in its entirety. However other models, such as sequence models (e.g., long short-term memory networks (LSTMs), LSTM with a conditional random field (LSTM-CRFs), or recurrent neural networks (RNNs)) could be used for tagging entities. When using BERT, for each entity type a pre-trained model that is best suited for the entity type is chosen. For instance, when tagging entities like a person, location, etc., a model trained unsupervised on a generic corpus like Wikipedia, may suffice. In some embodiments, the pre-trained model may be based on other existing publicly available databases to augment model training such as health science journals, professional publications, peer-reviewed journal publications, or an operator-compiled database, among others. When tagging entities like disease, gene etc., a model trained on a scientific publication/bio-medical corpus may yield better results by helping incorporate domain-specific linguistic features into the model or identify emerging terms that may not otherwise have wide-spread prevalence in the field.

One method to discover templates or patterns of text from a large corpus of text data may include inferences generated by applying statistical named entity recognition (NER) models to individual sentences in the corpus. In large corpuses with often-repeated patterns of text, statistical methods may not capture all instances of a pattern. For example, in the sentence "Electronically signed by: SMITH, JOHN C on Jan. 2, 1980 at 12:12 PM CST", 'SMITH, JOHN C' might be detected as a person entity but in the very similar sentence "Electronically signed by: DEWEY, JONES K on Jan. 2, 1980 at 12:12 PM CST", 'DEWEY, JONES K' may not be fully be detected as a person. In such situations, pattern based methods perform better. A regular expression syntax like "Electronically signed by: [A-Za-z]+, [A-Za-z]+ [A-Za-z]+ on \d+/\d+/\d+ at \d+:\d+ PM CST" would capture all such cases. But, identification of patterns becomes an arduous, if not impossible, task, especially when done manually because it involves inspection of sufficiently large sample of sentences in the corpus. NER prediction can be used to generate sentence templates with entity values encoded by their type and mapping those encodings to syntactic patterns. This offers a way to automate generating pattern matching template candidates.

According to one embodiment, the NER models may be used by first splitting the corpus into individual sentences, as a form of pre-processing described further below with respect to FIG. 13. This may be completed by using natural language processing tools such as the Natural Language Toolkit, spaCy, CoreNLP, TextBlob, Gensim, or others. In some embodiments, splitting the corpus into sentences may reduce the overall amount of text to be processed, e.g., when the same sentence occurs multiple times in the corpus. Accordingly, splitting the corpus into sentences and de-duplicating the resulting set of sentences may improve computational efficiency. In some embodiments, one or more short sentences (e.g., sentences with fewer than a threshold number of words or terms) may be combined, which may provide additional context to the machine learning models and may improve the NER tagging performance. As an example, in the sentence "Performed by pet," the term "pet" could mean either an animal pet or an acronym for a person named "Peter" without capitalization (among other possibilities). However, if the previous sentence was "Epidural wore off after 4 hours," this provides adequate context to for a machine learning model to infer that "pet" most likely refers to the proper name of a person that administered the epidural.

After dividing the corpus into sentences (or multi-sentence passages), each unique sentence may be mapped to a syntax template that includes tokens associated with alphabetic, numeric, and alphanumeric characters. For example, contiguous sequences of letters may be identified using the token "W," while number-only sequences may be identified using the token "N," and alphanumeric sequences may be identified using the token "A." By way of example, the sentence "Electronically signed by: SMITH, JOHN C on Jan. 2, 1980 at 12:12 PM CST", for example, becomes "W W W: W, W W W N/N/N W N:N W W". The system may then create a list of the sentences within the corpus that align to each unique template generated using the tokens above and applies a statistical NER model to determine the quantity of sentences within the corpus that align to a selected template. However, using this token-based approach tokenizes every word, number, and alphanumeric character in the sentence, some of which need not be masked. The system also encodes the tokens based on the entity type identified within the templates. The token encoding technique may include the inside, outside, beginning (IOB) or IOB2 formats. Again by example, following this step, the original sentence "Electronically signed by: SMITH, JOHN C on Jan. 2, 1980 at 12:12 PM CST" becomes "Electronically signed by: B-PER, I-PER I-PER on B-DATE at B-TIME PM CST."

If a large number of the samples map to the same template then the system will identify that template as a candidate to become a rule and reduces the ambiguity in a rule matching different templates. Before transitioning a candidate template into a rule, the system may revert the IOB or IOB2 tags in the template with the corresponding syntax tokens by cross-referencing the token-identified sentence output with the IOB or IOB2 encoded output to identify entities that must be masked within the rule. Replacing the IOB2 formats with the tokens may allow for a simplified rule based on the tokens, but retains words or information in the original text of the template that need not be masked. For example, the formatted template "Electronically signed by: B-PER, I-PER I-PER on B-DATE at B-TIME PM CST" becomes "Electronically signed by: W, W W on N/N/N at N:N PM CST", which is a rule, or pattern template, to identify the named entities. The syntax tokens in the pattern template directly translate to standard syntactical pattern matching methods. For example "W" could be mapped to the regular expression "[A-Za-z]+", "N" to "\d+". Therefore, in an implementation, the pattern template of the example above could become the regular expression "Electronically signed by: [A-Za-z]+, [A-Za-z]+[A-Za-z]+ on \d+/\d+/\d+ at \d:\d PM CST".

In an alternative embodiment, following the separating of the corpus into individual sentences, as described above, the system may first pass the individual sentences through a statistical NER model that generates output of each sentence with entity terms extracted and replaced by IOB or IOB2 tags, similar to the description above. Next, the system may filter out templates that do not result in a specified threshold count of tagged entity types or tagged entity count. For example, the system operator may specify that only templates bearing at least two entity types are eligible for a rule, or potentially templates bearing at least four tagged entities, regardless of entity type. Once the threshold count is met, the system may map the IOB or IOB2 syntax tokens to the selected templates and create pattern templates using the same alphabetic, numeric, and alphanumeric tokens "W," "N," and "A" discussed above. After generating the pattern templates, the system may evaluate whether the pattern templates originate from unique statistical NER classes and select those unique pattern templates to create a rule. Each unique pattern template may be based on the number of sentences following a specific patterned sequence, or the number having a distinct number of entities or entity types. For example, if every instance of the pattern template "Electronically signed by: W, W W on N/N/N at N:N PM CST" was generated from an instance of the NER template "Electronically signed by: B-PER, I-PER I-PER on B-DATE at B-TIME PM CST", it is selected for rule creation. Doing so allows the system operator to limit rule-based templates to those that are unlikely to result in mismatched data masking by mis-identifying entity types within the corpus. In some embodiments, such as masking sensitive information, it may be useful for an operator to treat multiple entities as the same. Different templates that match can be manually inspected, after they have potentially passed some threshold for minimum number/percentage of matches. Although described using exemplary IOB/IOB2 syntax tokens, this rule generation method may use other forms of syntax or token systems to denote entities and entity types within the corpus.

Training and rule development may also consist of an operator manually classifying documents or records within the corpus based on a series of categories before evaluating individual models based on entity type. Data records may be classified into categories such as a segment description, service description, and service event such that the particular types of PHI within the records are more likely to be similar and identifiable. For example, the segment description for a particular record may be based on the nature of the note such as a progress note, consultation, discharge instructions, patient summary, or physician's note, among others. The service description may identify the department or area of treatment including medical oncology, orthopedic surgery, dermatology, family medicine, or emergency department as well as other facets of an organization or business. The service event may identify the setting in which the document was created, such as clinical outpatient, inpatient, emergency, lab, endocrinology consult, day surgery, or other document creation settings.

Once the corpus of training documents has been classified, individual validation sets may be used within the individual classifications to identify recurring data formats that commonly include PHI in recurring locations of the data records. For example, the classification may result in an identification that a dermatology service description collected in outpatient settings commonly includes PHI in the form of personal name information within the first sentence of the document. The classification may also be used to identify the distribution of number of patient notes per record type, wherein each note may include certain forms of PHI data. The classification may also allow an operator to identify the average number of PHI elements per record based on any one of the classification metrics. By identifying the prevalence of PHI based on classification, an operator may then prioritize note types (also referred to as PHI-enriched note types) and model training to focus on the records that contain high amounts of PHI data.

Once a specific pre-trained model is chosen for an entity type, the model is fine-tuned with the bootstrap training set 1201. The bootstrap training set 1201 may be updated using an iterative process whereby training samples are continuously added to the initial set of training samples, further described below in connection with FIG. 14. In some embodiments, existing training samples may be supplemented by individual sentences chosen from the selected corpus based on errors identified in prior models. After a model has been fine-tuned, a sample evaluation/test set is drawn 1203 from the unknown distribution 1200*b* and each model is evaluated for its efficacy 1204 by evaluating recall, precision, and F-Score levels. This step is performed for each entity type, and the recall/precision scores are computed.

If the average recall, precision, and F-score levels are at least as good as the required levels across n tests (where n is some number) then that entity training is considered complete. The required levels may be a threshold success percentage or ratio as determined by the system operator depending on the risk tolerance an operator has for identifying information being made available following the masking procedures. Once all entities have reached desired thresholds 1207, a full mask run 1208 is done on data set 1200*b*. A sampling is done on the masked set and examined for final measures of recall/precision 209.

If the average recall scores for an entity type is not above required threshold (1205) for that entity type, a sample is drawn from the unknown distribution unlabeled data set 1206 and evaluated again using the same methods to evaluate the efficacy of the model in step 1204. In step 1206, failed sentences that did not meet the threshold requirement are used to create template samples and added to training set 1206, using a dictionary associated within entity type to replace the actual entity instance in the failed sentence with equivalent entity instances from dictionary. By using the dictionary to replace the entity type, this ensures that the previously failed entity instance will be properly accounted for in future iterations of the training.

Figure 13:
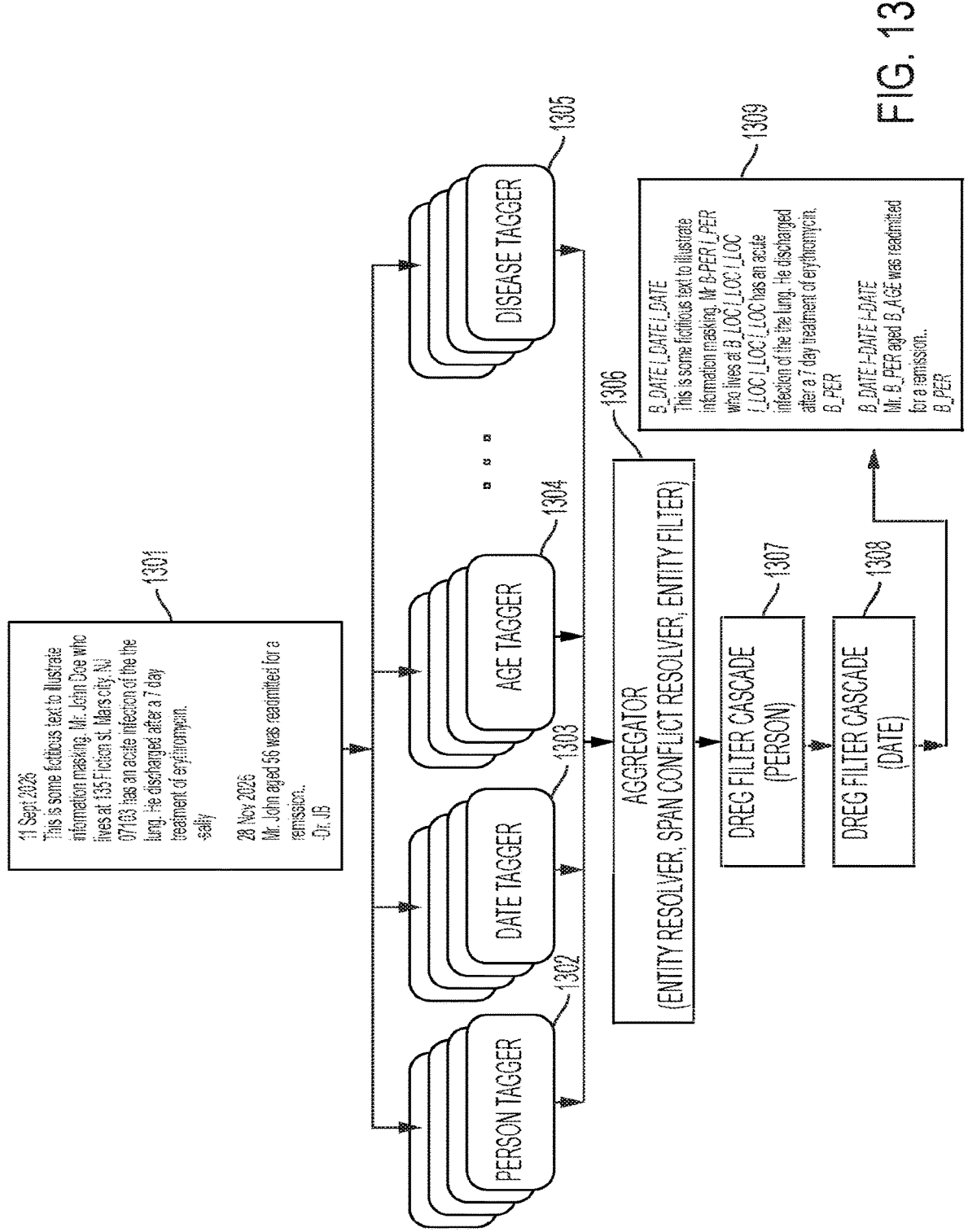
FIG. 13 is a simplified diagram of an entity tagging process and the handling of missed entities according to some embodiments.

FIG. 13 is a simplified diagram of an entity tagging process according to some embodiments. The input text 1301 is minimally pre-processed before being fed to each entity tagger. In some embodiments, the input text 1301 may include a batch of patient notes to be processed at the same time. As part of the pre-processing, the system may deconstruct the batch of notes and assign sentence identifiers ("sentence IDs") to the individual sentences such that each individual sentence from each of the notes can be processed individually, retaining a record of the sentence IDs for later compiling described below. Additionally, as part of the pre-processing, the system may associate sentences within the batch, tracked using the sentence IDs, if multiple sentences contain the same pattern or information. In this way, the system may only need to process one representative sentence of the associated sentences in order to accurately mask identifying information, only later performing the same masking to each of the associated sentences. The pre-processing may be entity dependent or entity independent. For instance, one pathway of input to a person tagger could be text where casing is preserved, while another pathway for input to another entity tagger of the same entity type may perform casing normalization (optionally using a POS tagger to have all noun forms to start with upper casing followed by lower case text). In some embodiments, paragraph breaks and/or punctuation may be used to separate the text of the batch of patient notes into individual sentences. In addition, unstructured text strings could be separated from a text file, a database, or any other commonly used data storage repository system.

In some embodiments, a whitelist tagger (not shown) may be employed prior to introducing the sentences to tagger models 1302-1305 to identify common or repeated phrases that are commonly identified as not containing PHI, and therefore do not require masking. For example, whitelisted entries can include computer generated text (e.g. "Please let your doctor know if you have problems taking your medications"), repeated phrases in the writing style of physicians (e.g. "Pain symptoms: No") or shared elements in the clinical notes such as section headers (e.g. "History of Present Illness"). These whitelist sentences can be removed from the data to be processed and routed to aggregator 1306 for later compiling since the risk of exposing PHI or other identifying information is a near-zero percentage. To create the whitelist tagger, a prevalence count for each unique sentence may be computed and identified based on the highest count after a manual review step. Using the whitelist tagger as part of the system preserves computational resources by not requiring tagging and masking of data that is known to not include PHI.

As shown in FIG. 13, multiple entity tagger models tag each entity type, the number and type of tagger models being dependent on the required recall, precision, and F-score levels required for that entity type among others. For example, tagger models 1302 are tailored to a personal or organization name entities, tagger models 1303 are tailored to date entities, tagger models 1304 are tailored to age entities, and tagger models 1305 are tailored to disease entities. Some of the tagger models may be trained using different training approaches such as rule-based approach, deep-learning models and pattern-based models. Doing so creates a diversified tagging approach for each entity type and further reduces the likelihood that the system will miss identifying entity information.

While in the preferred embodiment each entity type is tagged by one or more entity tagger models (the number of taggers for entity types is not a constant), other embodiments may have models that tag multiple entities. In some embodiments, the one or more entity tagger models associated with a particular entity may be fine-tuned to identify different complementary features associated with the entity in unstructured EHR data. For example, in the case of a tagger model tailored to name entities, one model could focus on identifying names in text while another could be tailored to names associated with addresses and locations, or in another case, an additional tagger model could focus on cased and uncased variants of the name without requiring pre-processing.

The tagged output from models 1302, 1303, 1304, 1305, is fed to an aggregator 1306 that outputs sentences that all desired entities are replaced by placeholder tags. The aggregator performs multiple functions such as fixing malformed entity sequences (e.g. I, I, etc. is converted to B, I sequence), resolving tagging conflicts (same term tagged as both disease and person—e.g. Mr. Parkinson), handling spans of entity types that are misaligned, and finally replacing tagged terms with placeholder tags. The aggregator may prioritize entities to be filtered based on the required recall, precision, F-score for entity types.

The output from the aggregator 1306 is then passed through a cascade of dreg filters, of which dreg filters 1307, 1308 are representative. Dreg filters may serve as a final processing filter against specific entity types to ensure that individual entities missed in the previous processing steps are not produced as output to users that should not have access to PHI. For example, dreg filter cascade 1307 is tailored to person entity types and dreg filter cascade 1308 is tailored to date entity types. Additional dreg filters may be included directed to the entity types associated with taggers 1302-1305. Dreg filters 1307, 1308 filter any term/phrase that failed to be tagged in the above steps. Dreg filters 1307, 1308 may use rule-based templates based on PHI-enriched note types to filter out additional PHI that was not identified by the tagger models 1302-1305. The rule-base templates may be tailored to individual sentence structures within data records to best identify PHI data. Each dreg filter cascade 1307, 1308 may be directed to a different entity type and include a plurality of rule-based templates. Dreg filters 1307, 1308 may also employ pattern-matching filters or similar approaches to identify PHI data. The final output 1309 is the original sentence and an associated array of tags (e.g., IOB2 format) for each word in the individual sentences, resulting in a desired masked output. Prior to final output 1309, the system may also compile each of the notes from the batch data set using the sentence IDs stored prior to the tagging carried out by tagging models 1302-1305.

Filter dregs take in input sentences, and the input is sent through a phrase tagger that marks beginning and end of phrases in a sentences using an IOB or IOB2 format. For those terms/phrases that were not tagged, a dictionary of entities, if present, is used to find similarity of vector representations of untagged phrases with vector representations of terms in the dictionary for each entity type. This is then used to further filter entities that may have been missed in previous steps.

For instance, if the name "jayendran balakrishnan" that appeared in a sentence was not tagged as a person (a false negative) or as any other entity type (false positive), that phrase would be picked up at filter cascade stages 1307/1308 and matched with vector representation of dictionary terms for each entity type. If the similarity measure exceeds some threshold, then the phrase is replaced from the sentence with a token or token expression. A BERT model can be used to create a vector representation of phrases because of its ability to construct words from subwords. In some embodiments, both the training models and/or the dreg filters can use associations between input terms, ordered by strength of their relationship, to group associations and identify developing words or phrases that may have been improperly tagged as PHI. For example, the input "ECOG" could be associated with top diseases based on publicly available literature, however the system may have tagged "ECOG" as a person's name. By reviewing the relationship between "ECOG" and commonly associated disease terms, the system can identify "ECOG" appropriately and not treat it as PHI.

The output from the cascade dreg filter phase 1308 is then used to evaluate model precision/accuracy. This may be completed using manual sampling of final output 1309 by a system operator, or an automated process as described below.

In some embodiments, tagged entities identified in the output data may be masked in a variety of ways. For example, the tagged entities may be deleted, replaced with blank characters, replaced with a placeholder that identifies the type of entity, or the like. In some embodiments, the value of the tagged entity may be changed to random information of the same type. For example, if the tagged entity is a phone number, the entity may be changed to a random (or otherwise obfuscated) phone number. This approach may obfuscate private information that the entity tagging model fails to detect. For example, if the entity tagging model detects and randomizes nine out of ten phone numbers in a given set of records, but misses the tenth, the end user of the data would not know which of the phone numbers is real and which is obfuscated, thereby providing a form of protection for the phone number that the tagger did not detect.

In some embodiments, specific patient ID fields may be retained in order to associate patient data records holistically within operator systems even after de-identification has been completed. For example, a patient intake ID may be retained in the corpus of masked documents in the event that an operator wants to retroactively pull the associated patient file, despite the information being made available to public after masking. Patient IDs may also take other forms such as patient birthdate, address, hospital room number, telephone number, or email address among others. Doing so allows operators to retain useful medical and biological signals in the data to maximize the utility of anonymized data even after each individual record instance may have been masked independently. Patient and other identifiers may provide a link between these individual records to accomplish such a goal.

When a patient ID is retained in a data record instance, some embodiments may include permissions for a covered entity, such as an individual or specified members of an organization, having access to encrypted versions of the patient record that bear the patient ID. For example, the covered entity may have specific credentials, such as encryption keys, passwords, or multi-step authentication methods to access versions of the patient data records that bear common patient identifiers. In other embodiments, the patient ID may be retained in all documents following the masking procedure, however a database correlating the patient ID to that patient's full set of medical records is stored in encrypted data files (also referred to as "linking" of patient data). Encryption methods may include AES-256 encryption. The data records may also be encrypted using a salt, or random data sequence used an additional one-way function to hash the data. Doing so prevents the data being compromised by brute force attacks using an efficient computing system to carry out the repeated guessing of the encryption hash. In some embodiments, secure hashing is one-way tracking where the system associates the hash with the patient ID, which requires separately storing an input ID and output hashed ID in disparate data repositories or storage locations in order to reconstruct the patient data record. This may include SHA-512 hashing, among others. In these embodiments, the covered entity may control access to the encryption keys, salts, and any output map, if generated.

In other embodiments, the system may be used to mask PHI included in images such as x-ray or opt homology images that have PHI embedded as text in the image itself. In such embodiments, the system may employ a convolutional neural network to automatically detect regions in images based on an operators preferred program or application in which the images are made. In some embodiments, the system may automatically detect and extract text from identified regions in the images, then map that text to substitutable anonymizing text from a database similar to the description above with regard to sentence-by-sentence. In other embodiments, the system may use Multi Instance Learning (MIL) which consists of a convolutional neural network trained to take whole slide image level labels and make predictions at patch level (e.g., sub-regions of an image identified as containing PHI). Representative patch sizes can be based on the two-dimensional pixel sizes of the images and can employ max pooling or recurrent neural networks (RNN) on patch level predictions to predict the class at a slide-by-slide level, rather than a pixel level annotation. In another embodiment, the system may use image similarity methods to identify and mask PHI found within specific images. To train such a model, the system operator may select a particular sub-region of a training image and set a resolution value, then ask the system to find all similar patches from the database at the same resolution value. For example, a classifier network based on the triplet loss concept may be first built to efficiently learn fine-grained features (as a vector) from each image at every resolution. Then a database of such image-derived feature vectors is created; treating distinct magnification/resolution levels of an image as distinct images themselves. Then the system may use modern high performance high dimensional similarity search methods (e.g., siamese neural networks, among others) to find the patches most similar to the patches used by the user in their query.

Figure 14:
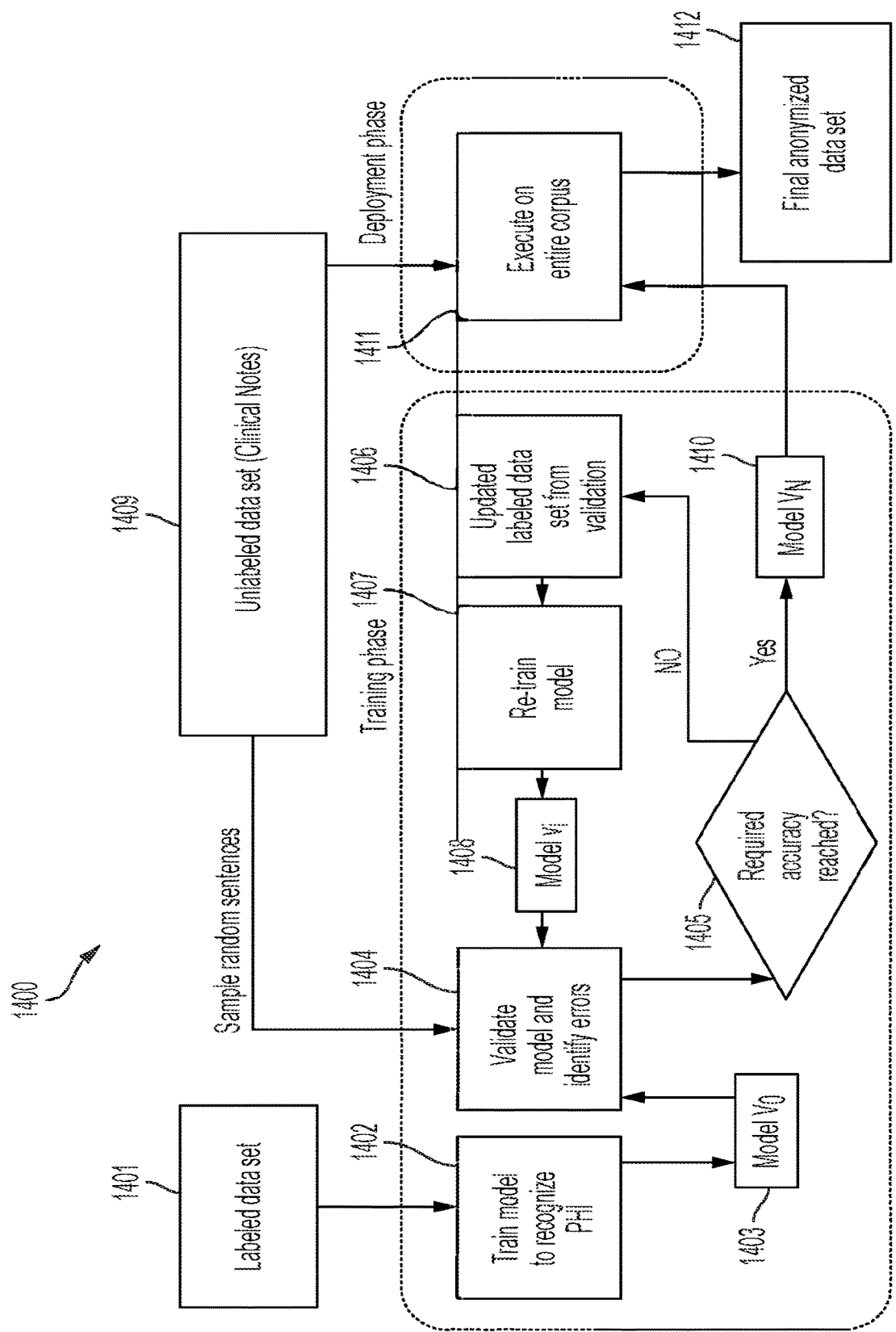
FIG. 14 is a simplified diagram illustrating a testing suite diagnostic flow method for masking efficacy according to some embodiments.

FIG. 14 is a simplified diagram illustrating a testing suite diagnostic flow method for masking efficacy according to some embodiments. The testing suite method 1400 allows an operator to both train new models in a testing environment or continually hone the parameters of individual tagging models previously deployed in the live system to improve the precision, recall, and F-score levels of a particular entity model, similar to that described in FIG. 12. For a new model, the system operator may introduce a labeled data set 1401 to the system in the training phase that includes tags associated with particular entities in the data set. This labeled data set may be manually identified by an operator or be a product of previously labeled data sets produced by the model taggers 1302-1305 described in FIG. 13. At step 1402, in the training phase of the testing suite, the labeled data set is introduced to an initial tagger model $V_O$ 1403 in order to train initial tagger model $V_O$ 1403. At step 1404, Model $V_O$ 1403 analyzes a subset of unlabeled data set 1409 and produces an output of the labeled data set bearing a set of tokens that Model $V_O$ 1403 identified within the unlabeled data set. The output is then evaluated at step 1405 to validate the tagger model type (e.g., which entity type/types it is tailored to) and identify any errors in the tokens tagged from the labeled data set. The testing suite determines the precision, recall, and F-score levels for the Model $V_O$ 1403 output and measures all three scores against threshold values determined by the system operator.

If the precision, recall, and F-score levels do not meet the required threshold values at step 1405, the testing suite system selects a different, or updated labeled data set at step 1406 and reintroduces the updated labeled data set to the Model $V_O$ 1403 at step 1407 such that the model takes on a new character, resulting in Model $V_i$ 1408. The updated labeled data set can be based on errors perceived in step 1404 such that the model iteratively improves its own ability to recognize specific entity types. Following the retraining, Model $V_i$ 1408 will tag the updated labeled data set bearing a new set of tokens that Model $V_i$ 1408 identified within the updated labeled data set, the output of which is then evaluated in the same way as Model $V_O$ 1403 at steps 1404 and 1405. In some embodiments, the Model $V_i$ 1408 may be validated against a portion of an unlabeled data set 1409 taken from a corpus of reported data, such as clinical notes. This process will repeat in an iterative fashion until the retrained model meets the required threshold values for precision, recall, and F-scores at step 1405. Once complete, the verified Model $V_N$ 1410 may be produced as final, where N represents the number of iterations within the training phase the model needed to complete before reaching adequate threshold accuracy at step 1405.

After confirmation, Model $V_N$ 1410 may be deployed into the live system and be used, at step 1411, to tagging data received from the larger corpus of unlabeled data set 1409. The processing of data at step 1411 is the same as that described above with respect to FIG. 3, resulting in the final anonymized data set at step 1412.

It is to be understood that the foregoing embodiments are illustrative and that various alternatives are possible. In some embodiments, given a set of words (or multi-word terms) corresponding to a particular entity type, one or more contiguous phrases are extracted from a text document or corpus that contain words in the set. For example, consider a set of words corresponding to types of tissue. That is, the set may illustratively contain words such as "lung," "liver," "brain," etc. The set may also contain terms such as "left," "right," and "posterior," which are often used as additional modifiers in the context of tissues. Conversely, the set of words may omit words and phrases that could represent PHI or other sensitive information. Given a particular text fragment (e.g., "Mr. Smith visited MGH today for his left lung surgery"), phrases made up of words found in the set of words corresponding to the entity (e.g., "left lung") are extracted. In particular, in the foregoing example, the phrase "left lung" is extracted even though the set of words does not directly include this phrase; rather the set includes the constituent words "left" and "lung." In this manner, useful information may be extracted from text while patient-identifiable content (e.g., the name "Mr. Smith" in the above example) is not extracted. This approach can readily be extended to a wide variety of biomedical entities such as diseases, drugs, and the like.

In some embodiments, named entity recognition may be performed in an unsupervised manner without using labelled training sentences. For example, named entity recognition may be performed using a BERT model that has been trained on a corpus using the Masked-Language-Model objective. An illustrative example of this technique is described in further detail in the article "Unsupervised NER using BERT," Towards Data Science, Feb. 28, 2020 (https://towardsdatascience.com/unsupervised-ner-using-bert-2d7af5f90b8a), which is incorporated by reference herein in its entirety.

In addition to the above-described challenges associated with securely processing and receiving information, such as private healthcare data, it can be challenging to retrieve information that is responsive to a search query from a repository of information. Information can be stored in a variety of ways, such as in a collection of documents, a database (e.g., a structured, semi-structured, or unstructured database), a knowledge graph, or the like. Some information retrieval tools are designed to retrieve documents or other records from a repository based on a query term. For example, various publicly available search engines (e.g., Google or PubMed) are configured to identify web pages, journal articles, books, etc. that are relevant to a user-provided query term.

However, in some scenarios, identifying relevant records in a repository may not yield an adequate response to a user's query. For example, when the user is seeking to make a determination or inference based on aggregated information (e.g., to determine whether a particular drug has been shown to be effective against a particular disease based on an aggregate of studies performed on the drug), search results that include a list of relevant documents may not clearly and directly respond to the user's query. To illustrate, in the above example of a user seeking an answer to whether a particular drug has been shown to be effective against a particular disease, the user may be left with the onerous task of browsing each relevant document (e.g., each document that mentions the drug and the disease) to determine which documents are in fact responsive to the query. Subsequent manual analysis of the responsive documents may then be performed to yield the answer to the initial question posed by the user. This process of manually examining search results to piece together the desired information and make a suitable determination or inference can be tedious and time-consuming.

Accordingly, it is desirable to develop improved techniques for retrieving information that is responsive to a query, particularly techniques that can be applied to information stored in heterogenous formats.

Figure 15:
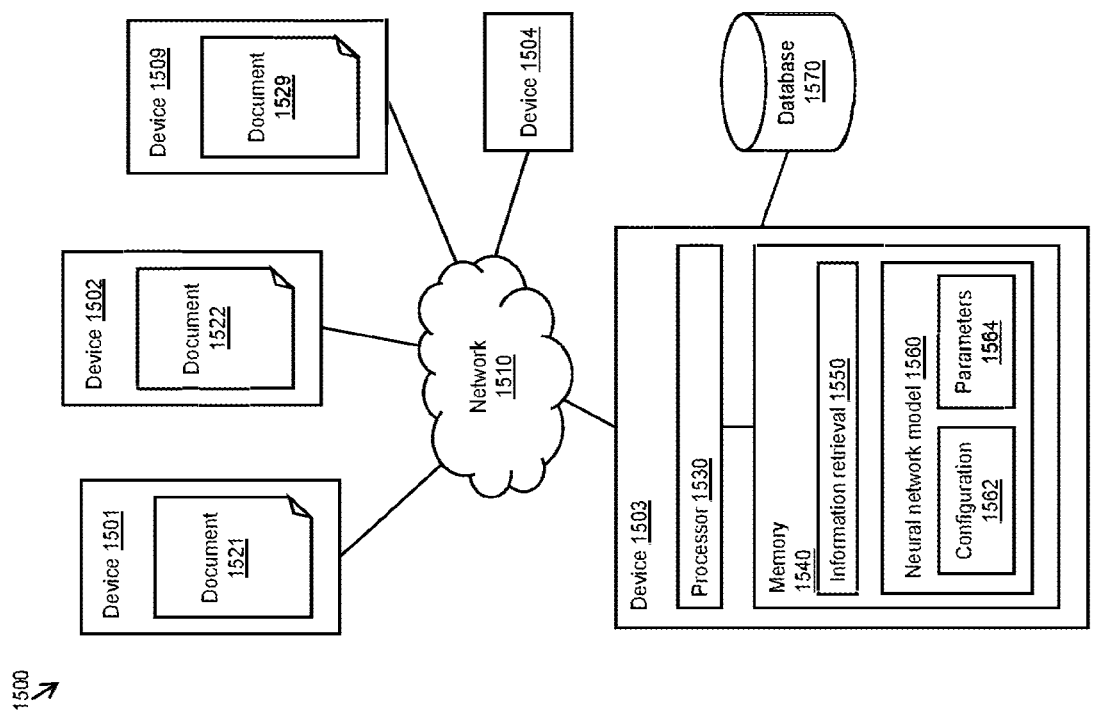
FIG. 15 is a simplified diagram of a system for information retrieval according to some embodiments.

FIG. 15 is a simplified diagram of a system 1500 for information retrieval according to some embodiments. System 1500 includes a plurality of devices 1501-1509 that are communicatively coupled via a network 1510. Devices 1501-1509 generally include computer devices or systems, such as personal computers, mobile devices, servers, or the like. Network 1510 can include one or more local area networks (LANs), wide area networks (WANs), wired networks, wireless networks, the Internet, or the like. Illustratively, devices 1501-1509 may communicate over network 1510 using the TCP/IP protocol or other suitable networking protocols.

One or more of devices 1501-1509 can store digital documents 1521-1529 and/or access digital documents 1521-1529 via network 1510. For example, as depicted in FIG. 15, devices 1501, 1502, and 1509 store digital documents 1521, 1522, and 1529, respectively, and device 1503 accesses digital documents 1521-1529 via network 1510. Digital documents 1521-1529 can include webpages, digital files, digital images (including one or more frames of a video or an animation), or the like. Illustratively, digital documents 1521-1529 can be formatted as HTML/CSS documents, PDF documents, word processing documents (e.g., Word documents), text documents, slideshow presentations (e.g., PowerPoint presentations), image files (e.g., JPEG, PNG, or TIFF images), or the like. Digital documents 1521-1529 can be heterogeneous (e.g., of different formats or file types) or homogenous (e.g., of the same format or file type), and can include structured or unstructured data. In general, digital documents 1521-1529 include text data, which can include alphanumeric characters, symbols, emojis, image representations of text, or the like. For efficient storage and/or transmission via network 1510, documents 1521-1529 may be compressed prior to or during transmission via network 1510. Security measures such as encryption, authentication (including multi-factor authentication), SSL, HTTPS, and other security techniques may also be applied.

According to some embodiments, device 1503 may access one or more of digital documents 1521-1529 by downloading digital documents 1521-1529 from devices 1501, 1502, and 1509. Moreover, one or more of devices 1501, 1502, or 1509 can upload digital documents 1521-1529 to device 1503. Digital documents 1521-1529 may be updated at various times. Accordingly, device 1503 may access digital documents 1521-1529 multiple times at various intervals (e.g., periodically) to obtain up-to-date copies.

In some embodiments consistent with FIGS. 1-14, one or more of devices 1501-1509 may correspond to or include a secure data store, such as secure data stores 810, 901, and 1009. For example, one or more of digital documents 1521-1529 may include private healthcare data, and accordingly may include information that is masked, e.g., to comply with privacy regulations. The masking may be performed by an information masking system, such as information masking system 1102, using techniques consistent with FIGS. 1-14. In some embodiments, the information masking system may be included as part of system 1500, may be a separate system, or may be distributed across multiple systems. The masking may be performed prior to, during, or after being accessed by device 1503.

As depicted in FIG. 15, device 1503 includes a processor 1530 (e.g., one or more hardware processors) coupled to a memory 1540 (e.g., one or more non-transitory memories). Memory 1540 stores instructions and/or data corresponding to an information retrieval program 1550. When executed by processor 1530, information retrieval program 1550 causes processor 1530 to perform operations associated with retrieving information responsive to a query. In some embodiments, the query may be provided as an input (e.g., a query string) by a user of device 1504 and transmitted to device 1503 via network 1510. Subsequently, a response to the query determined using information retrieval program 1550 may be delivered via network 1510 to device 1504 and rendered to the user via a user interface. Illustrative embodiments of data flows implemented by information retrieval program 1550 are described in further detail below with reference to FIGS. 16-17.

During execution of information retrieval program 1550, processor 1530 may execute one or more neural network models 1560. Neural network model 1560 is trained to make predictions (e.g., inferences) based on input data. Neural network model 1560 includes a configuration 1562, which defines a plurality of layers of neural network model 1560 and the relationships among the layers. Illustrative examples of layers include input layers, output layers, convolutional layers, densely connected layers, merge layers, and the like. In some embodiments, neural network model 1560 may be configured as a deep neural network with at least one hidden layer between the input and output layers. Connections between layers can include feed-forward connections or recurrent connections.

One or more layers of neural network model 1560 is associated with trained model parameters 1564. The trained model parameters 1564 include a set of parameters (e.g., weight and bias parameters of artificial neurons) that are learned according to a machine learning process. During the machine learning process, labeled training data is provided as an input to neural network model 1560, and the values of trained model parameters 1564 are iteratively adjusted until the predictions generated by neural network 1560 match the corresponding labels with a desired level of accuracy.

For improved performance, processor 1530 may execute neural network model 1560 using a graphical processing unit, a tensor processing unit, an application-specific integrated circuit, or the like.

Device 1503 may be communicatively coupled to a database 1570 or another suitable repository of digital information. For example, database 1570 may be configured as a structured database with contents organized according to a schema or other logical relationships (e.g., relational database). In some embodiments database 1570 may be configured as a non-relational database, a semi-structured database, an unstructured database, a key-value store, or the like. Although database 1570 is depicted as being coupled directly to device 1503, it is to be understood that a variety of other arrangements are possible. For example, database 1570 may be stored in memory 1540, accessed via network 1510, or the like.

Figure 16:
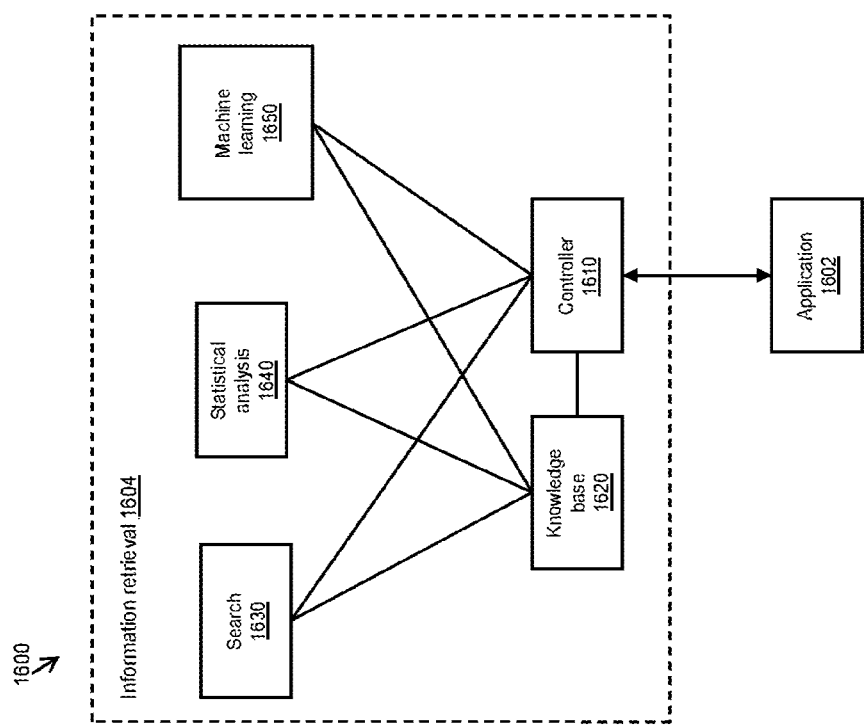
FIG. 16 is a simplified diagram of a data flow for information retrieval to some embodiments.

FIG. 16 is a simplified diagram of a data flow 1600 for information retrieval to some embodiments. In some embodiments consistent with FIG. 15, data flow 1600 may be implemented using various components and/or features of system 1500, as further described below. In some embodiments consistent with FIGS. 1-14, data flow 1600 may be configured to retrieve information that includes or is based on private healthcare data. Accordingly, data flow 1600 may be implemented using techniques consistent with FIGS. 1-14. For example, data flow 1600 may be implemented within one or more containers, and input information may be masked as described with reference to FIGS. 1-14.

As depicted in FIG. 16, an application 1602 is communicatively coupled to an information retrieval system 1604. In some embodiments consistent with FIG. 15, information retrieval system 1604 may correspond to information retrieval program 1550. Application 1602 generally corresponds to a program that is configured to provide queries to information retrieval system 1604 and handle responses from information retrieval program 1604. For example, application 1602 may correspond to a web application or a mobile application that receives queries from a user, sends the queries to information retrieval system 1604 (e.g., via an API), and receives and renders corresponding responses. In some embodiments consistent with FIG. 15, application 1602 may include a front-end component that runs on device 1504, a back-end component that runs on device 1503, or the like. In some embodiments, information retrieval system 1604 may provide a standardized API or other interface that allows information retrieval system 1604 to communicate with various types or versions of applications. In some embodiments, information retrieval system 1604 may provide a user interface that allows user to provide queries to information retrieval system 1604 directly, bypassing application 1602.

Information retrieval system 1604 includes a plurality of modules 1610-1650 that are used to fulfill the user's request. In some embodiments, modules 1610-1650 may each be components of an integrated program. In some embodiments, modules 1610-1650 may be independent programs (e.g., microservices) that operate independently of one another and communicate with each other via standard interfaces. Information retrieval system 1604 can be distributed. For increased performance and parallelism, information retrieval system 1604 may include multiple instances of modules 1610-1650.

A controller module 1610 of information retrieval system 1604 receives and handles queries (and/or other types of requests) from application 1602. Controller module 1610 is coupled to one or more other modules of information retrieval program 1604 (e.g., modules 1620-1650) and coordinates among the other modules to fulfill the request. In some embodiments, the process of fulfilling the request may vary depending on the type of the request.

A knowledge base module 1620 of information retrieval system 1604 provides access to a knowledge base that identifies various types of relationships among information. For example, knowledge base module 1620 may store collections of terms that are known to share a given relationship (e.g., the terms may be synonyms of one another). In some embodiments, the information and their associated relationships may be stored and retrieved using a knowledge graph or other suitable data storage techniques.

In general, it is desirable for the knowledge base stored by knowledge base module 1620 to be comprehensive with respect to the subject matter of interest. A comprehensive set of relationships may be identified and aggregated using a variety of techniques. In some embodiments, the knowledge base may be built by starting with an existing knowledge base, such as the Unified Medical Language System (UMLS) in the case of the biomedical domain, and then aggregating onto it other sources of domain-specific information. For example, data may be aggregated from external databases (e.g., publicly available databases and proprietary or customer-specific databases). Relationships among the aggregated data may be identified using a neural network model (e.g., neural network model 1560) or other information retrieval methods configured to mine relationships from the aggregated data.

A search module 1630 of information retrieval system 1604 provides a search engine capable of searching a corpus of text (e.g., a collection of documents, database records, and/or the like) based on a query term. The corpus can include, for example, a public literature corpus, a clinical data corpus (e.g., physician notes and other types of patient health records), or both. The corpus can include structured or unstructured data. In some embodiments, the structured data may include one or more structured data fields of a patient health record, such as the name of a drug to be administered. Such information may be expected to be more reliable than an unstructured entry in a patient health record, for example, because such information may be used for insurance purposes or a variety of other formal or legal functions. The use of structured data fields within patient health records may therefore improve reliability and, in embodiments where at least a subset of the corpus is labeled to provide training (or testing) data for a machine learning model, may reduce the amount of data that is tagged manually. This may facilitate the rapid and accurate development and training of machine learning models based on the corpus, such as sentiment classifiers.

One challenge associated with use of a clinical data corpus, or other corpus that includes patient data, is privacy concerns discussed previously. Accordingly, one or more of the techniques discussed in FIGS. 1-14 may be used to provide for a secure processing environment and to de-identify or mask sensitive patient data. For example, the entity tagging process of FIG. 13 may be applied to the corpus (or a portion of the corpus containing sensitive information) to mask the sensitive information. In some embodiments, search of the corpus may be suppressed to omit patients with rare conditions that make these patients easy to identify based on their condition alone. For example, if a patient is associated with a cohort (e.g., the number of patients with a similar or same condition) that is below a minimum threshold size, that patient's records may be suppressed in the corpus, such that the patient's records are not returned in a list of search results.

In some embodiments, search module 1630 may identify and retrieve complete text documents or database records from the corpus that are determined to be relevant to the query term. However, as discussed previously, this approach has various limitations. For example, when the user is seeking to make a determination or inference based on aggregated information (e.g., to determine of whether a particular drug has been shown to be effective against a particular disease based on an aggregate of studies performed on the drug), search results that simply include a list of relevant documents may not clearly and directly respond to the user's query. This approach may therefore entail tedious and time-consuming efforts on the part of the user to examine each of the search results to piece together the desired information and make a suitable determination or inference.

To address these limitations, search module 1630 may be configured to return a list of text fragments that match the query term, rather than (or in addition to) a list of matching documents or records. This fragment-based search approach yields localized portions of documents (e.g., a few words, sentences, or paragraphs) that contain information of interest, e.g., information that is directly relevant to the determination or inference that the user is seeking to make. In this manner, where a document is not generally relevant to the user's query but contains a responsive fragment, the responsive text fragment is returned in the search results even if the document as a whole would not be relevant enough to be included in a list of matching documents. Conversely, where a document strongly matches the query term but does not include any fragments that directly respond to the query, the document may not yield any fragments in the list of matching text fragments. Moreover, if a given document or record includes more than one matching text fragment, the single document or record may yield multiple entries in the returned list of text fragments. As a result, the fragment-based search approach may improve the overall the relevance and completeness of the search results. Illustrative embodiments of a fragment search module are described in further detail below with reference to FIG. 17.

A statistical analysis module 1640 of information retrieval system 1604 provides tools to statistically analyze information from other modules of information retrieval system 1604, such as the list of search results provided by search module 1630. A wide range of statistical analyses may be performed, depending on factors such as the type of request received from the user. For example, statistical analysis module 1640 may compute the statistical significance of various entities and terms appearing in the list of search results from search module 1630 (e.g., a count of the number of occurrences of a given term in the search results, a count of the number of co-occurrences of the term with other terms, a score or ranking to compare the significance of a term relative to other terms, or the like). In performing the statistical analyses, statistical analysis module 1640 may communicate with and retrieve information from other modules of information retrieval system 1604. Examples of statistical significance metrics that may be computed using statistical analysis module 1640 are described in further detail below with reference to FIG. 18.

A machine learning module 1650 of information retrieval system 1604 provides tools for applying machine learning models (e.g., neural network model 1560) to information from other modules of information retrieval system 1604, such as the list of search results provided by search module 1630. In some embodiments, machine learning module 1650 may include a natural language processing (NLP) pipeline for analyzing the text of the search results. The NLP pipeline may include NLP primitives (e.g., tokenization, embedding, named entity recognition, etc.). Moreover, the NLP pipeline may include pre-trained rule-based or machine learning models, including but not limited to negative expression finders, sentiment classifiers, entity extractors, or the like. Further statistical analysis may be performed on the output of the NLP pipeline to identify relationships and associations among the results.

Figure 17:
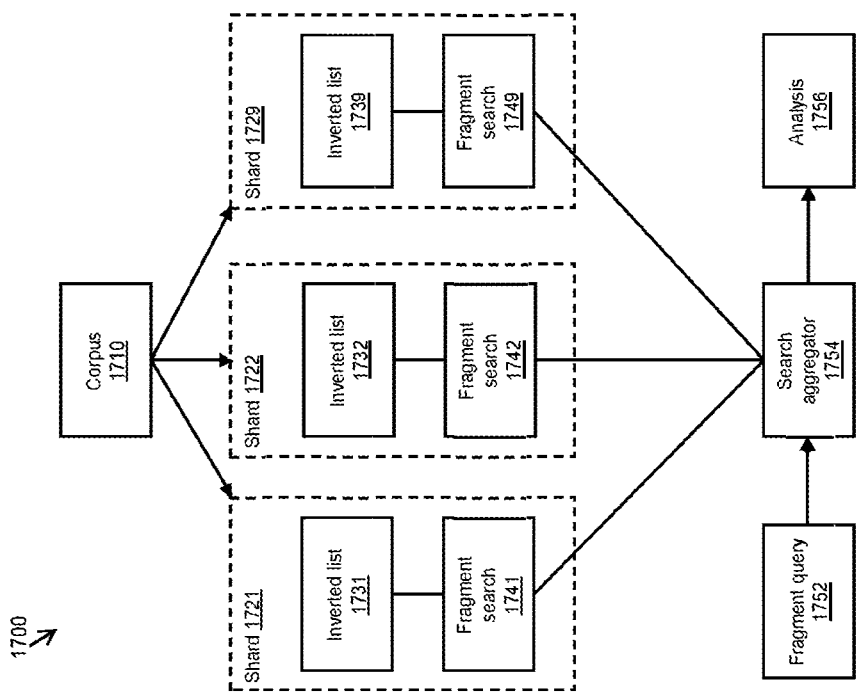
FIG. 17 is a simplified diagram of a data flow for fragment searching according to some embodiments.

FIG. 17 is a simplified diagram of a data flow 1700 for fragment searching according to some embodiments. In some embodiments consistent with FIG. 16, data flow 1700 may be implemented using search module 1630.

A corpus 1710 corresponds to a collection of text, such as a collection of one or more text documents or database records. For example, corpus 1710 may correspond to documents 1521-1529 received from devices 1501-1509 and/or may include documents stored locally by device 1503. In some embodiments, corpus 1710 may be stored in memory 1540, database 1570, in an on-chip memory (e.g., cache), or the like. The documents in corpus 1710 can be stored in a native format (e.g., in the format as received from devices 1501-1509), or various pre-processing operations may be performed on the received documents to modify the content or format of the documents. For example, non-text data (e.g., image data) and/or metadata may be removed from the documents, text data may be extracted from the documents (e.g., by optical character recognition), or the like. The format of the documents may be converted to a uniform format, or data from the documents may be used to populate a database (e.g., database 1570). In some embodiments, corpus 1710 may be dynamically updated.

The contents of corpus 1710 can relate to general subject matter (e.g., a collection of news articles or Wikipedia entries covering a variety of topics) or domain-specific subject matter. Illustratively, corpus 1710 may relate to biomedical subject matter. For example, corpus 1710 may include text from journal articles, reference textbooks, patent applications, websites, etc. related to biomedical fields. Corpus 1710 can be drawn from a wide variety of sources, such as molecular databases, scientific literature, insurance documents, pharmaceutical company websites, news feeds, regulatory information (clinical trials, SEC filings, IP), or the like. In some embodiments consistent with FIGS. 1-15, corpus 1710 may include private data (e.g., healthcare records) that have been processed and stored in accordance with the techniques discussed above.

As depicted in FIG. 17, corpus 1710 is partitioned into a plurality of subsets. Each subset may be provided to a respective shard among shards 1721-1729. In some embodiments, splitting corpus 1710 among shards 1721-1729 may facilitate processing of corpus 1710 using distributed computing resources (e.g., using distributed processors and/or storage systems). For example, one or more of shards 1721-1729 may be located on different machines within a data center and/or in different data centers. In some embodiments, each of the subsets of corpus 1710 may be approximately equal in size, e.g., they may occupy similar total disk space or they may include a similar number of documents.

Each of shards 1721-1729 includes a corresponding inverted list 1731-1739. Each of inverted lists 1731-1739 identifies, for each token (e.g., word) in the corresponding subset of corpus 1710, a list of occurrences of the token within the subset of corpus 1710. For example, an inverted list 1731-1739 may identify the positions of each occurrence of the token within the subset of corpus 1710 (e.g., the positions within a contiguous array of text that corresponds to a concatenation of each document in the subset of corpus 1710). In some embodiments, the inverted list 1731-1739 may identify a document identifier corresponding to the document in which the token occurs, an offset within the document to the occurrence of the token, or the like. In some embodiments, each entry in the inverted list 1731-1739 may include a plurality of location identifiers for each occurrence of each token. The plurality of identifiers may be stored in an appropriate data structure, such as a triplet that identifies (1) the array index of the occurrence of the token within a contiguous array of concatenated documents, (2) the document identifier of the occurrence, and (3) the offset within the identified document to the occurrence.

In some embodiments, the inverted lists 1731-1739 may be ordered to facilitate efficient lookup of tokens. For example, the inverted lists 1731-1739 may be ordered based on an ascending order of each token's positions within the array of text corresponding to the subset of corpus 1710. The inverted list 1731-1739 may be indexed using integer values associated with each token, such that given an integer corresponding to a token, the data structure containing inverted list 1731-1739 efficiently returns a corresponding list of occurrences of the token.

Each of shards 1721-1729 further includes a corresponding fragment search module 1741-1749. Each of fragment search modules 1741-1749 is configured to receive a fragment query 1752 and generate a response to the fragment query by accessing data from inverted lists 1731-1739. A fragment query 1752 may be distributed to the fragment search modules 1741-1749 using a search aggregator 1754. The search aggregator 1754 may then receive and aggregate the search results generated by fragment search modules 1741-1749. The search results may then be used for subsequent analysis 1756. For example, in some embodiments consistent with FIG. 16, the analysis 1756 may be performed using one or more of knowledge base 1620, statistical analysis module 1640, or machine learning module 1650.

In some embodiments, fragment query 1752 includes one or more query parameters indicating the desired search criteria for the fragment search. For example, fragment query 1752 may include a query parameter (e.g., a combination of one or more tokens, words, or multi-word phrases to be searched, optionally joined by Boolean operators, such as AND, OR, and NOT). Fragment query 1752 may also include a size parameter indicating the desired size of the text fragment returned by fragment search module 1741-1749. Fragment query 1752 may further include a document parameter that specifies one or more criteria that a document should satisfy as a prerequisite for fragments in the document to be included in the search results. For example, the document parameter may include a criteria that eligible documents include a specified single or multi-word phrase (or logical combinations thereof) or a criteria that eligible documents be associated with document metadata (e.g., author names, publication years, document source, document type, or the like). Consistent with such embodiments, fragment query 352 may be represented using an appropriate data structure for transmitting and processing the various search parameters, such as a data structure represented as <FragQuery, FragmentSize, DocumentSpecifier>, where FragQuery denotes a query parameter, FragmentSize denotes a size parameter, and DocumentSpecifier denotes eligibility conditions for documents to be included in the search results.

Figure 18:
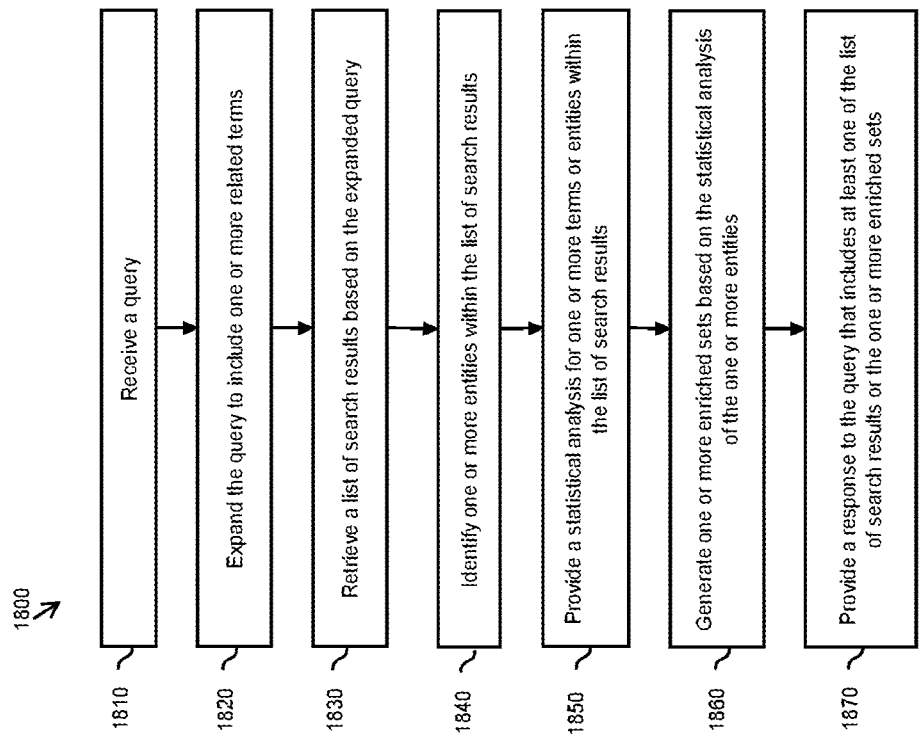
FIG. 18 is a simplified diagram of a method for retrieving information responsive to a query according to some embodiments.

FIG. 18 is a simplified diagram of a method 1800 for retrieving information responsive to a query according to some embodiments. According to some embodiments consistent with FIGS. 15-17, method 1800 may be performed by processor 1530 during the execution of information retrieval program 1550. For example, method 1800 may be performed using controller module 1610.

At a process 1810, a query is received by a controller (e.g., controller module 1610). The query can include one or multiple tokens (e.g., words, sentences, etc.), Boolean operators, constraints, filters, and various other parameters. In some embodiments, the query may be included in a request sent by an application, such as application 1602. Consistent with such embodiments, the request may be received via and API. In response to receiving the request, the controller may process and respond to the request by gathering information responsive to the query according to one or more of the following processes 1820-1850. In distributed computing environments, the information may be gathered via communications transmitted to and from various modules located at different network nodes.

At a process 1820, the query is expanded to include one or more related terms. The related terms may be retrieved from a knowledge base, such as the knowledge base of knowledge base module 1620. In some embodiments, the related terms may share a predetermined relationship with the terms in the original query (e.g., the terms may be synonyms of one another). In this manner, retrieving the related terms may broaden the query to include terms with similar meanings to the terms provided by the user.

At a process 1830, a list of search results is retrieved based on the expanded query. The list of search results includes documents or passages (or information that identifies such documents or passages) that match the query. The list of search results may be retrieved via a search engine or search module, such as search module 1630. In some embodiments, the search results may be retrieved from a corpus of text (e.g., a collection of documents, database records, and/or the like) based on a query term provided by the controller. For example, the search results may correspond to the results of a fragment-based search. In this approach, the search results include fragments (e.g., a few words, sentences, paragraphs, or other localized portions of documents) that contain information of interest. Illustrative embodiments of a fragment-based search are discussed in further detail below with reference to FIG. 19.

In some embodiments, the list of search results may be referred to as a "context" of the query and may be stored or indexed using a suitable data structure. The context includes windows of the corpus that include query terms, along with terms that appear near the matching query term within the corpus (e.g., terms that appear within a window size of n tokens of the matching query term in the corpus). The context may be binary or nonbinary. In a binary context, terms in the corpus are either included in the context (e.g., if they are within n tokens of an appearance of the query term) or they are omitted from the context. In a non-binary or "smooth" context, terms in the corpus may be weighted (e.g., assigned a value between 0 and 1) based on factors such as the distance from the query term. For example, the weight assigned to a term in a non-binary context may attenuate exponentially based on distance of the term from the query term.

At a process 1840, one or more entities are optionally identified within the list of search results. For example, in the context of biomedical applications, illustrative examples of entities may include names of drugs, diseases, genes, pharmaceutical companies, research institutions, or the like. In some embodiments, the one or more entities may be identified by referencing a knowledge base, such as the knowledge base of knowledge base module 1620. For example, the knowledge base may store collections of entities, such that the list of search results may be compared to the collections of entities to identify entities in the list of search results. In some embodiments, natural language processing techniques, such as named entity recognition, may be used to accurately identify entities in the list of search results.

At a process 1850, a statistical analysis is provided for the one or more terms or entities within the list of search results. The statistical analysis may be performed by a statistical analysis module, such as statistical analysis module 1640, by a machine learning module, such as machine learning module 1650, or by a combination of modules. In some embodiments, the statistical analysis may include computing, for each term or entity of interest, a relationship score, a significance score, or both. Such statistical analyses may be based on a count of the number of occurrences of a given term in the search results, a count of the number of co-occurrences of the term with other terms, a score or ranking to compare the significance of a term relative to other terms, or the like.

In some embodiments, a significance score may be measured by computing a statistical significance metric that captures the relatedness of a given term (e.g., a token, an m-word phrase, an entity, or the like) to a user query. Illustratively, the statistical significance metric may be computed using the following equation when m is one (i.e., the phrase is a single word):

$$k \cdot \left( \ln\left[ \frac{\frac{k}{n}}{p} \right] - 1 \right)$$

Where k is the number of occurrences of the phrase within a list of search results (e.g., the list of text fragments returned by search module 1630 in response to a query), n is the total number of words in the list of search results, and p is the ratio N(w)/N where N(w) is the number of occurrences of the phrase within the corpus and N is the total number of words in the corpus.

When m is greater than one (i.e., the phrase is a multi-word phrase), the following equation may be used:

$$k \cdot \left( \ln\left[ \frac{\frac{k}{n-(m-1)k}}{p} \right] - 1 \right) + n \cdot \ln\left[ 1 - p + p \cdot (1-p)^{m-1} \right]$$

In some embodiments, where list of search results includes a non-binary context, the statistical significance metric may be adjusted based on the weights assigned to each appearance of the entity in the list of search results. For example, the value of k in the above equations may correspond to a weighted count of the number of occurrences of the entity in the search results.

It is to be understood that the above-described statistical analyses provided at process 1850 are illustrative, and various alternatives are possible. For example, statistical analysis module 1640 may determine a relatedness score EMS(Q,t) and a statistical significance metric pVal(Q,t). These values may capture the relatedness of an m-word phrase t to a user query Q.

At a process 1860, one or more enriched sets are optionally generated based on the statistical analysis of the one or more entities. In some embodiments, the enriched sets may include the most significant entities (e.g., the entities with the highest significance or relationship scores) identified at process 1850. For example, in the biomedical context, the one or more enriched sets may include a set of drugs, a set of diseases, and a set of genes. The enriched set of drugs, for instance, may identify the n drugs determined to be most significant or relevant to the user's query.

At process 1870, a response to the query is provided that includes at least one of the list of search results or the one or more enriched sets. In some embodiments, the response may be transmitted to an application, such as application 1602, and displayed to a user. The response may provide interactive user interface elements to the user to allow the user to interact with the search results or the enriched sets. For example, for the items in the enriched sets, the user may hover over the items to view the statistical analysis (e.g., the significance scores, the relationship scores, or the like) associated with the items.

Figure 19:
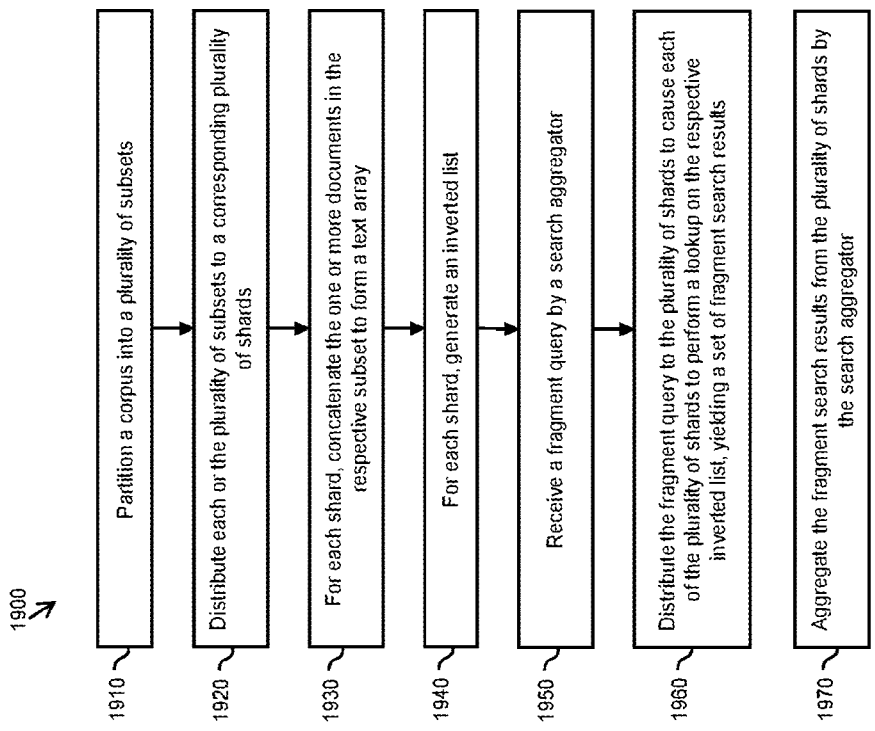
FIG. 19 is a simplified diagram of a method for performing a fragment search according to some embodiments.

FIG. 19 is a simplified diagram of a method 1900 for performing a fragment search according to some embodiments. In some embodiments consistent with FIGS. 15-18, method 1900 may be performed by a search module, such as search module 1630. The fragment search results generated using method 1900 may then be retrieved by a controller at process 1830 of method 1800.

At a process 1910, a corpus, such as corpus 1710, is partitioned into a plurality of subsets. The corpus includes a plurality of text documents or database records. In some embodiments, each of the subsets of the corpus may be approximately equal in size, e.g., they may occupy similar total disk space or they may include a similar number of documents.

At a process 1920, each of the plurality of subsets are distributed to a corresponding plurality of shards, such as shards 1721-1729. Each shard is responsible for processing a portion of the corpus in a distributed manner. In some embodiments, splitting the corpus among the shards may facilitate processing of the corpus using distributed computing resources (e.g., using distributed processors and/or storage systems). For example, one or more of the shards may be located on different machines within a data center and/or in different data centers.

At a process 1930, for each shard, the one or more documents in the respective subset of the corpus are concatenated to form a text array. For example, the text array may be contiguous with respect to the one or more documents.

At a process 1940, for each shard, an inverted list is generated. The inverted list includes an entry for each token (e.g., vocabulary word), in the corpus. Each entry includes a list of occurrences of the token in the corpus. For example, the list of occurrences may identify the positions of each occurrence of the token within the array formed at process 1930. In some embodiments, the inverted list may include a document identifier corresponding to the document in which the token occurs, an offset within the document to the occurrence of the token, or the like. In some embodiments, each entry in the inverted list may include a plurality of location identifiers for each occurrence of each token. The plurality of identifiers may be stored in an appropriate data structure, such as a triplet that identifies (1) the array index of the occurrence of the token within a contiguous array of concatenated documents, (2) the document identifier of the occurrence, and (3) the offset within the identified document to the occurrence.

The inverted list may be ordered to facilitate efficient lookup of tokens. For example, the inverted list may be ordered based on an ascending order of each token's positions within the array of text. The inverted list may be indexed using integer values associated with each token, such that given an integer corresponding to a token, the data structure containing inverted list efficiently returns a corresponding list of occurrences of the token.

At a process 1950, a fragment query, such as fragment query 1752, is received by a search aggregator, such as search aggregator 1754. The fragment query includes one or more query parameters indicating the desired search criteria for the fragment search. For example, the fragment query may include a query parameter (e.g., a combination of one or more tokens, words, or multi-word phrases to be searched, optionally joined by Boolean operators, such as AND, OR, and NOT). The fragment query may also include a size parameter indicating the desired size of the text fragments in the search results. The fragment query may further include a document parameter that specifies one or more criteria that a document should satisfy as a prerequisite for fragments in the document to be included in the search results. For example, the document parameter may include a criteria that eligible documents include a specified single or multi-word phrase (or logical combinations thereof) or a criteria that eligible documents be associated with document metadata (e.g., author names, publication years, document source, document type, or the like).

At a process 1960, the fragment query is distributed to the plurality of shards. Upon receiving the fragment query, each of the plurality of shards performs a lookup on the respective inverted list to identify matching fragments, yielding a set of fragment search results. In some embodiments, search criteria included in the fragment query (e.g., a restriction on the eligible documents to be included in the search) may be applied during the lookup.

At a process 1970, the sets of fragment search results from the plurality of shards are aggregated by the search aggregator. For example, the search results may be compiled, concatenated, sorted, ranked, or the like. Upon aggregating the search results, the search results may be provided to a controller or another module for further analysis, or may be returned to a user.

Figure 20A:
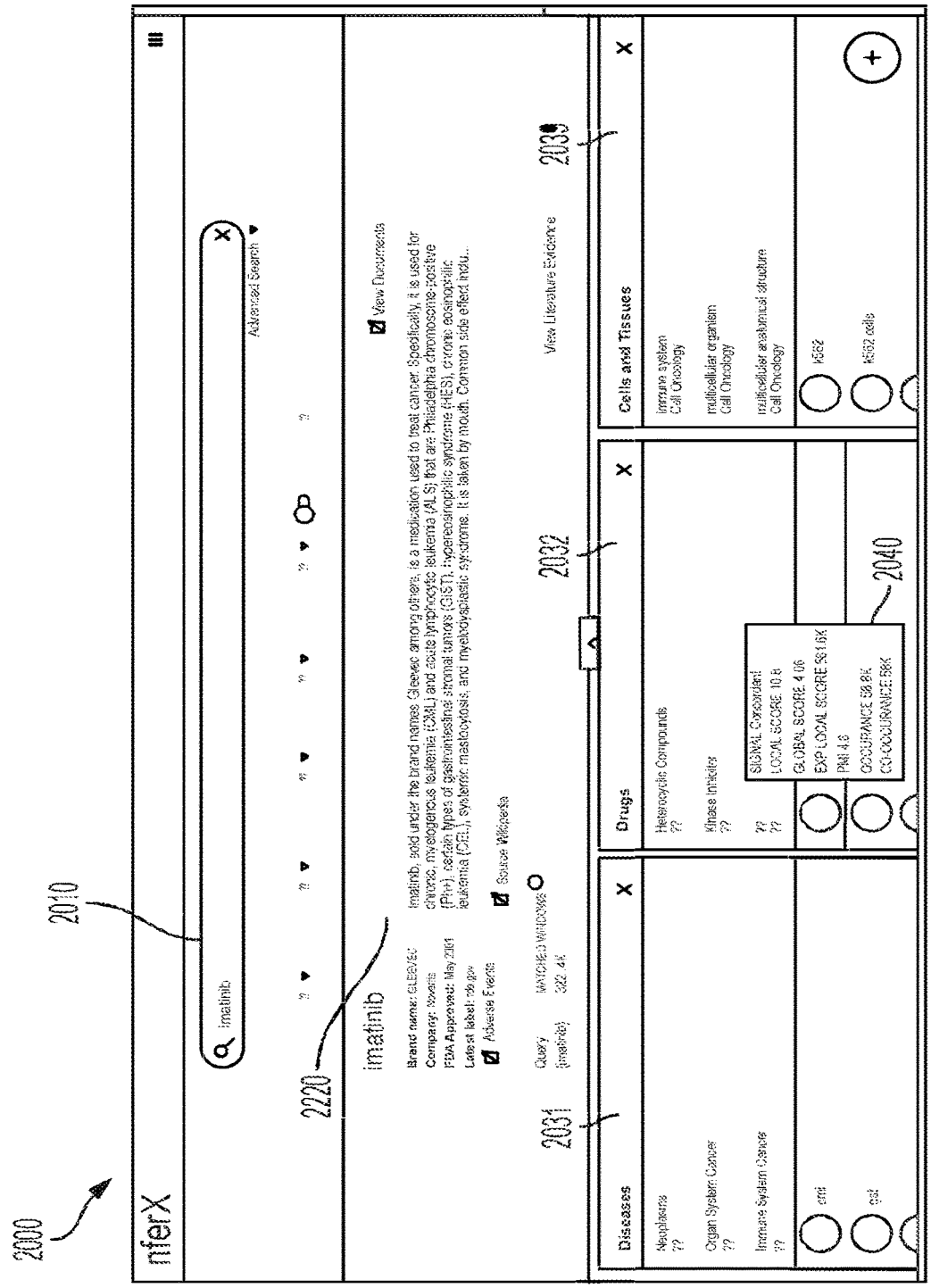
FIGS. 20A and 20B are screenshots of a graphical interface of an information retrieval system according to some embodiments.
Figure 20B:
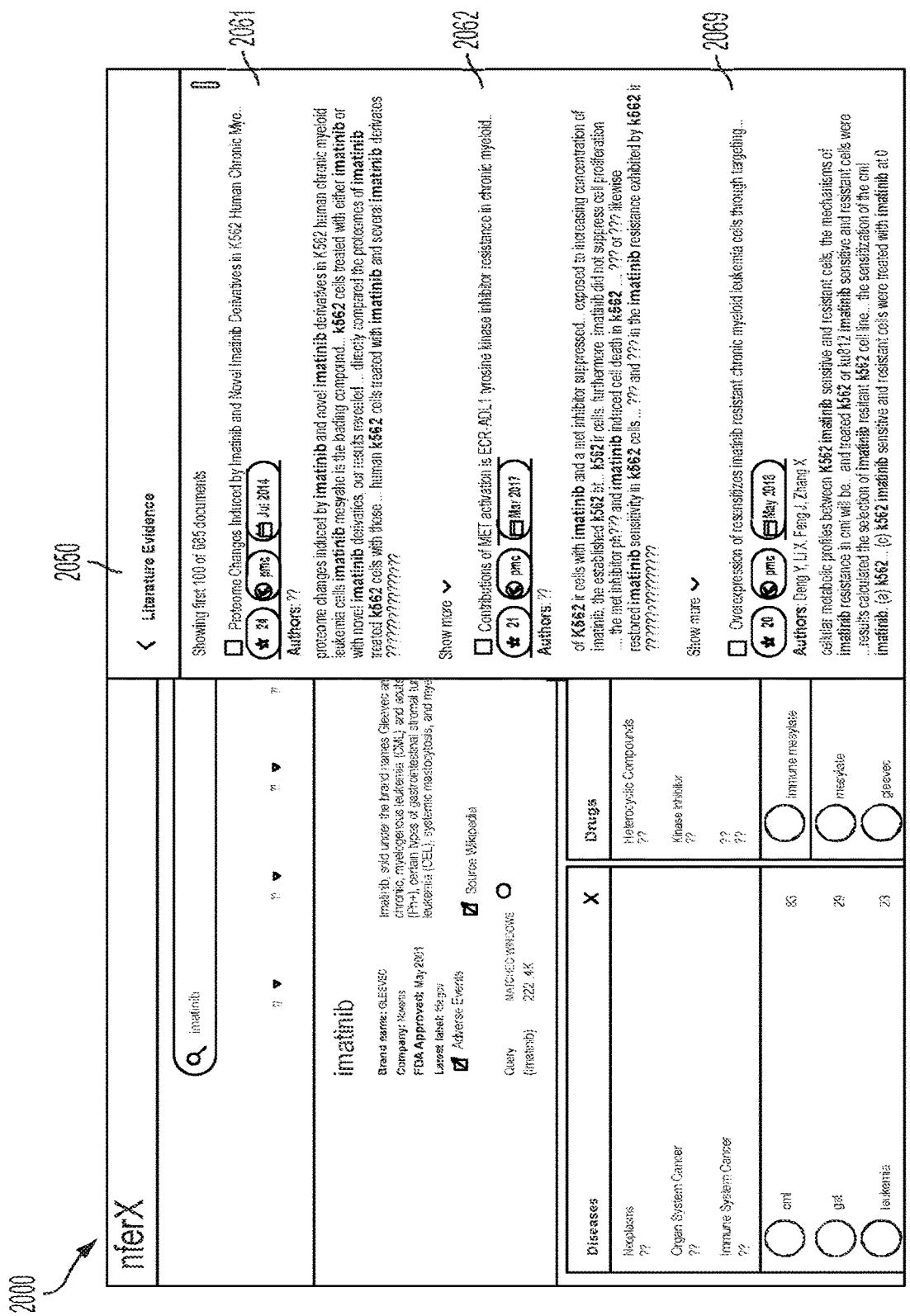

FIGS. 20A and 20B are screenshots of a graphical interface 2000 of an information retrieval system, such as information retrieval system 1604, according to some embodiments. In some embodiments consistent with FIGS. 15-19, graphical interface 2000 may be associated with application 1602. For illustrative purposes, the application is depicted as providing tools for a user to retrieve information in the biomedical domain.

As depicted in FIG. 20A, graphical interface 2000 includes a search input field 2010, in which a user may type or otherwise input a search term. In the illustration of FIGS. 20A and 20B, the search term is a drug named "imatinib."

In response to the user inputting the search term, the information retrieval system retrieves information associated with the search string and displays the information via graphical user interface 2000. In embodiments consistent with FIGS. 15-19, the information may be retrieved using various modules of the information retrieval system, such as controller 1610, knowledge base module 1620, search module 1630, statistical analysis module 1640, and machine learning module 1650. For example, graphical interface 2000 may display a matching article 2020 (or a portion thereof) that matches the search term. In this case, matching article 2020 corresponds to a Wikipedia article on "imatinib."

Graphical interface 2000 may further display enriched sets 2031-2039 of entities or concepts associated with the search term. In some embodiments, enriched sets 2031-2939 may include entities that are determined to be most significant to the search term (e.g., entities with the highest statistical significance score). As depicted in FIG. 20A, enriched sets 2031-2039 include a collection of diseases associated with imatinib 2031, a collection of drugs and classes of drugs associated with imatinib 2032, and a collection of cells and tissues associated with imatinib 2039.

In some embodiments, graphical interface 2000 may display statistical analyses and/or machine learning analyses associated with one or more terms or concepts displayed on graphical interface 2000. The analyses may be displayed by default or may dynamically appear when the user hovers over a particular term or concept. In some embodiments, the statistical or machine learning analyses may be performed using statistical analysis module 1640, machine learning module 1650, or a combination thereof. The underlying data used in the analysis may be retrieved from knowledge base 1620 and/or search module 1630. For example, as depicted in FIG. 20, a set of analyses 2040 is displayed when the user hovers over the term "imatinib mesylate," including various scoring metrics and occurrence/co-occurrence metrics (e.g., the number of occurrences of the term in the corpus and the number of co-occurrences of the term with the search term).

In some embodiments, graphical interface 2000 may provide a widget 2050 that displays additional information about the search term in response to a user selection. As depicted in FIG. 20B, widget 2050 displays literature evidence (e.g., compilations of published studies on the efficacy of imatinib) associated with search term. For example, documents 2061-2069 are depicted along with text fragments within documents 2061-2069 that include the search term or related terms. In this manner, a user of the application can efficiently determine whether imatinib is likely to be relevant or clinically effective for the purpose at hand.

Figure 21:
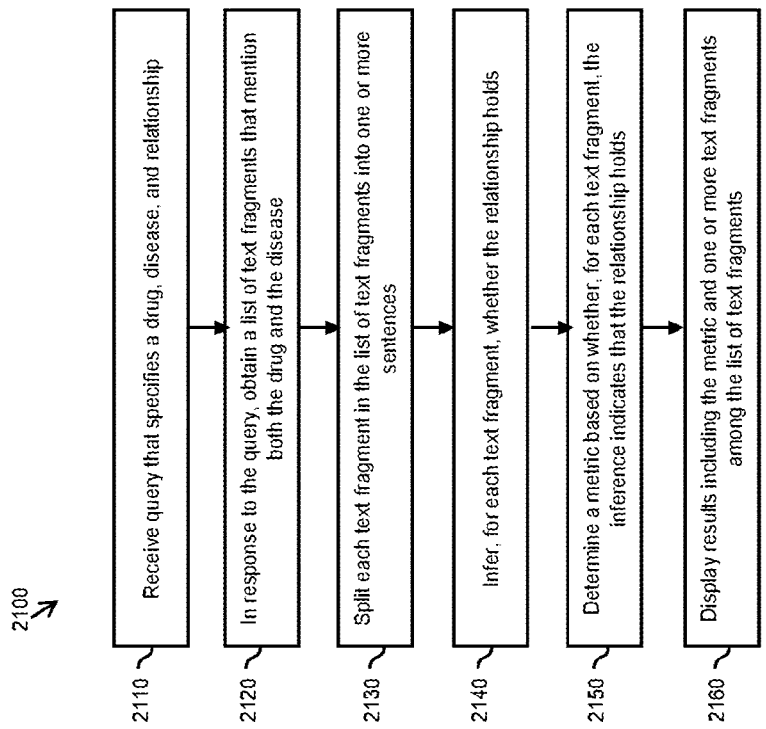
FIG. 21 is a simplified diagram of a method for information retrieval according to some embodiments.

FIG. 21 is a simplified diagram of a method 2100 for information retrieval according to some embodiments. According to some embodiments consistent with FIGS. 15-19, method 2100 may provide an illustrative example of how an information retrieval system, such as information retrieval system 1500, can be used to identify and analyze relationships in the biomedical domain. An exemplary goal of a user in method 2100 is to determine whether scientific literature shows evidence of specified relationship between a first entity (e.g., a drug, a chemical, etc.) and a second entity (e.g., a disease, a biomolecule, a gene, etc.). Examples of specified relationships include, but are not limited to, an adverse event relationship, a targeting relationship (e.g., a relationship in which a drug or chemical targets a biomolecule, gene, etc.), or a modality relationship (e.g., a relationship in which a drug or chemical has a particular therapeutic modality). Illustratively, in the embodiments of method 2100 described below, the first entity corresponds to a drug and the second entity corresponds to a disease. However, it is to be understood that various embodiments of method 2100 may be used to analyze relationships between various other types of entities.

At a process 2110, a query is received that specifies each of the drug, the disease), and the relationship. In some embodiments, the drug, disease, and relationship may be collected from a user using an input form of a graphical interface.

At a process 2120, in response to the query, a list of text fragments that match the query (e.g., by mentioning both the drug and the disease) is obtained. In some embodiments, the list of text fragments may be retrieved from a corpus (e.g., corpus 1710) using a search system, such as search module 1630. In some embodiments, the scope of the search may be expanded by identifying synonyms and other terms related to the query terms using, e.g., knowledge base module 1620. Text fragments that match the synonyms may then be included in the search results. In some embodiments, the scope of the search may be limited by placing constraints on the scope of the search, such as constraints on the types of documents to be searched (e.g., the search may be constrained to documents from particular journals published during a particular time frame).

At a process 2130, each text fragment is split into one or more sentences. In some embodiments, the text fragments may be split using a first natural language processing or machine learning system, such as machine learning module 1650.

At a process 2140, it is inferred, for each text fragment, whether the relationship holds (e.g., whether the drug and disease have an adverse event relationship). In some embodiments, the inference may be made using a second machine learning system, such as machine learning module 1650. For example, the second machine learning system may host a machine learning model trained to identify whether an adverse event relationship holds based on an input comprising text fragments formatted as a list of sentences.

At a process 2150, a metric is determined based whether, for each text fragment, the inference indicates that the relationship holds. For example, the metric may include the fraction of text fragments that are inferred to exhibit the adverse event relationship (or other specified relationship).

At a process 2160, results of the analysis are displayed, including the metric and one or more text fragments among the list of text fragments. The one or more text fragments may be labeled according to whether or not they were inferred to exhibit the specified relationship at process 2140. Illustrative embodiments of displaying the results of the analysis are discussed in further detail below with reference to FIGS. 22A and 22B.

It is to be understood that FIG. 21 is merely illustrative, and that various other embodiments are possible. For example, method 2100 may be used to identify relationships between other types of entities (e.g., entities other than drugs and diseases).

Figure 22A:
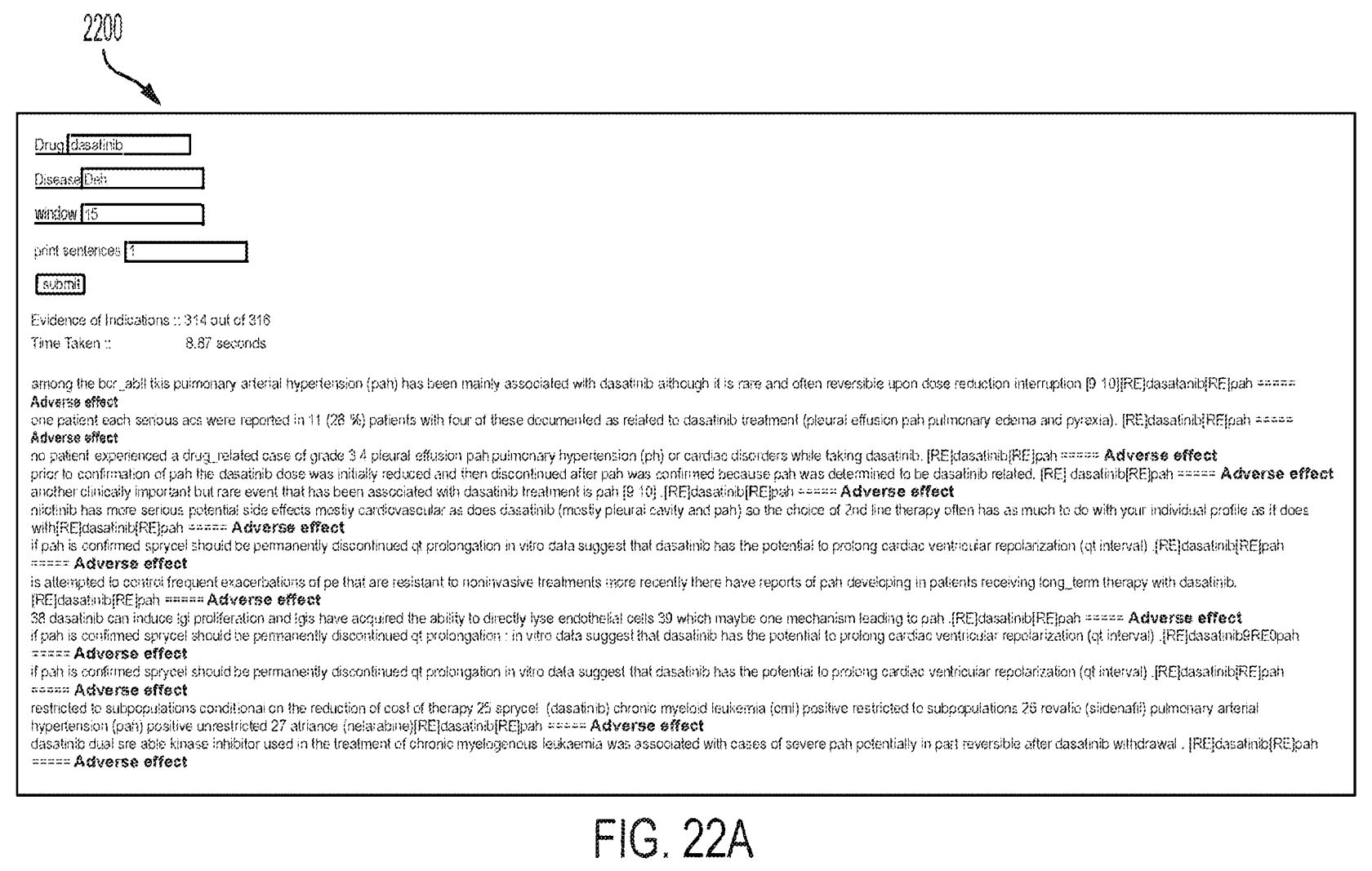
Figure 22B:
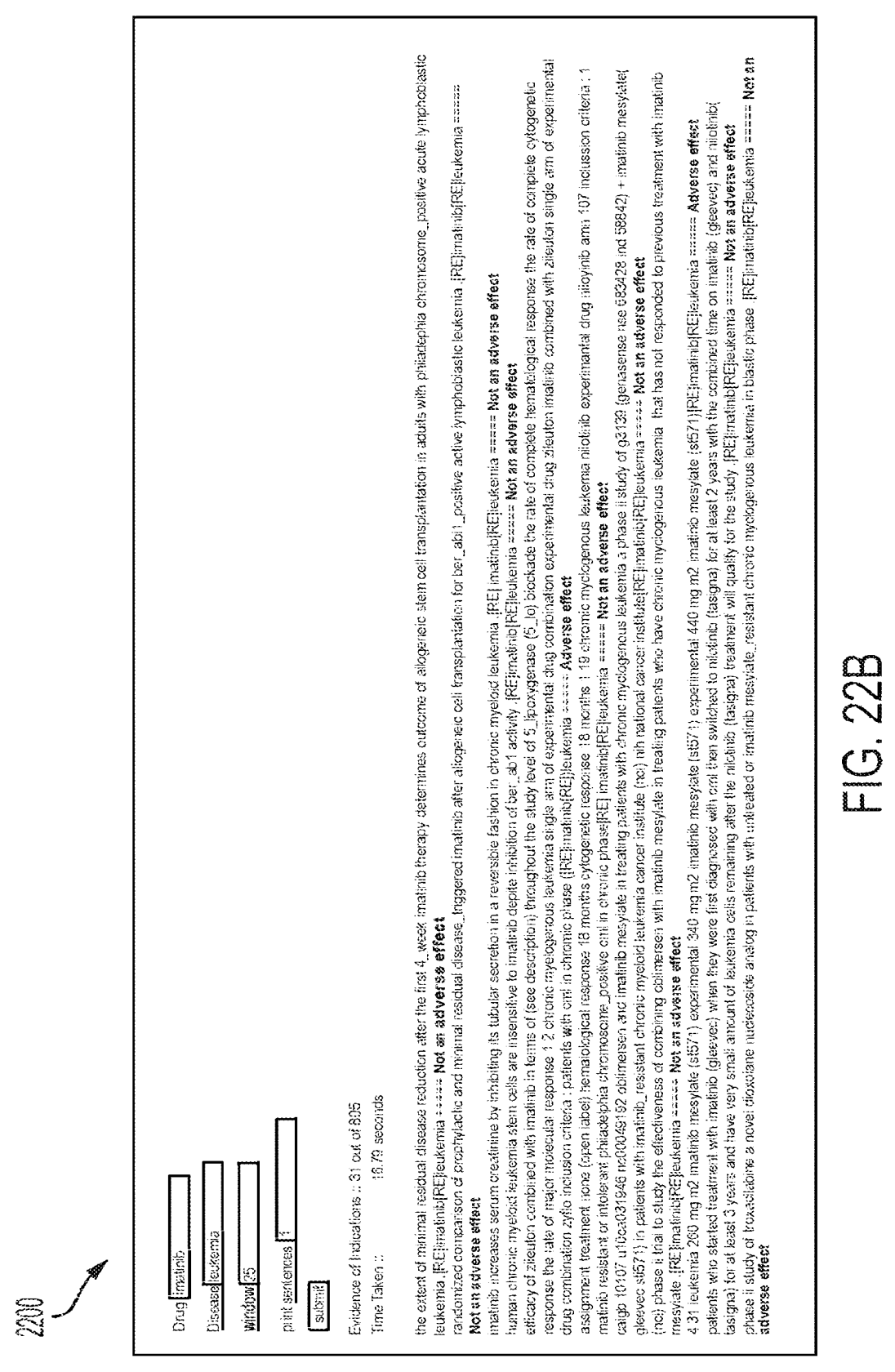

FIGS. 22A and 22B are screenshots of a graphical interface 2200 of an information retrieval system according to some embodiments. According to some embodiments consistent with FIGS. 15-21, graphical interface 2200 may display the results generated during method 2100. In FIG. 22A, the user seeks to determine whether the drug Dasatinib causes Pulmonary Arterial Hypertension as an adverse event. The displayed results indicate that there is overwhelming evidence that this adverse event relationship is true, as 314 out of 316 of the text fragments in the search results were labeled as indicating an adverse effect. In FIG. 22B, on the other hand, the user seeks to determine whether the drug Imatinib may be associated with Leukemia as an adverse event. Here, the overwhelming evidence suggests that such an adverse relationship does not exist, as only 31 out of the 805 matching text fragments are labeled as indicating an adverse effect.

As the above disclosure suggests, health records, such as electronic health records (EHRs) and patient charts, capture a wide range of information about the condition of patients. Health records are often represented in an unstructured or semi-structured format, such as the text of a note written by a physician. Whereas humans can understand the meaning of information that is presented in the form of text (e.g., words, phrases, and other terms that are represented as sequences of alphanumeric characters, symbols, emojis, etc.), computer technologies generally cannot grasp the semantic meaning of text in its human-readable form. Moreover, the condition of patients, as reflected in their health records, can change over time. Accordingly, it is desirable to develop techniques for the augmented curation and temporal discrimination of health records.

Further background for the present disclosure is provided in the paper entitled "Augmented Curation of Unstructured Clinical Notes from a Massive EHR System Reveals Specific Phenotypic Signature of Impending COVID-19 Diagnosis," (hereinafter, "Augmented Curation paper"), which is an attachment to U.S. Provisional Application No. 63/012,738 and is incorporated by reference herein in its entirety.

Figure 23:
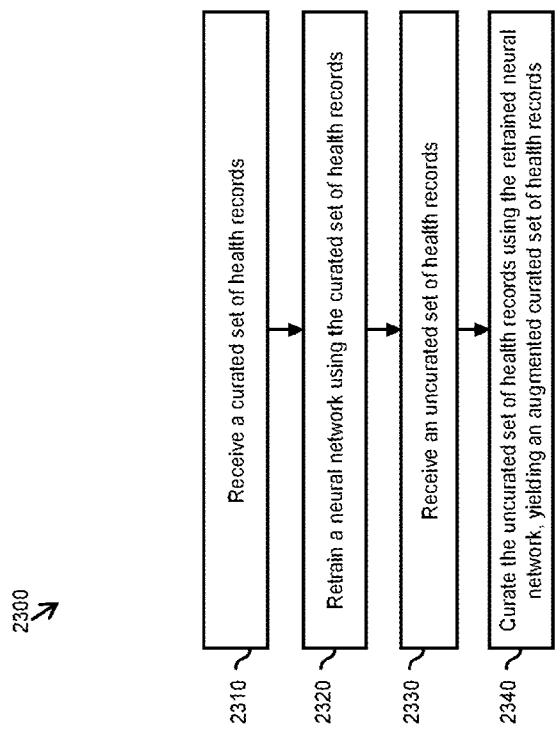
FIG. 23 is a simplified diagram of a method for augmented curation of health records according to some embodiments.

FIG. 23 is a simplified diagram of a method 2300 for augmented curation of health records according to some embodiments. The augmented curation of health records converts a raw health record, such as an electronic health records (EHR), a patient chart, or the like, into a structured representation of a patient phenotype (e.g., a snapshot of a patient's symptoms, diagnoses, treatments, or the like). The structured representation may then be visualized, used as an input for statistical or machine learning analysis, or the like. In some embodiments, the raw health records may be de-identified to mask patients' personal information or other information that may be unusable, for example, to comply with privacy regulations (e.g., HIPAA). Examples of such selective information masking techniques are described in further detail in the above-referenced U.S. Provisional Application Nos. 62/865,030 and 62/985,003, and in FIGS. 1-14 of the present disclosure. The de-identification of the health records may occur prior to, during, or after method 2300. In some embodiments consistent with FIGS. 1-22B, at least a portion of method 2300 may be performed using system 1500.

At a process 2310, a curated set of health records is received. Illustrative embodiments of process 2310 are described, for example, in the "Methods" section of the above-referenced Augmented Curation paper. For example, the curated set of health records may correspond to manually curated health records. Curating raw (or de-identified) health records may include identifying and grouping related words and phrases, such as synonyms for particular symptoms, diseases, medications, or the like, examples of which are described in the above-referenced Augmented Curation paper. For example, terms such as "SOB," "shortness of breath," and "dyspnea," among others, may be each be identified as corresponding to the symptom entity "shortness of breath" during curation. A given occurrence of an entity in a heath record may further be associated with a sentiment, e.g., a positive/negative sentiment that identifies the presence or absence of a symptom, the effectiveness or ineffectiveness of a medication, or the like. In this manner, a curated health record may provide a structured representation of a patient's phenotype. The curation may be performed by a physician or other individual with specialized knowledge or training in interpreting the raw health data. The size of the curated set of health records may be small relative to that typically used to train neural network models, and therefore may achieve the desired accuracy with less labor-intensive or time-consuming curation. For example, the curated set of health records may correspond to data from the charts of 100 patients (or another number of records that is sufficient to capture the various words and phrases that are used to convey a given symptom, disease, or other entity), whereas a typical neural network model may be trained using many thousands of curated records.

At a process 2320, a neural network is trained using the curated set of health records. Illustrative embodiments of process 2320 are described, for example, in the "Methods" section of the above-referenced Augmented Curation paper. For example, the neural network may correspond to a BERT-based neural network. In some embodiments, the neural network may have been previously trained using a corpus of health data, which may be larger than the curated set of health records received at process 2310. The neural network may correspond to a neural network classifier that extracts entities (e.g., symptoms, diseases, medications, or the like) contained in a given token and classifies them according to a positive/negative sentiment. The sentiment may be determined based on the surrounding phraseology using, e.g., natural language processing (NLP) techniques. For example, the neural network may detect that the phrases "the patient exhibited shortness of breath" and "negative for dyspnea" each include the symptom entity "shortness of breath," but have different sentiments (the first phrase indicating the presence of the symptom, and the latter indicating its absence). In some embodiments, the curated set of health records may include entities in addition to the entities in the corpus that was used to train the neural network. Accordingly, the curated set of health data may expand the set of entities that the neural network is able to recognize, while leveraging the accuracy in performing the sentiment analysis provided by the pretrained neural network.

In some embodiments, the neural network may achieve a certain performance metric as a result of training during process 2320. For example, the performance metric may correspond to the accuracy of the neural network and may be measured using test data, such as a portion of the curated set of health records that are set aside for testing purposes and are not used for training. Due to the limited size of the curated set of health records relative to a typical training set for a neural network, the performance metric that the neural network achieves may accordingly be limited.

At a process 2330, an uncurated set of health records is received. Illustrative embodiments of process 2330 are described, for example, in the "Methods" section of the above-referenced Augmented Curation paper. For example, the uncurated set of health records may include raw electronic health records or patient charts, which may be de-identified as discussed above. The uncurated set of health records may be tokenized, e.g., broken into sentences, words, or other text fragments. In some embodiments, the size of the uncurated set of health records may be larger than the curated set of health records (e.g., it may include a greater number of records, a greater overall amount of patient data, or both).

At a process 2340, the uncurated set of health records is curated using the trained neural network of process 2320. Illustrative embodiments of process 2340 are described, for example, in the "Methods" section of the above-referenced Augmented Curation paper. Process 2340 may yield an augmented curated set of health records that includes the curated sets of health records from processes 2310 and 2340. Curating the uncurated set of health records may include performing entity recognition and sentiment analysis on each token of each record, yielding a structured representation of the patient phenotype captured in each record. In some embodiments, the curated health records generated at process 140 may be verified, e.g., accepted or rejected and reclassified. The verification may include providing the curated health records to a physician or other skilled or trained individual with sufficient expertise to identify errors in the curated health records. The individual may then confirm the accuracy of the curated health records or provide a corrected version of the curated health records (e.g., a version in which erroneous entries have been reclassified by the trained individual) In general, verifying the automatically curated health records to detect and address occasional inaccuracies may be performed more efficiently than manually curating the underlying raw health records. The verified curated health records may be used to iteratively re-train the neural network model or train new neural network models as the augmented curation process progresses, leading to increases in curation efficiency and model accuracy. Process 2340 may be performed in one or more stages that involve successively less filtering of the curated results, which reflects the increasing accuracy of the augmented curation as the neural network is retrained.

Accordingly, method 2300 generates structured representations of patient phenotypes based on raw (and/or de-identified) health records. These structured representations may be more suitable for computational analysis than the raw health records. For example, the structured representations may be used to populate a structured database of health records. The data may be visualized, used as an input for statistical or machine learning analysis, or the like. Examples of computational analysis that may be performed using structured representations are described in further detail in the above-referenced U.S. Provisional Application Nos. 62/962,146 and 62/985,003, the Augmented Curation paper, and FIGS. 1-22.

In some embodiments, a structured databased of health records that is populated based on method 2300 may be used to perform enrichment analysis. For example, an enrichment analysis may include identifying early predictors associated with a disease, such as a set of symptoms or other patient characteristics that indicate a likelihood that a patient has a disease. Enrichment analysis may include characterizing a patient cohort, such as by identifying attributes that are closely associated with a particular patient cohort. The structured database can also be used for retrospective analysis of patient information, such as discriminating among patient sub-groups using, e.g., a clustering algorithm. The ability to discriminate among or stratify patients may be particularly useful for conditions that are associated with a wide range of severity or outcomes (and which may be difficult to differentiate at earlier stages), such as pulmonary hypertension. In some embodiments, different treatment plans may be selected for different patient sub-groups. For example, a more vigorous treatment plan may be selected for a patient sub-group associated with worse outcomes than for patient sub-groups identified as being associated with a lower risk. Such tailored treatment plans may result in more efficient use of resources and better overall quality of care.

Moreover, method 2300 may be applied in real-time as new health data becomes available. In addition, method 2300 may be applied to emerging concepts of interest, such as new diseases, symptoms, and treatments (e.g., those that do not appear frequently in older literature), as a relatively small amount of curated data is used at process 2310 to add new entities to the analysis. Illustrative advantages of this approach are further described in the above-referenced U.S. Provisional Application Nos. 62/962,433, 62/962,146, and 62/985,003 and the Augmented Curation paper.

Figure 24:
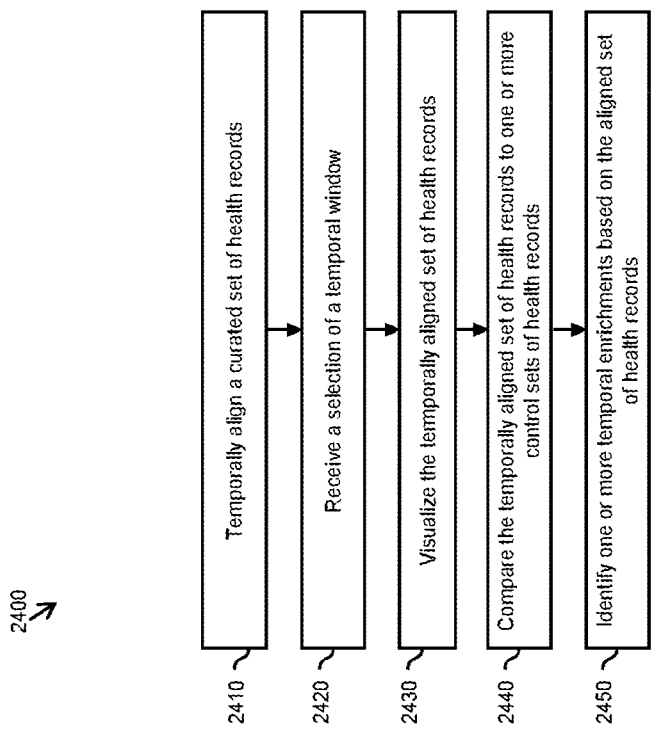
FIG. 24 is a simplified diagram of a method for temporal discrimination of health data according to some embodiments.

FIG. 24 is a simplified diagram of a method 2400 for temporal discrimination of health data according to some embodiments. In some embodiments consistent with FIGS. 1-22B, at least a portion of method 2400 may be performed using system 1500.

At a process 2410, a curated set of health records is temporally aligned. Illustrative embodiments of process 2410 are described, for example, in the "Methods" section of the above-referenced Augmented Curation paper. For example, the curated set of health records may correspond to the curated set of health records generated using method 2300. Temporally aligning the health records may include identifying the occurrence of a predetermined event in a given patient's health history, such as the date a particular diagnostic test was administered, the date a particular symptom was first observed, or the like. The patient's health records are then aligned relative to the date of occurrence of the predetermined event. For example, if the date of occurrence of the predetermined event is designated day 0, then a patient's phenotype recorded three days prior to the event may be designated day −3, and a phenotype recorded four days after the event may be designated day 4. The date of a patient's phenotype may be determined based on metadata associated with a patient record (e.g., a timestamp), information included within a given record (e.g., a physician's note indicating the date), or the like. In some embodiments, the date may be determined using natural language processing techniques. For example, if a record includes the phrase "patient began coughing three days ago," then natural language processing may be used to determine that the starting date of the cough symptom was three days prior to the date of the record.

At a process 2420, a selection of a temporal window is received. Illustrative embodiments of process 2420 are described, for example, in the "Methods" section of the above-referenced Augmented Curation paper. For example, the temporal window may correspond to a small temporal window (e.g., 10-30 days) before and after a seminal test (such as testing for COVID19). The temporal window may be based on the condition being studied. For example, a larger temporal window (e.g., one or more years) before and after a diagnosis may be used to study a condition that evolves more slowly, such as pulmonary hypertension.

Figure 25:
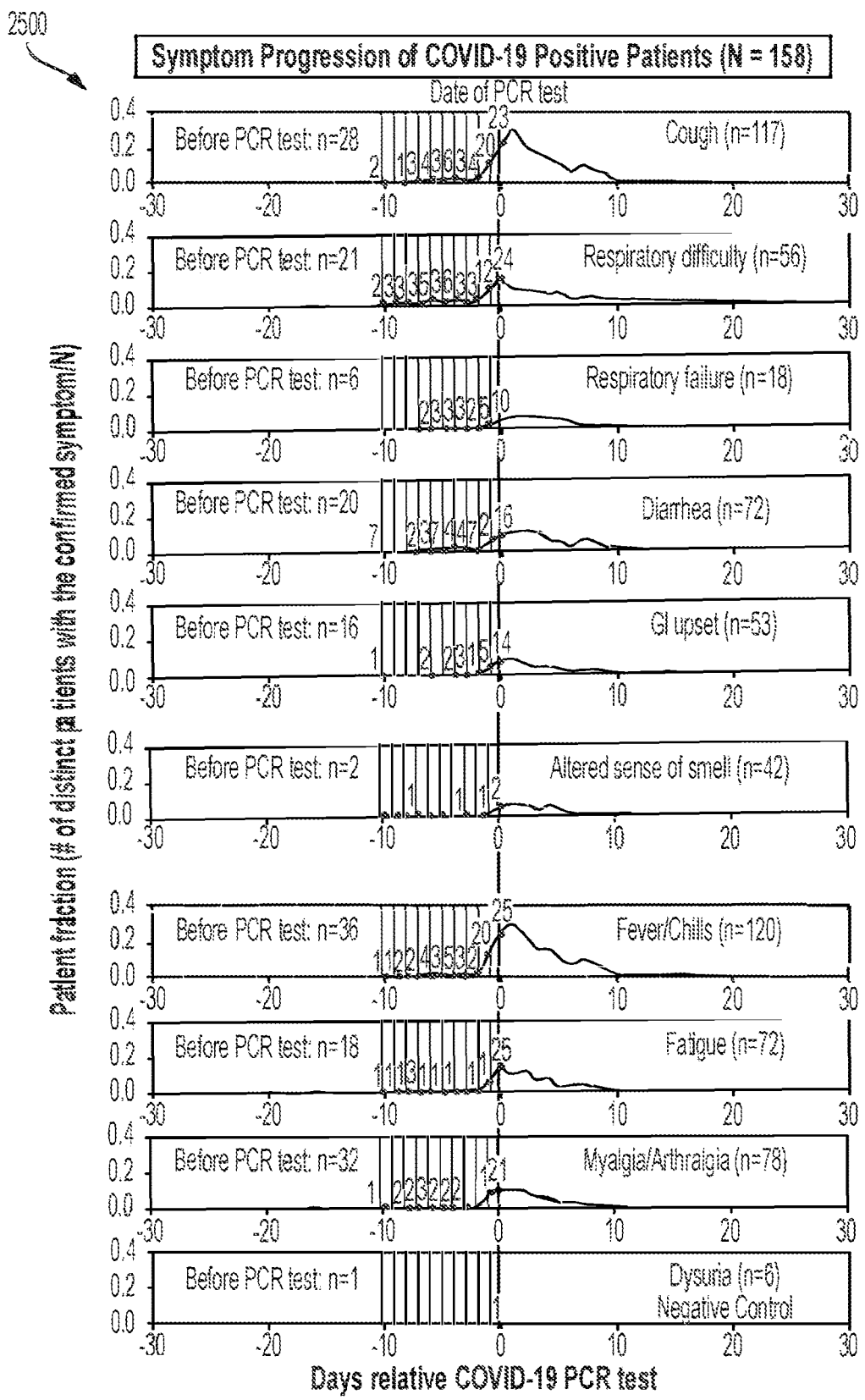
FIG. 25 is a simplified diagram of a visualization generated based on a temporally aligned set of health records according to some embodiments.
Figure 25:
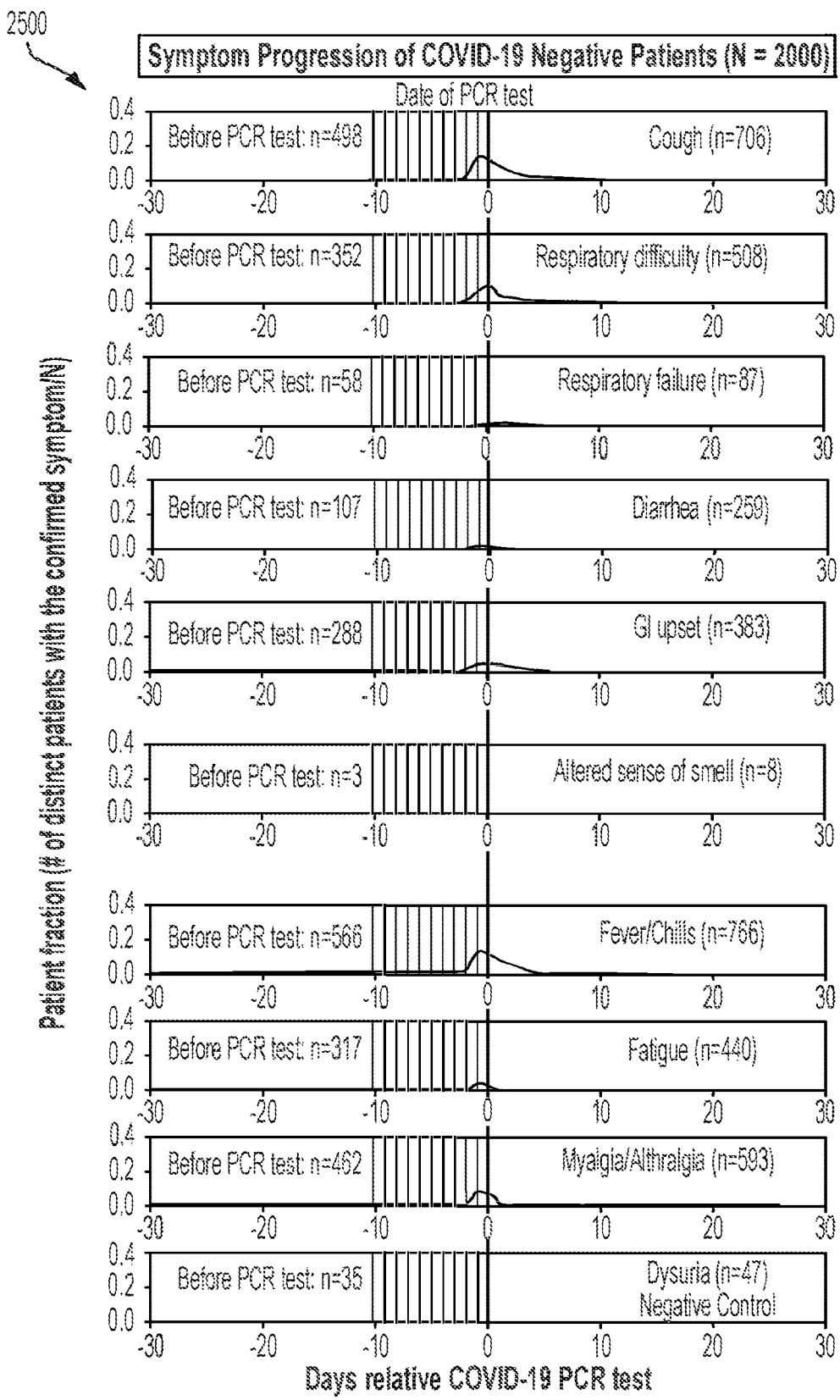

At a process 2430, the temporally aligned set of health records is visualized. For example, the number or percentage of patients with a particular phenotype (e.g., exhibiting a particular system) within N days of a predetermined event may be plotted as a function of time throughout the temporal window. Such visualizations may be useful for downstream decision making by physicians or scientists. For example, FIG. 25 is a simplified diagram of a visualization 2500 generated based on a temporally aligned set of health records according to some embodiments.

At a process 2440, the temporally aligned set of health records is compared to one or more control sets of health records. Illustrative embodiments of process 2440 are described, for example, in the "Methods" section of the above-referenced Augmented Curation paper. In some embodiments, comparing the temporally aligned health records to one or more control sets may be used to identify phenotypes (e.g., salient symptoms) that are predictive of a given condition (e.g., a positive COVID test). The control sets may be automatically determined and may illustratively correspond to (1) health records for a random set of "chronically ill patients"; (2) health records for a random set of the population who visits a clinic for reasons other than a chronic illness; and (3) health records for patients associated with conditions related to the condition being studied. As an example, when studying COVID19, the third control set may include "influenza" patients to discriminate their symptoms against COVID19 patients.

At a process 2450, temporal enrichments are identified based on the e temporally aligned set of health records. Illustrative embodiments of process 2450 are described, for example, in the "Methods" section of the above-referenced Augmented Curation paper. For example, temporal enrichment may be quantified using the ratio of the number of patients that exhibit a positive test result to the number of patients that exhibit a negative test result for a given day within the temporal window. Enrichments are described in further detail in the above referenced U.S. Provisional Application Nos. 62/962,146 and 62/985,003 and in FIGS. 1-22. For example, COVID19 patients may have a greater likelihood of exhibiting certain symptoms (e.g., cough, diarrhea, altered sense of taste, or the like) in the days leading up to a positive test compared with control patients (e.g., influenza patients). Such findings are likely to aid in clinical decision making or resource optimization (e.g., by prioritizing patients showing certain symptoms for testing). Temporal enrichments may further include co-enrichments, which identify combinations of factors that are associated with a risk of a particular outcome. Such combinations may be identified using a variety of known statistical analysis methods.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

Techniques for computing with private healthcare data have been disclosed. In one particular embodiment, the techniques may be realized as a method comprising constructing an isolated memory partition that forms a secure enclave and pre-provisioning software within the secure enclave. The secure enclave is available to one or more processors for running one or more application computing processes in isolation from one or more unauthorized computing processes running on the one or more processors. The pre-provisioned software is configured to execute instructions of the one or more application computing processes on the one or more processors by receiving at least one of input data or the instructions for the one or more application computing processes in an encrypted form; decrypting the at least one of input data or instructions using one or more cryptographic keys; executing the one or more application computing processes based on the decrypted at least one of input data or instructions to generate output data; generating a proof of execution that indicates that the one or more application computing processes operated on the received input data; encrypting the output data using the one or more cryptographic keys; and providing external access to the encrypted output data and the proof of execution.

In accordance with other aspects of this particular embodiment, the method further comprises receiving, from a data provider, the input data; receiving, from an instruction provider corresponding to an entity other than the data provider, one or more programs for analyzing the input data; loading the input data into the secure enclave; loading the one or more programs for analyzing the input data into the secure enclave; and running the one or more programs for analyzing the input data using the secure enclave.

In accordance with other aspects of this particular embodiment, the method further comprises de-identifying the input data prior to loading the set of clinical data records into the secure enclave, wherein de-identifying the input data comprises removing information that identifies one or more individuals or entities from the input data; providing a decryption key associated with the data or the instructions of the one or more application computing processes inside the secure enclave to the data provider or the instruction provider, respectively; and associating an input de-identification probability with input data prior to loading the input data into the secure enclave, wherein the secure enclave maintains the input de-identification probability in the output data.

In accordance with other aspects of this particular embodiment: the input data comprises clinical data that is de-identified by removing personally identifying information (PII) from the clinical data; and the input data and the one or more programs for analyzing the input data are loaded into the secure enclave in a same transaction.

In accordance with other aspects of this particular embodiment, the method further comprises connecting the secure enclave to a web server running inside a second secure enclave and causing the output data of the secure enclave to be displayed as a web page on a web client or web browser.

In accordance with other aspects of this particular embodiment: the input data being processed by the web server inside a secure enclave is not accessible to the web browser or the web client; and the output data displayed via the web server is associated with a cryptographic object associated with the secure enclave.

In accordance with other aspects of this particular embodiment, the method further comprises receiving the input data or instructions from a curation service, wherein the curation service determines that the input data or instructions are privacy-preserving In accordance with other aspects of this particular embodiment: the secure enclave is communicatively coupled to one or more other secure enclaves to form a pipeline, wherein the output data from the secure enclave is provided as input data to a subsequent secure enclave in the pipeline; the proof of execution comprises a cryptographic object; the cryptographic object is a representation of the contents of the secure enclave; the representation of the contents of the secure enclave proves that no unauthorized computer program operated on the input data; the representation of the contents of the secure enclave proves that an input de-identification probability associated with the input data was maintained by the secure enclave; and the cryptographic object is linked with one or more other cryptographic objects representing contents of the one or more other secure enclaves in the pipeline.

In accordance with other aspects of this particular embodiment: running the one or more computing processes in the secure enclave further comprises generating a unique signature for the secure enclave based on the at least one of input data or instructions; the received input data and the instructions of the one or more application computing processes are not accessible to any other secure enclaves linked to the secure enclave in a pipeline; the received input data and instructions of the one or more application computing processes is not accessible to an operator of the pipeline; the one or more unauthorized computing processes include at least one privileged software, privileged firmware, or a network interface process; and the input data comprises a set of clinical data records.

In one particular embodiment, the techniques may be realized as an information masking method comprising receiving a text sequence, providing the text sequence to a plurality of entity tagging models, aggregating tagged entities from the text sequence identified by the plurality of entity tagging models, and masking information in the text sequence based on the aggregated tagged entities. Each of the plurality of entity tagging models is trained to tag one or more portions of the text sequence having a corresponding entity type and to achieve a performance metric above a predetermined threshold In accordance with other aspects of this particular embodiment: the text sequence comprises at least a portion of an electronic health record; at least one of the plurality of entity tagging models is trained to tag entities of an entity type, the entity type including at least one of a personal name, an organization name, an age, a date, a time, a phone number, a pager number, a clinical identification number, an email address, an IP address, a web URL, a vehicle number, a physical address, a zip code, a social security number, or a date of birth; at least one of the plurality of entity tagging models tags entities based on a rule-based algorithm; at least one of the plurality of entity tagging models includes a machine learning model based on learning from sequences of text; masking the information in the text sequence comprises replacing one or more tagged entities with a placeholder marking a type of the one or more tagged entities; masking the information in the text sequence comprises changing a value of one or more tagged entities to a randomized value;

In accordance with other aspects of this particular embodiment, the information masking method further comprises: whitelisting one or more portions of the text sequence, wherein the one or more whitelisted portions are not provided to the plurality of entity tagging models passing the aggregated tagged entities through a one or more dreg filters, each of the one or more dreg filters being configured to filter a corresponding entity type based on at least one of a rule-based template or a pattern matching filter. The rule-based template may be created by mapping each of the one or more portions of the text sequence to a corresponding syntax template, identifying a candidate syntax template based on a machine learning model that infers one or more candidate syntax templates based on the one or more portions of the text sequence, and creating the rule-based template from the candidate syntax template by replacing each of the one or more tagged entities in the portion of the text sequence corresponding to the candidate template with a corresponding syntax token.

In another particular embodiment, the techniques may be realized as a method comprising receiving a query that specifies a drug, a disease, and a relationship; in response to the query, obtaining a list of text fragments that mention each of the drug and the disease, each text fragment in the list of text fragments including tokens corresponding to the drug and the disease and a plurality of additional token between and surrounding the drug and the disease; inferring, for each text fragment, whether the relationship holds using at least one neural network model trained; determining a metric based on a frequency with which the inference indicates that the relationship holds among the list of text fragments; and providing a response to the query that includes the metric and one or more text fragments among the list of text fragments.

In accordance with other aspects of this particular embodiment obtaining the list of text fragments comprises transmitting a second query based on the query to a search aggregator to cause the search aggregator to receive the second query distribute the second query to a plurality of shards to cause each of the plurality of shards to perform a lookup on a respective inverted list, wherein each of the plurality of shards processes a corresponding portion of a corpus to form the inverted list, the inverted list comprising a list of occurrences of each token in the corpus, yielding a set of search results and aggregate the search results from the plurality of shards to form the list of text fragments.

In accordance with other aspects of this particular embodiment the inverted list is generated by partitioning a corpus into a plurality of subsets, distributing each of the plurality of subsets to the corresponding plurality of shards, and, for each shard among the plurality of shards, concatenating the one or more documents in the respective subset to form a text array and determining a list of occurrences of each token in the respective subset, the list of occurrences being stored as the inverted list.

In accordance with other aspects of this particular embodiment, the method further comprises expanding the query to include one or more related terms associated with at least one of the drug, the disease, or the relationship, wherein the list of text fragments is obtained based on the expanded query, and wherein the one or more related terms are retrieved from a knowledge base that identifies relationships among a plurality of terms;

In accordance with other aspects of this particular embodiment, the method further comprises identifying one or more entities within the list of text fragments and generating one or more enriched sets based on a statistical analysis of the one or more entities, wherein the response to the query includes the one or more enriched sets, and wherein the one or more enriched sets include a subset of the one or more entities that have a highest statistical significance score among the one or more entities.

In accordance with other aspects of this particular embodiment: the list of text fragments is obtained from a corpus that includes at least one of a public literature corpus or a clinical data corpus; the corpus includes at least one text sequence comprising masked information; the corpus includes structured text data including at least one structured data field; and the corpus includes at least one patient record that is omitted from the response based on the at least one patient record being associated with a cohort that is less than a minimum cohort size.

In accordance with other aspects of this particular embodiment, the masked information is masked by receiving the at least one text sequence; providing the at least one text sequence to a plurality of entity tagging models, each of the plurality of entity tagging models being trained to achieve a performance metric above a predetermined threshold; aggregating tagged entities from the text sequence identified by the plurality of entity tagging models; masking information in the text sequence based on the aggregated tagged entities.

In another particular embodiment, the techniques may be realized as a method comprising receiving a first curated set of health records, each health record in the curated set of health records comprising a structured representation of patient information; training a first neural network model using the first curated set of health records; receiving a first uncurated set of health records; curating the first uncurated set of health records using the trained first neural network model, yielding a second curated set of health records; and training a second neural network model using the second curated set of health records, wherein the second neural network model achieves a second performance metric based on the training, the second performance metric indicating improved performance relative to the first performance metric.

In accordance with other aspects of this particular embodiment, the method further comprises iteratively performing the steps of: receiving an uncurated set of health records for a current iteration; curating the uncurated set of health records for the current iteration using a trained neural network model from the previous iteration, yielding curated set of health records for the current iteration; and training a neural network model for the current iteration using the curated set of health records for the current iteration.

In accordance with other aspects of this particular embodiment, the method further comprises receiving a second uncurated set of health records and curating the second uncurated set of health records using the trained second neural network model, yielding a third curated set of health records; populating a structured database of health records based on a fourth curated set of health records, the fourth curated set of health records including at least one of the first curated set of health records, the second curated set of health records, the third curated set of health records, or a curated set of health records generated by iteratively training one or more neural network models, each of the one or more neural network models being trained using curated sets of health records generated during a previous iteration; performing an enrichment analysis based on the structured database of health records; discriminating among a plurality of patient sub-groups based on a clustering analysis and selecting a different treatment plan for each of the plurality of patient sub-groups; temporally aligning the third curated set of health records and identifying one or more temporal enrichments based on the temporally aligned set of health records.

In accordance with other aspects of this particular embodiment: the trained second neural network model curates the third curated set of health records based on an emergent concept of interest; the enrichment analysis comprises at least one of identifying disease predictors associated with a disease or characterizing a patient cohort; the third curated set of health records is temporally aligned based on at least one of a date of a positive test, a date of a medical procedure, or a date associated with usage of a medication; the one or more temporal enrichments are identified within a plurality of time windows; and the one or more temporal enrichments include at least one co-enrichment based on a plurality of factors.

In another particular embodiment, the techniques may be realized as a system comprising at least one computer processor communicatively coupled to and configured to operate in the system, wherein the at least one computer processor is further configured to perform the steps in one or more of the above-described methods; the second neural network model is trained using a combined set of health records the first curated set of health records and the second curated set of health records.

In another particular embodiment, the techniques may be realized as an article of manufacture comprising a non-transitory processor readable medium and instructions stored on the medium, wherein the instructions are configured to be readable from the medium by at least one computer processor communicatively coupled to and configured to operate in the information masking system and thereby cause the at least one computer processor to operate so as to perform the steps in the one or more of the above-described methods.

It is to be understood that the disclosed subject matter is not limited in its application to the details of construction and to the arrangements of the components set forth in the foregoing description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

We claim:

1. A method comprising:
   constructing an isolated memory partition that forms a secure enclave, wherein the secure enclave is available to one or more processors for running one or more application computing processes in isolation from one or more unauthorized computing processes running on the one or more processors; and
   pre-provisioning software within the secure enclave, wherein the pre-provisioned software is configured to execute instructions of the one or more application computing processes on the one or more processors by:
receiving at least one of input data or the instructions for the one or more application computing processes in an encrypted form;
loading the input data into the secure enclave;
loading one or more programs for analyzing the input data into the secure enclave;
running the one or more programs for analyzing the input data using the secure enclave;
decrypting the at least one of input data or instructions using one or more cryptographic keys;
executing the one or more application computing processes based on the decrypted at least one of input data or instructions to generate output data;
generating a proof of execution that proves that the one or more instructions of the one or more application computing processes operated on the received input data;
encrypting the output data using the one or more cryptographic keys; and
providing external access to the encrypted output data and the proof of execution.

2. The method of claim 1, further comprising:
receiving, by the one or more processors, from a data provider, the input data; and
receiving, by the one or more processors, from an instruction provider corresponding to an entity other than the data provider, the one or more programs for analyzing the input data.

3. The method of claim 2, further comprising de-identifying the input data prior to loading the set of clinical data records into the secure enclave, wherein de-identifying the input data comprises removing information that identifies one or more individuals or entities from the input data.

4. The method of claim 3, wherein the input data comprises clinical data that is de-identified by removing personally identifying information (PII) from the clinical data.

5. The method of claim 2, further comprising providing a decryption key associated with the data or the instructions of the one or more application computing processes inside the secure enclave to the data provider or the instruction provider, respectively.

6. The method of claim 2, further comprising associating an input de-identification probability with input data prior to loading the input data into the secure enclave, wherein the secure enclave maintains the input de-identification probability in the output data.

7. The method of claim 2, wherein the input data and the one or more programs for analyzing the input data are loaded into the secure enclave in a same transaction.

8. The method of claim 1, further comprising connecting the secure enclave to a web server running inside a second secure enclave and causing the output data of the secure enclave to be displayed as a web page on a web client or web browser.

9. The method of claim 8, wherein the input data being processed by the web server inside a secure enclave is not accessible to the web browser or the web client.

10. The method of claim 8, wherein the output data displayed via the web server is associated with a cryptographic object associated with the secure enclave.

11. The method of claim 1, further comprising receiving the input data or instructions from a curation service, wherein the curation service determines that the input data or instructions are privacy-preserving.

12. The method of claim 1, wherein the secure enclave is communicatively coupled to one or more other secure enclaves to form a pipeline, wherein the output data from the secure enclave is provided as input data to a subsequent secure enclave in the pipeline.

13. The method of claim 12, wherein the proof of execution comprises a cryptographic object.

14. The method of claim 13, wherein the cryptographic object is a representation of the contents of the secure enclave.

15. The method of claim 14, wherein the representation of the contents of the secure enclave proves that no unauthorized computer program operated on the input data.

16. The method of claim 14, wherein the representation of the contents of the secure enclave proves that an input de-identification probability associated with the input data was maintained by the secure enclave.

17. The method of claim 14, wherein the cryptographic object is linked with one or more other cryptographic objects representing contents of the one or more other secure enclaves in the pipeline.

18. The method of claim 1, wherein running the one or more computing processes in the secure enclave further comprises generating a unique signature for the secure enclave based on the at least one of input data or instructions.

19. The method of claim 1, wherein the received input data and the instructions of the one or more application computing processes are not accessible to any other secure enclaves linked to the secure enclave in a pipeline.

20. The method of claim 19, wherein the received input data and instructions of the one or more application computing processes is not accessible to an operator of the pipeline.

21. The method of claim 1, wherein the one or more unauthorized computing processes include at least one privileged software, privileged firmware, or a network interface process.

22. The method of claim 1, wherein the input data comprises a set of clinical data records.

23. A system comprising:
a non-transitory memory; and
one or more hardware processors configured to read instructions from the non-transitory memory that, when executed, cause the one or more hardware processors to perform operations comprising:
constructing an isolated memory partition that forms a secure enclave, wherein the secure enclave is available to the one or more hardware processors for running one or more application computing processes in isolation from one or more unauthorized computing processes running on the one or more hardware processors; and
pre-provisioning software within the secure enclave, wherein the pre-provisioned software is configured to execute instructions of the one or more application computing processes on the one or more processors by:
receiving at least one of input data or the instructions for the one or more application computing processes in an encrypted form;
loading the input data into the secure enclave;
loading one or more programs for analyzing the input data into the secure enclave;
running the one or more programs for analyzing the input data using the secure enclave;

decrypting the at least one of input data or instructions using one or more cryptographic keys;

executing the one or more application computing processes based on the decrypted at least one of input data or instructions to generate output data;

generating a proof of execution that proves that the one or more instructions of the one or more application computing processes operated on the received input data;

encrypting the output data using the one or more cryptographic keys; and providing external access to the encrypted output data and the proof of execution.

24. The system of claim 23, wherein the operations further comprise:

receiving from a data provider, a set of clinical data records;

receiving from an entity other than the data provider, a program for analyzing the set of clinical data records;

loading the set of clinical records and the program for analyzing the set of clinical data records into the secure enclave; and running the program for analyzing the set of clinical data records using the secure enclave.

25. The system of claim 24, wherein the operations further comprise deidentifying the set of clinical data records prior to loading the set of clinical data records into the secure enclave.

26. The system of claim 24, wherein the operations further comprise providing a decryption key associated with the secure enclave to the data provider.

27. The system of claim 23, wherein the operations further comprise connecting the secure enclave to a web browser running inside a second secure enclave and causing the output data of the secure enclave to be displayed as a web page on a web client or web browser.

28. The system of claim 23, wherein the secure enclave is communicatively coupled to one or more other secure enclaves to form a pipeline, wherein the output data from the secure enclave is provided as input data to a subsequent secure enclave in the pipeline.

29. The system of claim 23, wherein the proof of execution comprises a cryptographic object.

30. The system of claim 23, wherein running the one or more computing processes in the secure enclave further comprises generating a unique signature for the secure enclave based on the at least one of input data or instructions.

31. A non-transitory computer-readable medium storing instructions that, when executed by one or more hardware processors, cause the one or more hardware processors to perform operations comprising:

constructing an isolated memory partition that forms a secure enclave, wherein the secure enclave is available to the one or more hardware processors for running one or more application computing processes in isolation from one or more unauthorized computing processes running on the one or more hardware processors; and pre-provisioning software within the secure enclave, wherein the pre-provisioned software is configured to execute instructions of the one or more application computing processes on the one or more processors by:

receiving at least one of input data or the instructions for the one or more application computing processes in an encrypted form;

loading the input data into the secure enclave;

loading one or more programs for analyzing the input data into the secure enclave;

running the one or more programs for analyzing the input data using the secure enclave;

decrypting the at least one of input data or instructions using one or more cryptographic keys;

executing the one or more application computing processes based on the decrypted at least one of input data or instructions to generate output data;

generating a proof of execution that proves that the one or more instructions of the one or more application computing processes operated on the received input data;

encrypting the output data using the one or more cryptographic keys; and providing external access to the encrypted output data and the proof of execution.

32. The non-transitory computer-readable medium of claim 31, wherein the operations further comprise:

receiving from a data provider, a set of clinical data records;

receiving from an entity other than the data provider, a program for analyzing the set of clinical data records;

loading the set of clinical records and the program for analyzing the set of clinical data records into the secure enclave; and running the program for analyzing the set of clinical data records using the secure enclave.

* * * * *